(12) United States Patent
Baudoin et al.

(10) Patent No.: US 8,372,864 B2
(45) Date of Patent: Feb. 12, 2013

(54) 1-OXO-ISOINDOLINE-4-CARBOXAMIDE AND 1-OXO-1,2,3,4-TETRAHYDROISOQUINOLINE-5-CARBOXAMIDE DERIVATIVES, PREPARATION AND THERAPEUTIC USE THEREOF

(75) Inventors: Bernard Baudoin, Paris (FR); Michel Evers, Paris (FR); Arielle Genevois-Borella, Paris (FR); Andreas Karlsson, Paris (FR); Jean-Luc Malleron, Paris (FR); Magali Mathieu, Paris (FR)

(73) Assignee: Sanofi, Paris (FR)

( * ) Notice: Subject to any disclaimer, the term of this patent is extended or adjusted under 35 U.S.C. 154(b) by 204 days.

(21) Appl. No.: 12/693,597

(22) Filed: Jan. 26, 2010

(65) Prior Publication Data

US 2010/0197725 A1 Aug. 5, 2010

Related U.S. Application Data

(63) Continuation of application No. PCT/FR2008/001110, filed on Jul. 25, 2008.

(30) Foreign Application Priority Data

Jul. 27, 2007 (FR) ..................... 07 05499

(51) Int. Cl.
- *A61K 31/4035* (2006.01)
- *A61K 31/47* (2006.01)
- *C07D 209/44* (2006.01)
- *C07D 217/24* (2006.01)

(52) U.S. Cl. ......... 514/309; 514/416; 546/141; 548/472
(58) Field of Classification Search .................. 514/309, 514/416; 546/141; 548/472; 544/287
See application file for complete search history.

(56) References Cited

FOREIGN PATENT DOCUMENTS

| EP | 11477490 | 11/2004 |
|---|---|---|
| WO | WO 03/040096 | 5/2003 |
| WO | WO 2004/094430 | 11/2004 |
| WO | WO 2005/058915 | 6/2005 |
| WO | WO 2006/099352 | 9/2006 |
| WO | WO 2006/103088 | 10/2006 |

OTHER PUBLICATIONS

Mangialasche et al., LancetNeurol. 2010; 9: p. 702-716.*
Arun K. Ghosh et al., Memapsin 2 (Beta-Secretase) Inhibitor Drug, between Fantasy and Reality. Curr. Alzheimer Res., 2007, vol. 4, No. 4; p. 418-422.*
(Lelie White "Common Test Shows blood Clot Risk for Cancer Patient Getting chemo", University of Rochester Medical Center Newsroom, Dec. 5, 2005; p. 1).*
Haugnes et al. J. Clin. Oncol. 28 (30), Oct. 20, 2010; p. 4649-4657).*
Grau et al. Stroke 1995; 26:373-379.*
Schafer et al. Drug discovery Today 2008, 13 (21/22), 913-916.*
Horig et al. Journal of Translation Medicine 2004, 2(44); p. 1-8.*
Luo et al. (Cell, 2009, 136, pp. 823-837)).*
Beher, D., et. al., Protease Inhibitors as Potential Disease-Modifying Therapeutics for Alzheimer's Disease, Expert Opin. Invest. Drugs, vol. 14, pp. 1385-1409, (2005).
Citron, M., et. al., Strategies for Diease Modification in Alzheimer's Disease, Nature Reviews, vol. 5, (2004), pp. 677-685.
Durham, T. B., et. al., Progress Toward the Discovery and Development of Efficacious BACE Inhibitors, Curr. Opin. Drug Disc. Dev., vol. 9, pp. 776-791, (2006).
Ghosh, A. K., et. al., B-Secretase as a Therapeutic Target for Inhibitor Drugs, Current Medicinal Chemistry, vol. 99, pp. 1135-1144, (2002).
Kisfaludy, L., et. al., Rapid and Selective Formylation With Pentafluorophenyl Formate, Synthesis, vol. 5, pp. 510, (1987).
Wiedemann, S., et. al., Primary 1-Arylcyclopropylamines from Aryl Cyanides With Diethylzinc and Titanium Alkoxides, Organic Letters, vol. 5, No. 5, pp. 753-755, (2003).
Ben-David, Y., et. al., Chelate-Assisted, Pd-Catalyzed Efficient Carbonylation of Aryl Chlorides, J. Am. Chem. Soc., (1989), vol. 111, pp. 8742-8744.
Ermolieff, J., et. al., Proteolytic Activation of Recombinant Pro-Memapsin 2 (Pro-B-Secretase) Studied With New Fluorogenic Substrates, Biochemistry, vol. 39, pp. 12450-12456, (2000).
KU, T. W., et al., An Alternate Enantiospecific Synthesis of Methyl (S)-7-Tert-Butoxycarbonyl-2,3,4,5-Tetrahydro-4-Methyl-3-Oxo-1H-1,4-Benzodiazepine-2-Acetate, Tetrahedron Letters, vol. 38, No. 18, pp. 3131-3134, (1997).
Orito, K. et. al., Prepration of Benzolactams by Pd(OAc)2-Catalyzed Direct Aromatic Carbonylation, J. Am. Chem. Soc., (2004), vol. 126, pp. 14342-14343.
Wang, Y-C., et. al., An Efficient Synthesis of Thalifoline, Synthesis, (2002), vol. 15, pp. 2187-2190.
Ferrer, S., et. al. N- and O-Alkylation of Isoquinolin-1-ones in The Mitsunobu Reaction: Development of Potential Drug Delivery Systems, J. Chem. Soc., Perkin Trans. 1, (2002), pp. 335-340.
Selkoe, D. J., et. al., Translating Cell Biology Into Therapeutic Advance's in Alzheimer's Disease, Nature, vol. 399, (1999), pp. A23-A31.
Roggo, S., et. al., Inhibition of BACE, A Promising Approach to Alzheimer's Disease Therapy, Current Topics In Medicinal Chemistry, (2002), vol. 2, pp. 359-370.

* cited by examiner

*Primary Examiner* — Yong Chu
*Assistant Examiner* — Valerie Rodriguez-Garcia
(74) *Attorney, Agent, or Firm* — Jiang Lin; Scully, Scott, Murphy & Presser, P.C.

(57) ABSTRACT

The present invention relates to derivatives of 1-oxo-isoindoline-4-carboxamides and of 1-oxo-1,2,3,4-tetrahydroisoquinoline-5-carboxamides, to the preparation thereof and to the therapeutic use thereof.

18 Claims, No Drawings

1-OXO-ISOINDOLINE-4-CARBOXAMIDE AND 1-OXO-1,2,3,4-TETRAHYDROISOQUINOLINE-5-CARBOXAMIDE DERIVATIVES, PREPARATION AND THERAPEUTIC USE THEREOF

This application is a Continuation of International Application No. PCT/FR2008/001110, filed Jul. 25, 2008, which is incorporated herein by reference in its entirety.

The present invention relates to derivatives of 1-oxo-isoindoline-4-carboxamides and of 1-oxo-1,2,3,4-tetrahydroisoquinoline-5-carboxamides, to the preparation thereof and to the therapeutic use thereof.

The presence of multiple senile plaques in brain tissue is one of the main histopathological alterations observed in Alzheimer's disease, these plaques form by deposition of fibrillary aggregates of a 4 kDa peptide (40-42 amino acids), known as amyloid β (Aβ) peptide. The production and gradual accumulation of this peptide could play a crucial role in the triggering and progression of Alzheimer's pathology, according to the amyloid cascade hypothesis (D. Seiko et al. *Nature* 399A (1999) 23; S. Roggo et al. *Top. Med. Chem.* 2 (2002) 359; A. Ghosh et al. *Curr. Med. Chem.* 9 (2002) 1135).

The Aβ peptide originates from the APP (Amyloid Precursor Protein) protein, which may be cleaved by at least three different proteolytic activities: 1) cleavage in the Aβ region by an α-secretase activity (thus preventing the formation of Aβ); 2) cleavage at the N-terminal end of Aβ by a β-secretase activity; 3) cleavage at the C-terminal end of Aβ by a γ-secretase activity. The consecutive cleavage of the APP protein at the β and γ sites leads to the formation of the Aβ peptide (M. Citron *Nat. Rev. Neurosci.* 5 (2004) 677-685; D. Beher et al. *Expert Opin. Invest. Drugs* 14 (2005) 1385-1409).

There is therefore a real interest in finding compounds that inhibit the production of the Aβ peptide (T. B. Durham et al. *Curr. Opin. Drug Disc. Dev.* 9 (2006) 776-791).

It has now been found that compounds, derivatives of 1-oxo-isoindoline-4-carboxamides and of 1-oxo-1,2,3,4-tetrahydroisoquinoline-5-carboxamides, possess a strong inhibitory activity with respect to the β-secretase activity.

One subject of the present invention is the compounds corresponding to the formula (I):

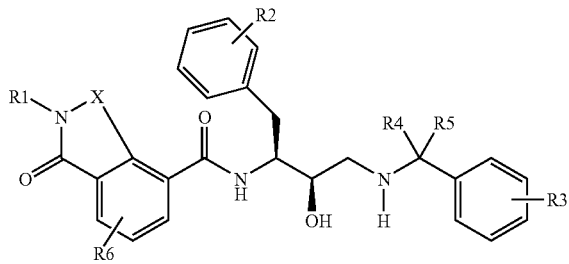

(I)

in which:

R1 represents a hydrogen atom, a $(C_1-C_{10})$alkyl, $(C_3-C_7)$cycloalkyl, $(CH_2)_n$—$(C_1-C_6)$alkenyl, $(CH_2)_n$—$(C_1-C_6)$alkynyl or $(C_1-C_6)$alkyl-Z—$(C_1-C_6)$alkyl group, in which Z represents a heteroatom chosen from O, N and $S(O)_m$, or else R1 represents a COOR, $S(O)_mR$, aryl or aralkyl group; the $(C_1-C_{10})$alkyl, $(C_3-C_7)$cycloalkyl, $(CH_2)_n$—$(C_1-C_6)$alkenyl, $(CH_2)_n$—$(C_1-C_6)$alkynyl, $(C_1-C_6)$alkyl-Z—$(C_1-C_6)$alkyl, aryl or aralkyl groups being optionally substituted with one or more groups chosen from a halogen atom, a $(C_1-C_6)$alkyl, $(C_3-C_7)$cycloalkyl, halo$(C_1-C_6)$alkyl, $(C_1-C_6)$alkoxy, halo$(C_1-C_6)$alkoxy, NR7R8, nitro, cyano, OR, COOR, CONR7R8 or $S(O)_m$NR7R8 group or an aryl group optionally substituted with a halogen atom;

R2 represents one or more groups chosen from a hydrogen atom, a halogen atom, a $(C_1-C_6)$alkyl, $(C_3-C_7)$cycloalkyl, $(C_1-C_6)$alkenyl, $(C_1-C_6)$alkynyl or $(C_1-C_6)$alkyl-Z—$(C_1-C_6)$alkyl group, in which Z represents a heteroatom chosen from O, N and $S(O)_m$, or else $R^2$ represents a halo$(C_1-C_6)$alkyl, $(C_1-C_6)$alkoxy, halo$(C_1-C_6)$alkoxy, hydroxy, nitro, cyano or amino group, an NR7R8, COOR, CONR7R8, OCO$(C_1-C_6)$alkyl or $S(O)_m$—NR7R8 group, or an aryl group, said aryl group possibly being optionally substituted with one or more groups chosen from a halogen atom, a $(C_1-C_6)$alkyl, $(C_3-C_7)$cycloalkyl, halo$(C_1-C_6)$alkyl, $(C_1-C_6)$alkoxy, halo$(C_1-C_6)$alkoxy, NR7R8, OR, nitro, cyano, COOR, CONR7R8 or $S(O)_m$NR7R8 group;

R3 represents a trifluoromethyl group;

R4 and R5 represent a hydrogen atom, or else R4 and R5 form, with the carbon atom that bears them, a saturated ring containing from 3 to 6 carbon atoms and optionally containing from 0 to 1 heteroatom, chosen from O, N or S;

R6 represents a group chosen from a hydrogen atom, a halogen atom, a $(C_1-C_6)$alkyl, $(C_3-C_7)$cycloalkyl or $(C_3-C_7)$cycloalkyl$(C_1-C_6)$alkyl group, a halo$(C_1-C_6)$alkyl, nitro or amino group, an NR7R8 or COOR group, an NR7$(SO_2)$R8 or CONR7R8 group, an aryl group or a heterocycle group, the aryl and heterocycle groups being optionally substituted with one or more groups chosen from a halogen atom, a $(C_1-C_6)$alkyl, $(C_1-C_6)$alkoxy or cyano group;

R, R7 and R8 represent, independently of one another, one or more groups chosen from a hydrogen atom, a $(C_1-C_6)$alkyl, $(C_3-C_7)$cycloalkyl or $(C_3-C_7)$cycloalkyl$(C_1-C_6)$alkyl group, an aryl or aryl$(C_1-C_6)$alkylene group, or else R7 and R8 may form, with the atom which bears them, a saturated, partially unsaturated or unsaturated ring containing from 5 to 7 carbon atoms and optionally containing, in addition, a heteroatom chosen from O, N or $S(O)_m$;

X represents a $(C_1-C_2)$alkylene group, optionally substituted with one or more $(C_1-C_6)$alkyl groups;

m represents an integer which may take the values 0, 1 or 2 and n represents an integer which may take the values 1, 2, 3, 4, 5 or 6;

the carbon bearing the benzyl group substituted by R2 is of S absolute configuration; and the carbon bearing the hydroxyl group is of R absolute configuration.

The compounds of formula (I) may comprise one or more asymmetric carbon atoms. They may therefore exist in the form of enantiomers or of diastereoisomers. These enantiomers or diastereoisomers, and also mixtures thereof, including racemic mixtures, are part of the invention.

The compounds of formula (I) may exist in the form of bases or addition salts with acids. Such addition salts are part of the invention.

These salts may be prepared with pharmaceutically acceptable acids, but the salts of other acids that are useful, for example, for the purification or isolation of the compounds of formula (I) are also part of the invention.

Within the context of the present invention, the following definitions apply:

$C_t$-$C_z$, where t and z may take the values of 1 to 10, is understood to mean a carbon-based chain or ring which may have from t to z carbon atoms, for example $C_1$-$C_3$ may characterize a carbon-based chain having from 1 to 3 carbon atoms;

a halogen atom: a fluorine, a chlorine, a bromine or an iodine;

an alkyl group: a linear or branched saturated aliphatic group. By way of examples, mention may be made of the methyl, ethyl, propyl, isopropyl, butyl, isobutyl, tert-butyl, pentyl, etc. groups;

a cycloalkyl group: a cyclic alkyl group. By way of examples, mention may be made of the cyclopropyl, methylcyclopropyl, cyclobutyl, cyclopentyl, cyclohexyl, etc. groups;

an alkylene group: a linear or branched saturated divalent aliphatic group. By way of example, a $C_{1-3}$-alkylene group represents a linear or branched divalent carbon-based chain having 1 to 3 carbon atoms, such as a methylenyl (—$CH_2$—), an ethylenyl (—$CH_2CH_2$—), a 1-methylethylenyl (—$CH(CH_3)CH_2$—) or a propylenyl (—$CH_2CH_2CH_2$—);

an alkenyl group: a linear or branched monounsaturated or poly-unsaturated aliphatic group comprising, for example, one or two ethylenically unsaturated groups;

an alkynyl group: a linear or branched monounsaturated or poly-unsaturated aliphatic group comprising, for example, one or two acetylenically unsaturated groups;

an alkoxy group: an —O-alkyl radical where the alkyl group is as defined previously;

a halo($C_1$-$C_6$)alkyl group: an alkyl group of which one or more hydrogen atoms have been substituted with a halogen atom. By way of examples, mention may be made of the $CF_3$, $CH_2CF_3$, $CHF_2$ or $CCl_3$ groups;

a halo($C_1$-$C_6$)alkoxy group: an —O-alkyl radical where the alkyl group is as defined previously and which is substituted by one or more identical or different halogen atoms. By way of examples, mention may be made of the $OCF_3$, $OCHF_2$ or $OCCl_3$ groups;

the sulfur and nitrogen atoms may be present in the oxidized state (N-oxide, sulfoxide, sulfone, etc.);

an aryl group: a cyclic aromatic group comprising between 6 and 14 carbon atoms. By way of example of an aryl group, mention may be made of phenyl or naphthyl;

a heterocycle group: an unsaturated, partially unsaturated monocyclic or polycyclic group having between 4 and 10 atoms chosen from carbon atoms and 1 to 4 heteroatoms chosen from N, O and S. Examples of such heterocyclic groups include pyrrole, furan, thiophene, pyrazole, imidazole, triazole, tetrazole, oxazole, isoxazole, oxadiazole, thiazole, isothiazole, thiadiazole, pyridine, pyrimidine, pyrazine, pyridazine or triazine.

In the various groups as defined below, the groups R1, R2, R3, R4, R5, R6, R, R7 and R8, when they are not defined, have the same definitions as those mentioned above.

Among the compounds of formula (I) that are subjects of the invention, a first group of compounds is constituted by the compounds for which:

X represents a methylene group optionally substituted with one or more ($C_1$-$C_6$)alkyl groups.

Among the compounds of formula (I) that are subjects of the invention, a second group of compounds is constituted by the compounds for which:

X represents an ethylene group optionally substituted with one or more ($C_1$-$C_6$)alkyl groups.

Among the compounds of formula (I) that are subjects of the invention, a third group of compounds is constituted by the compounds for which:

R6 represents a group chosen from a hydrogen atom, a halogen atom, a ($C_1$-$C_6$)alkyl or halo($C_1$-$C_6$)alkyl group, an $NR7SO_2R8$ group, an aryl optionally substituted with a cyano group, or else R6 represents a heterocycle.

Among this subgroup of compounds of formula (I) that are subjects of the invention, a fourth group of compounds is constituted by the compounds for which:

R6 represents a group chosen from a hydrogen atom, a chlorine atom or a fluorine atom, a methyl or trifluoromethyl group, an $NMeSO_2Me$ group, a phenyl substituted with a cyano group, or else R6 represents an oxazole.

Among the compounds of formula (I) that are subjects of the invention, a fifth group of compounds is constituted by the compounds for which:

R1 represents a ($C_1$-$C_{10}$)alkyl group, optionally substituted with one or more ($C_1$-$C_6$)alkyl groups, an aryl group optionally substituted with a halogen atom, or else R1 represents a ($C_1$-$C_6$)alkyl-O—($C_1$-$C_6$)alkyl group or an aralkyl group optionally substituted with a halogen atom;

R2 represents one or more groups chosen from a hydrogen atom or a halogen atom;

R4 and R5 represent a hydrogen atom or form, with the carbon atom which bears them, a cyclopropyl group;

R6 represents a group chosen from a hydrogen atom, a halogen atom, a ($C_1$-$C_6$)alkyl or halo($C_1$-$C_6$)alkyl group, an $NR7SO_2R8$ group, an aryl optionally substituted with a cyano group, or else R6 represents a heterocycle;

R7 represents a hydrogen atom or a ($C_1$-$C_6$)alkyl group; and

R8 represents a ($C_1$-$C_6$)alkyl group.

The combinations of groups one to five as defined above are also part of the invention.

In the names of the compounds, the dash "-" is part of the word and the dash "_" is only used for the break at the end of the line; it should be deleted in the absence of a break and should not be replaced by a normal dash nor by a space.

Among the compounds of formula (I) that are subjects of the invention, mention may especially be made of the following compounds:

N-[(1S,2R)-1-benzyl-2-hydroxy-3-{[3-(trifluoromethyl)benzyl]amino}propyl]-1-oxo-2-(1-propylbutyl)isoindoline-4-carboxamide and its hydrochloride (1:1)

N-[(1S,2R)-1-benzyl-2-hydroxy-3-({1-[3-(trifluoromethyl)phenyl]cyclopropyl}amino)propyl]-1-oxo-2-(1-propylbutyl)-1,2,3,4-tetrahydroisoquinoline-5-carboxamide and its hydrochloride (1:1)

N-[(1S,2R)-1-(3,5-difluorobenzyl)-2-hydroxy-3-({1-[3-(trifluoromethyl)phenyl]cyclopropyl}amino)propyl]-1-oxo-2-(1-propylbutyl)-1,2,3,4-tetrahydroisoquinoline-5-carboxamide and its hydrochloride (1:1)

N-[(1S,2R)-1-benzyl-2-hydroxy-3-{[3-(trifluoromethyl)benzyl]amino}propyl]-1-oxo-2-(1-propylbutyl)-1,2,3,4-tetrahydroisoquinoline-5-carboxamide and its hydrochloride (1:1)

2-benzyl-N-[(1S,2R)-1-(3,5-difluorobenzyl)-2-hydroxy-3-({1-[3-(trifluoromethyl)phenyl]cyclopropyl}amino)propyl]-1-oxo-1,2,3,4-tetrahydroisoquinoline-5-carboxamide and its hydrochloride (1:1)

N-[(1S,2R)-1-(3,5-difluorobenzyl)-2-hydroxy-3-({1-[3-(trifluoromethyl)phenyl]cyclopropyl}amino)propyl]-1-oxo-2-pentyl-1,2,3,4-tetrahydroisoquinoline-5-carboxamide and its hydrochloride (1:1)

N-[(1S,2R)-1-(3,5-difluorobenzyl)-2-hydroxy-3-({1-[3-(trifluoromethyl)phenyl]cyclopropyl}amino)propyl]-2-(2-methoxyethyl)-1-oxo-1,2,3,4-tetrahydroisoquinoline-5-carboxamide and its hydrochloride (1:1)

N-[(1S,2R)-1-(3,5-difluorobenzyl)-2-hydroxy-3-({1-[3-(tri-fluoromethyl)phenyl]cyclopropyl}amino)propyl]-2-(2-ethoxyethyl)-1-oxo-1,2,3,4-tetrahydroisoquinoline-5-carboxamide and its hydrochloride (1:1)

N-[(1S,2R)-1-(3,5-difluorobenzyl)-2-hydroxy-3-({1-[3-(tri-fluoromethyl)phenyl]cyclopropyl}amino)propyl]-7-[me-thyl(methylsulfonyl)amino]-1-oxo-2-(1-propylbutyl)-1,2,3,4-tetrahydroisoquinoline-5-carboxamide and its hydrochloride (1:1)

N-[(1S,2R)-1-(3,5-difluorobenzyl)-2-hydroxy-3-({1-[3-(tri-fluoromethyl)phenyl]cyclopropyl}amino)propyl]-2-[1-(4-fluorophenyl)ethyl]-1-oxo-1,2,3,4-tetrahydroisoquino-line-5-carboxamide and its hydrochloride (1:1)

N-[(1S,2R)-1-(3,5-difluorobenzyl)-2-hydroxy-3-({1-[3-(tri-fluoromethyl)phenyl]cyclopropyl}amino)propyl]-6-[me-thyl(methylsulfonyl)amino]-1-oxo-2-(1-propylbutyl) isoindoline-3-methyl-4-carboxamide and its hydrochloride (1:1)

N-[(1S,2R)-1-(3,5-difluorobenzyl)-2-hydroxy-3-({1-[3-(tri-fluoromethyl)phenyl]cyclopropyl}amino)propyl]-6-[me-thyl(methylsulfonyl)amino]-1-oxo-2-(1-propylbutyl) isoindoline-4-carboxamide and its hydrochloride (1:1)

N-[(1S,2R)-1-(3,5-difluorobenzyl)-2-hydroxy-3-({1-[3-(tri-fluoromethyl)phenyl]cyclopropyl}amino)propyl]-7-trif-luoromethyl-1-oxo-2-(1-propylbutyl)-1,2,3,4-tetrahy-droisoquinoline-5-carboxamide and its hydrochloride (1:1)

N-[(1S,2R)-1-(3,5-difluorobenzyl)-2-hydroxy-3-({1-[3-(tri-fluoromethyl)phenyl]cyclopropyl}amino)propyl]-7-[(me-thylsulfonyl)amino]-1-oxo-2-(1-propylbutyl)-1,2,3,4-tet-rahydroisoquinoline-5-carboxamide and its hydrochloride (1:1)

N-[(1S,2R)-1-(3,5-difluorobenzyl)-2-hydroxy-3-({1-[3-(tri-fluoromethyl)phenyl]cyclopropyl}amino)propyl]-7-(2-oxazolyl)-1-oxo-2-(1-propylbutyl)-1,2,3,4-tetrahydroiso-quinoline-5-carboxamide hydrochloride (1:1)

N-[(1S,2R)-1-(3,5-difluorobenzyl)-2-hydroxy-3-({1-[3-(tri-fluoromethyl)phenyl]cyclopropyl}amino)propyl]-7-(3-cyanophenyl)-1-oxo-2-(1-propylbutyl)-1,2,3,4-tetrahy-droisoquinoline-5-carboxamide and its hydrochloride (1:1)

N-[(1S,2R)-1-(3,5-difluorobenzyl)-2-hydroxy-3-({1-[3-(tri-fluoromethyl)phenyl]cyclopropyl}amino)propyl]-7-(2-cyanophenyl)-1-oxo-2-(1-propylbutyl)-1,2,3,4-tetrahy-droisoquinoline-5-carboxamide and its hydrochloride (1:1)

N-[(1S,2R)-1-(3,5-difluorobenzyl)-2-hydroxy-3-({1-[3-(tri-fluoromethyl)phenyl]cyclopropyl}amino)propyl]-7-me-thyl-1-oxo-2-(1-propylbutyl)-1,2,3,4-tetrahydroisoquino-line-5-carboxamide and its hydrochloride (1:1)

N-[(1S,2R)-1-(3,5-difluorobenzyl)-2-hydroxy-3-({1-[3-(tri-fluoromethyl)phenyl]cyclopropyl}amino)propyl]-7-chloro-1-oxo-2-(1-propylbutyl)-1,2,3,4-tetrahydroiso-quinoline-5-carboxamide and its hydrochloride (1:1)

N-[(1S,2R)-1-(3,5-difluorobenzyl)-2-hydroxy-3-({1-[3-(tri-fluoromethyl)phenyl]cyclopropyl}amino)propyl]-7-fluoro-1-oxo-2-(1-propylbutyl)-1,2,3,4-tetrahydroiso-quinoline-5-carboxamide and its hydrochloride (1:1).

Another subject of the invention is a method for preparing the compounds of formula (I).

In what follows, the expression "protective group Pg" is understood to mean a group which makes it possible, on the one hand, to protect a reactive functional group such as a hydroxyl or an amine during a synthesis and, on the other hand, to regenerate the reactive functional group intact at the end of the synthesis. Examples of protective groups and also of methods of protection and of deprotection are given in "Protective Groups in Organic Synthesis", Green et al., 2$^{nd}$ Edition (John Wiley & Sons, Inc., New York), 1991.

The expression "leaving group" is understood to mean, in what follows, a group which may be easily cleaved from a molecule by rupture of a heterolytic bond, with departure of an electron pair. This group may thus be easily replaced by another group during a substitution reaction for example. Such leaving groups are, for example, halogens or an activated hydroxyl group such as a methanesulfonate, benzenesulfonate, p-toluenesulfonate, triflate, acetate, etc. Examples of leaving groups and also references for the preparation thereof are given in "Advances in Organic Chemistry", J. March, 3$^{rd}$ Edition, Wiley Interscience, 1985, p. 310-316.

In the schemes which follow, the starting compounds and the reactants, when their method of preparation is not described, are commercially available or are described in the literature, or else may be prepared according to methods which are described therein or which are known to a person skilled in the art.

The abbreviations and symbols used for the description of the methods of synthesis and for the description of the compounds are the following:
 APP for polyphosphoric acid,
 BOC for tert-butoxycarboxylate,
 DCC for dicyclohexylcarbodiimide,
 DMF for dimethylformamide,
 EDCI for (1-ethyl-3,3-dimethylaminopropyl)carbodiim-ide,
 NMP for N-methyl-2-pyrrolidone,
 PyBOP for benzotriazol-1-yloxytripyrrolidinophospho-nium hexafluorophosphate,
 THF for tetrahydrofuran.

In accordance with the invention, it is possible to prepare the compounds of general formula (I) according to the method illustrated by scheme 1 below.

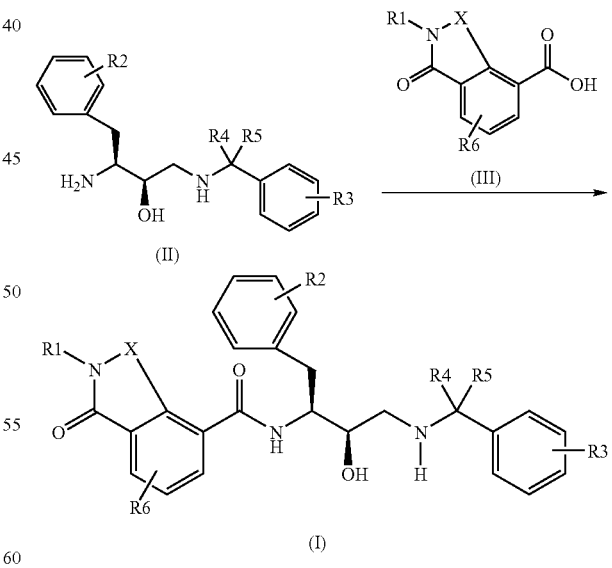

According to scheme 1, the compound of general formula (I) may be prepared by condensation of the amine functional group of the compound of general formula (II), in which R2, R3, R4 and R5 are as defined in the general formula (I), with the carboxylic acid functional group of the compound of general formula (III), in which R1 and R6 are as defined in the general formula (I). This reaction is carried out in an anhydrous medium that is preferably inert (nitrogen or argon for example) and by using conventional agents for coupling an acid functional group with an amine functional group such as DCC, PyBOP or EDAC, in solvents such as dichloromethane, THF, ether or chloroform at a temperature between 20° C. and the reflux temperature of the solvent.

The compound of general formula (II), in which R2, R3, R4 and R5 are as defined in the general formula (I), may be prepared from the compound of general formula (IV), in which R2, R3, R4 and R5 are as defined in the general formula (I), by deprotection of the primary amine by action of an acid (for example hydrochloric acid) in solution in a solvent or a solvent mixture that is etherated (for example diethyl ether) and/or chlorinated (for example dichloromethane), according to the method illustrated by scheme 2 below.

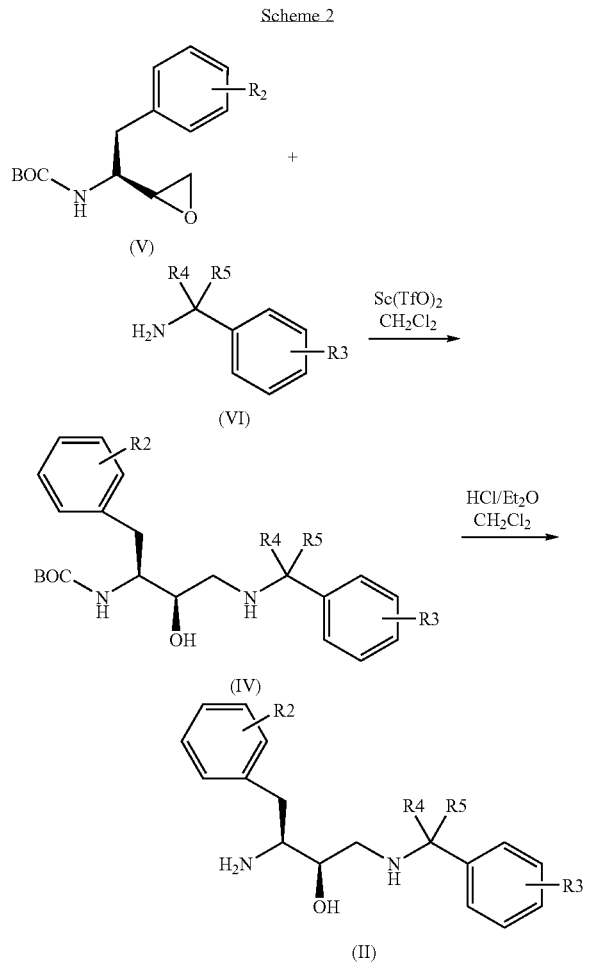

The compound of general formula (IV), in which R2, R3, R4 and R5 are as described previously, may be prepared by reacting a benzylamine derivative of general formula (VI), in which R3, R4 and R5 are as defined in the general formula (I) with an oxirane of general formula (V), in which R2 is as defined in the general formula (I) by operating in an anhydrous medium that is preferably inert (nitrogen or argon for example), in a chlorinated solvent (for example dichloromethane) and in the presence of a Lewis acid such as, for example, scandium triflate.

The compounds of general formula (IIIa) in which X represents a methylene group and R1 and R6 are as described previously may be Prepared according to the method described in scheme 3 below.

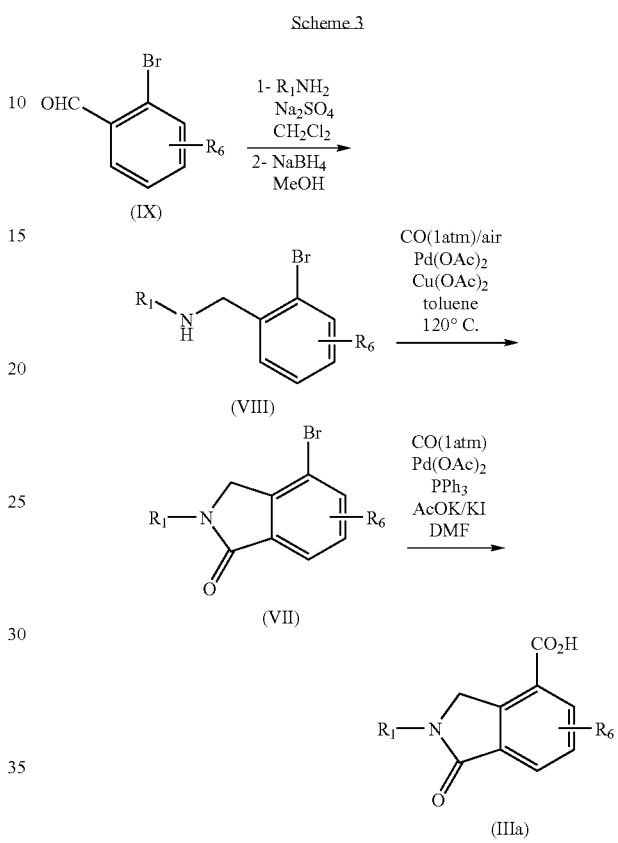

The compounds of general formula (IIIa) may be prepared from isoindolin-1-one of general formula (VII) reacted with carbon monoxide in the presence of (potassium or sodium) acetate ions, an alkali metal iodide (sodium iodide or potassium iodide for example), a palladium catalyst (palladium acetate for example), a phosphine (triphenylphosphine for example) in solution in an organic solvent (dimethylformamide or dimethylsulfoxide for example) and in the presence of water. The reaction takes place under a carbon monoxide pressure of 1 to 100 atmospheres and at a temperature between 20° C. and 120° C., by analogy with the works of D. Milstein et al. (J. Am. Chem. Soc. (1989) 8742) and T. W. Ku et al. (Tetrahedron Lett. (1997) 3131).

The isoindolin-1-one of general formula (VII) may be prepared from the halogenated derivative of general formula (VIII), in which R1 and R6 are as defined previously, by the action of a mixture of carbon monoxide and air under atmospheric pressure. The reaction takes place, by analogy with the works of K. Orito et al. J. Am. Chem. Soc. (2004) 14342, in solution in an organic solvent (for example toluene) in the presence of salts of palladium(II) and of copper(II) (for example palladium acetate and copper acetate) and at a temperature between 20° C. and the reflux temperature of the solvent.

The halogenated compound of general formula (VIII) may be prepared from a bromobenzaldehyde of general formula (IX) reacted with an amine of general formula R1-NH$_2$ in the presence or absence of a dehydrating agent (magnesium sulfate, sodium sulfate, molecular sieves, for example) by operating in an anhydrous medium that is preferably inert (nitrogen or argon for example), in a chlorinated organic solvent (dichloromethane for example), at a temperature between 0° C. and the reflux temperature of the solvent. The crude mixture is then subjected to the action of a reducing agent (sodium borohydride or sodium cyanoborohydride for example) in an alcoholic solvent (methanol or ethanol for example)

The compounds of general formula (IIIb), in which X represents an ethylene group, R1 and R6 are as defined in the general formula (I), may be prepared according to the method described in Scheme 4 below.

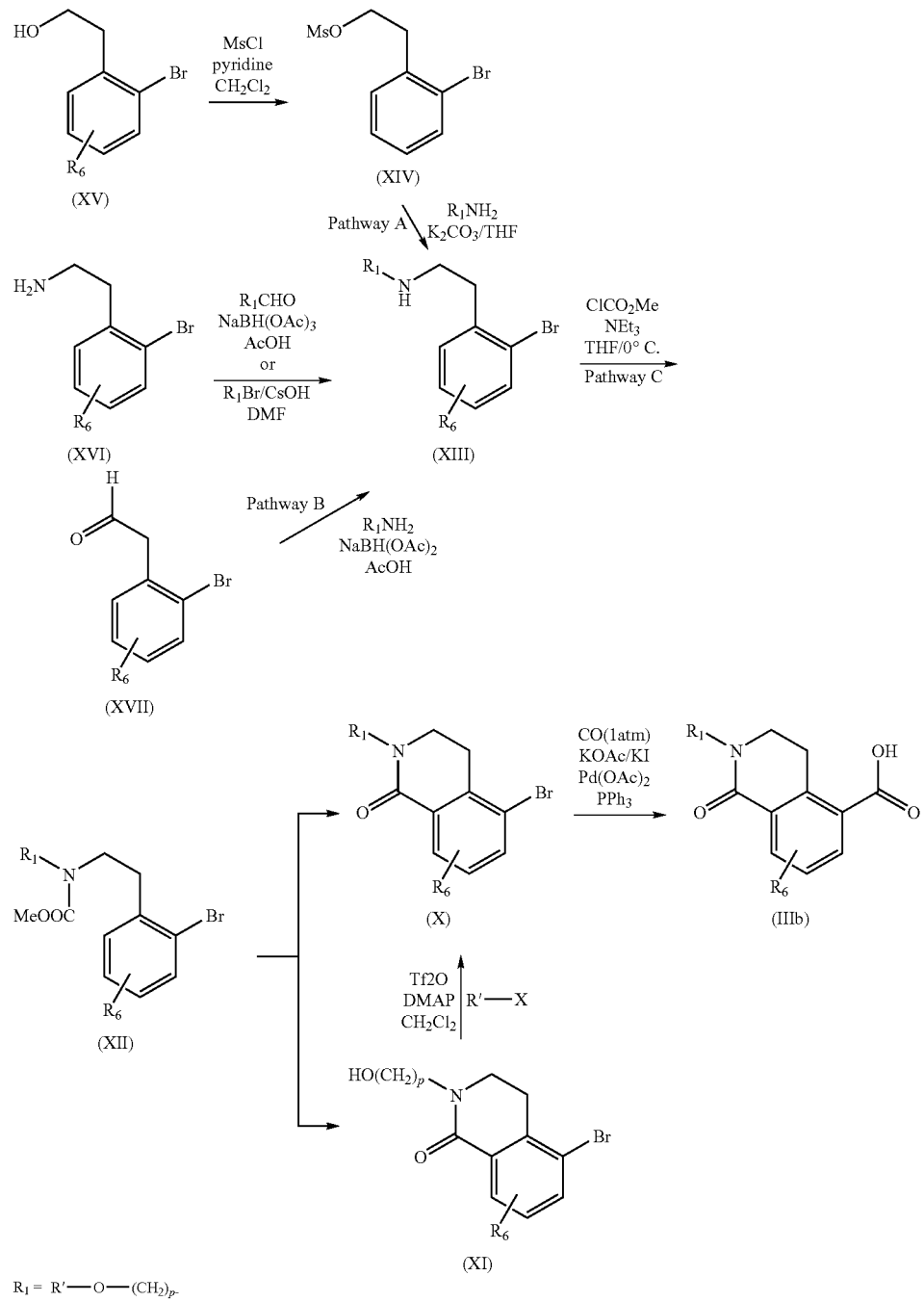

The compounds of general formula (IIIb) may be prepared from compounds of general formula (X) under the same conditions as those used for the preparation of compounds of general formula (IIIa).

The compounds of general formula (X), in which R1 is a chain that does not contain an oxygen atom, are obtained by cyclization, of the Bischler-Napieralski type, of the carbamates of general formula (XII) by means of triflic anhydride, by analogy with the works of Y-C. Wang et al. Synthesis 15 (2002) 2187-90. The reaction takes place in the presence of an organic base (4-dimethylaminopyridine for example) in solution in an organic solvent (dichloromethane for example) at a temperature between 0° C. and the reflux temperature of the solvent.

In the case of compounds of general formula (X), for which the substituent R1 is a $(C_1\text{-}C_6)$alkyl-O—$(C_1\text{-}C_6)$alkyl chain, the action of the triflic anhydride results in compounds of general formula (XI), in which p represents an integer corresponding to 1, 2, 4 or 4. These compounds of general formula (XI) are converted to compounds of general formula (X) by action of a haloalkane R'—X, in which R' represents a $(C_1\text{-}C_6)$alkyl group and X represents a halogen atom (methyl iodide or ethyl iodide for example). The reaction takes place in solution in an organic solvent (dimethylsulfoxide, acetonitrile or dimethylformamide for example) in the presence of a base (sodium hydroxide, potassium hydroxide or sodium hydride for example), at a temperature between 0° C. and the reflux temperature of the solvent.

Alternatively, the compounds of general formula (X) may be obtained as described in Scheme 5 below.

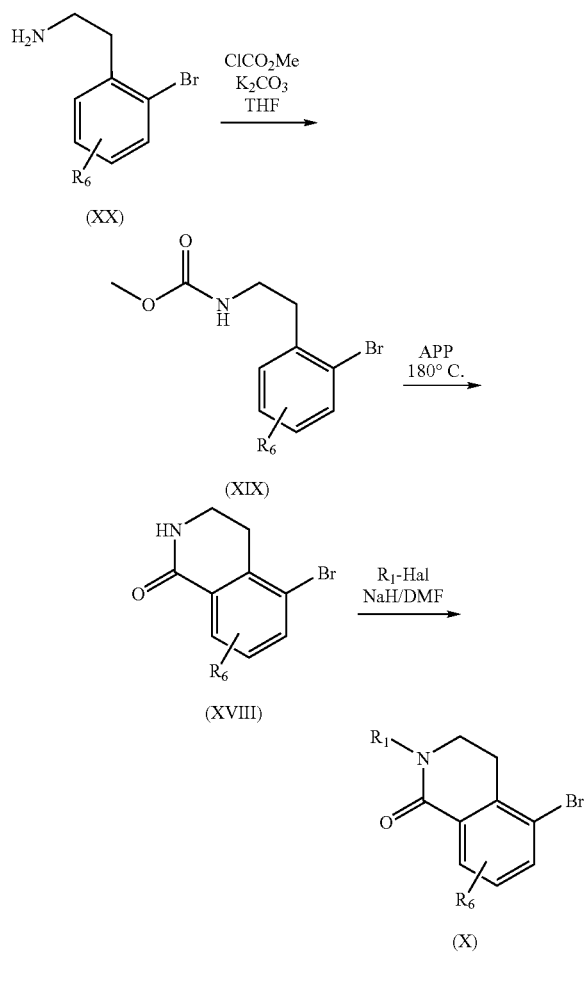

The compounds of general formula (X) may be prepared by alkylation of compounds of general formula (XVIII) (alkyl iodide or aryl iodide for example) in solution in an organic solvent (dimethylformamide, acetonitrile or dimethylsulfox- ide for example) in the presence of a base (sodium carbonate, potassium carbonate, sodium hydride, triethylamine or pyridine for example) at a temperature between 0° C. and the reflux temperature of the solvent.

The compounds of general formula (XVIII) may be prepared by cyclization of the compounds of general formula (XIX) (the cyclization agent being polyphosphoric acid for example). The reaction takes place without solvent at a temperature between 50° C. and 200° C.

The compounds of general formula (XIX) may be prepared from compounds of general formula (XX) treated by a chloroformate (methyl chloroformate as indicated in Scheme 4 or ethyl chloroformate for example). The reaction takes place in solution in an organic solvent (tetrahydrofuran or toluene for example) in the presence of an organic base (triethylamine or pyridine for example) at a temperature between 0° C. and the reflux temperature of the solvent.

The compounds of general formula (XIII) may be prepared according to pathway A, in two steps starting from a hydroxylated derivative of general formula (XV). Firstly, the alcohol (XV) is converted to a sulfonate derivative (for example a mesylate derivative as indicated in Scheme 4). The reaction takes place in the presence of a base (pyridine for example, as indicated in Scheme 4), in solution in an organic solvent (dichloromethane or dioxane for example), at a temperature between 0° C. and the reflux temperature of the solvent. Secondly, the intermediate (XIV) is reacted with a primary amine of general formula $R1\text{-}NH_2$. The reaction takes place in solution in an organic solvent (tetrahydrofuran, acetonitrile or dimethylformamide for example) in the presence of a base (sodium carbonate or potassium carbonate for example) at a temperature between 0° C. and the reflux temperature of the solvent.

Alternatively, according to pathway B of Scheme 4, the compounds of general formula (XIII) may also be obtained by reaction of an amine of general formula (XVI) with an aldehyde. The reaction may be carried out in an acid solvent (acetic acid for example) in the presence of a reducing agent (sodium borohydride or cyanoborohydride for example) at a temperature between 0° C. and 100° C.

Alternatively again, according to pathway C, the compounds of general formula (XIII) may also be prepared by reaction of an amine of general formula $R1\text{-}NH_2$ in the presence of a reducing agent (sodium borohydride or sodium triacetoxy borohydride for example) in solution in a carboxylic acid (acetic acid for example). The reaction is preferably carried out under an inert atmosphere (argon or nitrogen for example) at a temperature between 0° C. and the reflux temperature of the solvent.

The compounds of general formula (IIIc), in which X represents an ethylene group, R1 is as described previously and R6 is an $NR7SO_2R8$ group, may be prepared according to the process described in Scheme 6 below.

Scheme 6

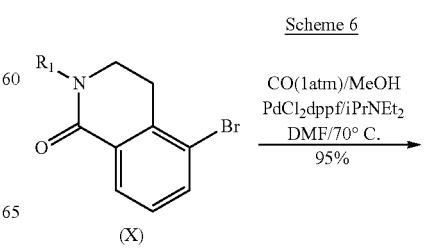

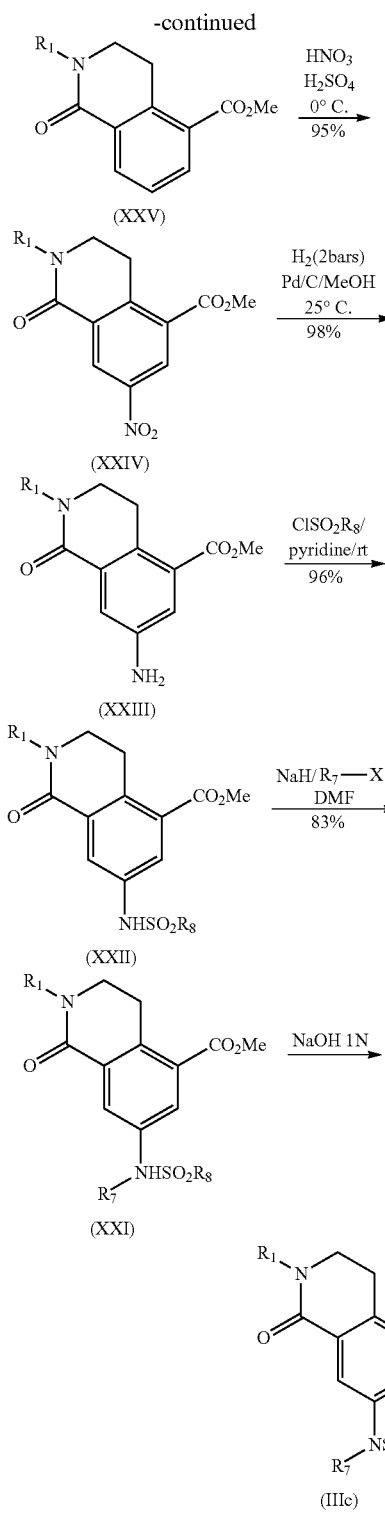

The compounds of general formula (IIIc), in which R1, R7 and R8 are as defined previously, may be prepared by action of an aqueous solution of base (alkali metal hydroxide or potassium carbonate for example) on compounds of general formula (XXI) in solution in an organic solvent (dioxane or methanol for example). The reaction preferably takes place at a temperature between 0° C. and 100° C.

The compounds of general formula (XXI), in which R1, R7 and R8 are as defined previously, may be prepared by action of an alkyl halide of general formula R7-X, X representing a halogen atom, on compounds of general formula (XXII) in solution in an organic solvent (dimethylformamide, acetonitrile or N-methylpyrrolidine for example) in the presence of a base (sodium hydride for example). The reaction preferably takes place under an inert atmosphere (nitrogen or argon for example), at a temperature between 0° C. and 100° C.

The compounds of general formula (XXII), in which R1, R7 and R8 are as defined previously, may be prepared by action of a sulfonyl chloride of general formula R8-SO$_2$Cl on compounds of general formula (XXIII) in solution in a chlorinated organic solvent (dichloromethane or chloroform for example) in the presence of a base (triethylamine or pyridine for example). The reaction preferably takes place under an inert atmosphere (nitrogen or argon for example) at a temperature between 0° C. and 100° C.

The compounds of general formula (XXIII) may be prepared by action of a reducing agent (gaseous hydrogen under a pressure of 1 to 10 atmospheres and in the presence of a catalyst such as palladium for example) on compounds of general formula (XXIV) in solution in an alcoholic solvent (methanol or ethanol for example). The reaction preferably takes place at a temperature between 0° C. and 50° C.

The compounds of general formula (XXIV) may be prepared by action of concentrated nitric acid on compounds of general formula (XXV) in solution in concentrated sulfuric acid. The reaction preferably takes place under an inert atmosphere (nitrogen or argon) at a temperature between −10° C. and 20° C.

The compounds of general formula (XXV) may be prepared by reaction of compounds of general formula (X) with carbon monoxide in the presence of an alcohol, methanol for example, and a palladium-based catalyst, [1,1'-bis(diphenylphosphino)ferrocene]dichloropalladium for example. The reaction takes place under a carbon monoxide pressure of 1 to 100 atmospheres and at a temperature between 20° C. and 120° C., by analogy with the works of J. R. Scheffer et al. (Synthesis (2001) 1253).

The esters of general formula (XXI) may also be used to prepare the compounds of general formula (I) after condensation with the amine functional group of general formula (II).

The compounds of formula (IIIa), (IIIb) and (IIIc) are useful as synthesis intermediates of the compounds of formula (I).

The products of formula (I) may be subjected, if desired and if necessary, in order to obtain products of formula (I) or to be converted into other products of formula (I), to one or more of the following conversion reactions, in any order:

a) an esterification or amidification reaction of an acid functional group;
b) a hydrolysis reaction of an ester functional group to an acid functional group;
c) a reaction for conversion of a hydroxyl functional group to an alkoxy functional group;
d) an oxidation reaction of an alcohol functional group to an aldehyde, ketone or acid functional group;
e) a reduction reaction of an acid, aldehyde or ketone functional group to an alcohol functional group;
f) a reductive amination reaction of an aldehyde or ketone functional group;
g) an oxidation reaction of an alkenyl group to an aldehyde or ketone functional group;
h) an oxidation reaction of a thioether to a sulfone or sulfoxide;
i) an alkylation reaction of a sulfonamide;

j) a dehydration reaction of a hydroxyalkyl group to an alkenyl group;
k) a dehydrohalogenation reaction of a halogenated derivative;
l) a total or partial hydrogenation reaction of an alkenyl or alkynyl group to an alkenyl or alkyl group;
m) a catalytic coupling reaction of a halogenated derivative and of an organometallic derivative such as a stannic or boronic derivative in order to introduce an alkyl, alkenyl, alkynyl or aryl substituent;
n) a reaction for protecting reactive functional groups;
o) a reaction for eliminating protective groups that the protected reactive functional groups may bear;
p) a salification reaction by a mineral or organic acid or by a base in order to obtain the corresponding salt;
q) a reaction for resolution of racemic forms into enantiomers, said products of formula (I) thus obtained being, where appropriate, in all the possible racemic, enantiomeric and diastereoisomeric isomer forms;
r) a reduction reaction of nitro derivatives to nitroso or amino derivatives;
s) a monoalkylation or dialkylation reaction of an amine functional group;
t) a sulfonylation reaction of a primary or secondary amine; and
u) an acylation reaction of an amine functional group.

Another subject of the invention is, according to another of its aspects, the compounds of formulae (IIIa), (IIIb) and (IIIc). These compounds are useful as synthesis intermediates of the compounds of formula (I).

The compounds of formula (I) may be purified by methods known to a person skilled in the art, for example by crystallization, chromatography or extraction.

In schemes 1 to 6 the starting compounds and the reactants, when their method of preparation is not described, are commercially available or are described in the literature, or else may be prepared according to methods which are described therein or which are known to a person skilled in the art.

The following examples describe the preparation of certain compounds in accordance with the invention. These examples are not limiting and serve only to illustrate the present invention. The numbers of the compounds exemplified refer to those given in the table below, which illustrates the chemical structures and the physical properties of a few compounds according to the invention.

The proton nuclear magnetic resonance ($^1$H NMR) spectra were performed at 250 MHz, 300 MHz, 400 MHz or 500 MHz on Brüker machines (chemical shifts ($\delta$ in ppm)—in the solvent dimethylsulfoxide—$d_6$ (DMSO-$d_6$) referenced to 2.50 ppm at the temperature of 303K). The abbreviations used for characterizing the signals are the following: s=singlet, m=multiplet, d=doublet, t=triplet, q=quadruplet.

The nomenclature of the exemplified compounds below was established using ACDLabs® Version 10.0 software.

EXAMPLE 1

1.1: Base N-[(1S,2R)-1-benzyl-2-hydroxy-3-{[3-(trifluoromethyl)benzyl]amino}propyl]-1-oxo-2-(1-propylbutyl)isoindoline-4-carboxamide 1.1.1: N-(2-Bromobenzyl)heptan-4-amine Added to a solution of 7.4 g of 2-bromobenzaldehyde in 80 cm$^3$ of dichloromethane are 6.25 g of sodium sulfate and 5.07 g of 4-aminoheptane at a temperature close to 20° C. After stirring for 2 h, the reaction mixture is filtered through a cartridge and washed with 2 lots of 10 cm$^3$ of dichloromethane. The filtrate is concentrated using a rotary evaporator under reduced pressure (5 kPa). The oil obtained is dissolved in 80 cm$^3$ of methanol. 0.757 g of sodium borohydride is added in 3 lots. The reaction mixture is stirred for 1 h at 20° C., then 0.757 g of sodium borohydride is again added. This operation is carried out twice. After stirring at 20° C. for 20 h, the reaction mixture is concentrated using a rotary evaporator under reduced pressure (5 kPa). The concentration residue is taken up in 100 cm$^3$ of dichloromethane and 50 cm$^3$ of water. The organic phase is washed with 2 lots of 50 cm$^3$ of a saturated aqueous solution of sodium chloride, dried over magnesium sulfate and concentrated using a rotary evaporator under reduced pressure (5 kPa). The 10.8 g of colorless oil obtained are purified by filtration through a pellet of 150 g of silica with 1 dm$^3$ of an 80% heptane/20% ethyl acetate mixture. After concentrating the fractions under reduced pressure, 9.75 g of N-(2-bromobenzyl)heptan-4-amine are obtained in the form of a colorless clear oil.

NMR: 0.84 (t, J=7.0 Hz, 6 H) 1.21-1.43 (m, 8 H) 1.74 (broad s, 1 H) 2.43 (m, 1 H) 3.73 (s, 2 H) 7.17 (td, J=7.7, 1.8 Hz, 1 H) 7.35 (td, J=7.7, 1.8 Hz, 1 H) 7.53 (dd, J=7.7, 1.8 Hz, 1 H) 7.56 (dd, J=7.7, 1.8 Hz, 1 H)

MS-EI: 283$^{(+)}$ ($^{79}$Br)=M$^{(+)}$; 240$^{(+)}$ ($^{79}$Br)=[283$^{(+)}$-C$_3$H$_9$]
MS-Cl (NH$_3$): 284$^{(+)}$ ($^{79}$Br)=(M+H)$^{(+)}$ 1.1.2: 4-Bromo-2-(1-propylbutyl)isoindolin-1-one Introduced into a three-necked flask that is stirred and purged using carbon monoxide are 2 g of N-(2-bromobenzyl)heptan-4-amine in 70 cm$^3$ of toluene at a temperature close to 20° C. 0.639 g of copper acetate and 79 mg of palladium acetate are added to this solution. Carbon monoxide bubbling is applied and also dry air bubbling. The reaction mixture is heated under the reflux of the solvent for 9 h 30 min. The reaction mixture is cooled, filtered over a Celite 545 pellet, then washed with 2 lots of 10 cm$^3$ of ethyl acetate. The filtrate is concentrated using a rotary evaporator under reduced pressure (5 kPa). The 3 g of green oil obtained are purified by flash chromatography over silica (column: 200 g; particle size: 15-40 µm; flow rate: 20 cm$^3$/min; eluent: 90% heptane/10% ethyl acetate to 100% ethyl acetate gradient over 150 min). After concentrating the fractions under reduced pressure, 800 mg of 4-bromo-2-(1-propylbutyl)isoindolin-1-one are obtained in the form of a colorless oil.

NMR: 0.86 (t, J=7.4 Hz, 6 H) 1.07-1.24 (m, 4 H) 1.43-1.76 (m, 4 H) 4.17-4.31 (m, 3 H) 7.47 (t, J=7.7 Hz, 1 H) 7.69 (d, J=7.7 Hz, 1 H) 7.81 (d, J=7.7 Hz, 1 H)

MS-EI: 309$^{(+)}$ ($^{79}$Br)=M$^{(+)}$ 1.1.3: 1-Oxo-2-(1-propylbutyl)isoindoline-4-carboxylic acid Introduced successively, at a temperature close to 20° C., into a three-necked flask that is stirred and purged using carbon monoxide are 400 mg of 4-bromo-2-(1-propylbutyl)isoindolin-1-one, 10 cm$^3$ of dimethylformamide, 0.6 cm$^3$ of water, 0.481 g of potassium acetate, 214 mg of potassium iodide, 29 mg of palladium acetate and 68 mg of triphenylphosphine. The reaction mixture is subjected to a carbon monoxide bubbling, then is heated at 100° C. for 6 h. The reaction mixture is concentrated using a rotary evaporator under reduced pressure (5 kPa). The beige solid obtained is taken up in 7.5 cm$^3$ of 1M sodium hydroxide, 2 g of ice and 30 cm$^3$ of ethyl acetate. After decantation, the aqueous phase is washed with 20 cm$^3$ of ethyl acetate. It is then acidified, while stirring, with 1.5 cm³ of a 5M hydrochloric acid solution (pH=4), then extracted with 30 cm³ of ethyl acetate. The organic phase is washed with 5 cm³ of water, then 5 cm³ of a saturated aqueous solution of sodium chloride, dried over magnesium sulfate and concentrated using a rotary evaporator under reduced pressure (5 kPa). The 295 mg of beige solid obtained are triturated in 15 cm³ of diisopropyl ether, filtered and dried under vacuum. 264 mg of 1-oxo-2-(1-propylbutyl) isoindoline-4-carboxylic acid are obtained in the form of a white solid.

NMR: 0.86 (t, J=7.4 Hz, 6 H) 1.10-1.24 (m, 4 H) 1.46-1.74 (m, 4 H) 4.26 (m, 1 H) 4.54 (s, 2 H), 7.64 (t, J=7.7 Hz, 1 H) 7.90 (d, J=7.7 Hz, 1 H) 8.12 (d, J=7.7 Hz, 1 H), 13.41 (m, 1 H)
MS-EI: 275$^{(+)}$=M$^{(+)}$; 232$^{(+)}$=M$^{(+)}$-C$_3$H$_7$

1.1.4: N-[(1S,2R)-1-Benzyl-2-hydroxy-3-{[3-(trifluoromethyl)benzyl]amino}propyl]-1-oxo-2-(1-propylbutyl)isoindoline-4-carboxamide 136.4 mg of 1-oxo-2-(1-propylbutyl)isoindoline-4-carboxylic acid are dissolved in 8 cm³ of dichloromethane under an inert atmosphere at a temperature close to 20° C. 195 mg of ((2R,3S)-3-amino-4-phenyl-1-{[3-(trifluoromethyl)benzyl]amino}butan-2-ol hydrochloride (2:1), 9.6 mg of 1-hydroxybenzotriazole, and 108.7 mg of 1-(3-dimethylaminopropyl)-3-ethylcarbodiimide hydrochloride are added to the solution. 0.308 cm³ of N,N-diisopropylethylamine is poured into the reaction medium. This is kept stirring for 20 h at 20° C. 10 cm³ of water are added to the reaction medium. The organic phase is washed with 10 cm³ of a saturated aqueous solution of sodium chloride, dried over magnesium sulfate and concentrated using a rotary evaporator under reduced pressure (5 kPa). The 310 mg of beige gum obtained are purified by flash chromatography over silica (column: 15 g; particle size: 20-40 μm, spherical; flow rate: 20 cm³/min; eluent: 95% dichloromethane/5% methanol). After concentrating the fractions under reduced pressure, 110 mg of N-[(1S,2R)-1-benzyl-2-hydroxy-3-{[3-(trifluoromethyl)benzyl]amino}propyl]-1-oxo-2-(1-propylbutyl)isoindoline-4-carboxamide are obtained in the form of a beige foam.

1.2: Salt N-[(1S,2R)-1-benzyl-2-hydroxy-3-{[3-(trifluoromethyl)benzyl]amino}propyl]-1-oxo-2-(1-propylbutyl)isoindoline-4-carboxamide hydrochloride (1:1)

110 mg of N-[(1S,2R)-1-benzyl-2-hydroxy-3-{[3-(trifluoromethyl)benzyl]amino}propyl]-1-oxo-2-(1-propylbutyl) isoindoline-4-carboxamide are dissolved in 8 cm³ of ether at a temperature close to 20° C. 0.5 cm³ of a 4M solution of hydrochloric acid in dioxane is added while stirring under argon. The reaction mixture precipitates. The precipitate is filtered under a slight vacuum, washed with 2 lots of 5 cm³ of ethyl ether then dried in a dessicator for 2 h. 80 mg of N-[(1S,2R)-1-benzyl-2-hydroxy-3-{[3-(trifluoromethyl)benzyl]amino}propyl]-1-oxo-2-(1-propylbutyl)isoindoline-4-carboxamide hydrochloride (1:1) is obtained in the form of a white solid.

NMR: 0.83 (t, J=7.5 Hz, 3 H); 0.86 (t, J=7.5 Hz, 3 H); from 1.03 to 1.20 (m, 4 H); 1.51 (m, 4 H); 2.81 (m, 1 H); 2.92 (m, 1 H); 3.18 (m, 2 H); 3.96 (m, 1 H); from 4.09 to 4.25 (m, 4 H); 4.31 (m, 2 H); 5.95 (broad m, 1 H); 7.13 (m, 1 H); 7.23 (m, 4 H); 7.57 (t, J=7.5 Hz, 1 H) 7.64 (t, J=7.5 Hz, 1 H); from 7.73 to 7.88 (m, 4 H); 7.97 (broad s, 1 H); 8.53 (d, J=9.0 Hz, 1 H); 9.00 (broad s, 1 H); 9.34 (broad s, 1 H)
MS-EI: 595$^{(+)}$=M$^{(+)}$; 552$^{(+)}$=M$^{(+)}$-C$_3$H$_7$ .

EXAMPLE 2

2.1: Base N-[(1S,2R)-1-benzyl-2-hydroxy-3-({1-[3-(trifluoromethyl)phenyl]cyclopropyl}amino)propyl]-1-oxo-2-(1-propylbutyl)-1,2,3,4-tetrahydroisoquinoline-5-carboxamide

2.1.1: N-[2-(2-Bromophenyl)ethyl]heptan-4-amine 10 g of 2-bromophenethylamine and 5.71 g of 4-heptanone are dissolved in 250 cm³ of 1,2-dichloroethane at a temperature close to 20° C. 14.84 g of sodium triacetoxyborohydride and 2.9 cm³ of glacial acetic acid are added to the reaction medium. Stirring is continued for 20 h. 300 cm³ of 1M sodium hydroxide are added to the reaction medium. The aqueous phase is extracted with 3 lots of 100 cm³ of ethyl acetate. The organic phases are combined and washed with 4 lots of 100 cm³ of water then 100 cm³ of a saturated aqueous solution of sodium chloride, dried over magnesium sulfate, and concentrated using a rotary evaporator under reduced pressure (5 kPa). The yellow liquid obtained is purified by flash chromatography over silica (column: 400 g; particle size: 20-40 μm, spherical; flow rate: 30 cm³/min; eluent: 100% heptane to 70% ethyl acetate/30% heptane gradient). After concentrating the fractions under reduced pressure, 17.33 g of N-[2-(2-bromophenyl)ethyl]heptan-4-amine are obtained.

LC-MS-DAD-ELSD: 298$^{(+)}$($^{79}$Br)=(M+H)$^{(+)}$

2.1.2: Methyl[2-(2-bromophenyl)ethyl](1-propylbutyl)carbamate 5.85 g of N-[2-(2-bromophenyl)ethyl]heptan-4-amine in solution in 60 cm³ of anhydrous tetrahydrofuran are stirred under an inert atmosphere at 0° C. 2.76 cm³ of triethylamine are added to the reaction mixture, then 1.52 cm³ of methyl chloroformate are introduced over 10 min using a syringe. The reaction mixture is kept stirring for 1 h at 0° C., then 3 h at 20° C. 20 cm³ of a saturated aqueous solution of ammonium chloride are added, then 100 cm³ of ethyl acetate. The organic phase is washed with 4 lots of 30 cm³ of water, then 30 cm³ of a saturated aqueous solution of sodium chloride, dried over magnesium sulfate, filtered through a pellet (30 g) of silica (particle size: 40-63 μm), rinsed with 50 cm³ of ethyl acetate and concentrated using a rotary evaporator under reduced pressure (5 kPa). 6.4 g of methyl[2-(2-bromophenyl)ethyl](1-propylbutyl)carbamate are obtained in the form of a colorless oil.

NMR: 0.85 (t, J=7.4 Hz, 6 H) 1.12-1.25 (m, 4 H) 1.28-1.54 (m, 4 H) 2.92 (m, 2 H) 3.14 (m, 2 H) 3.62 (s, 1 H) 3.64 (s, 2 H) 3.86 (broad m, 0.34 H) 3.98 (broad m, 0.66 H) 7.18 (m, 1 H) 7.25-7.40 (m, 2 H) 7.60 (d, J=7.7 Hz, 1 H)
LC-MS-DAD-ELSD: 356$^{(+)}$($^{79}$Br)=(M+H)$^{(+)}$

2.1.3: 5-Bromo-2-(1-propylbutyl)-3,4-dihydroisoquinolin-1(2H)-one 5.8 g of methyl[2-(2-bromophenyl)ethyl](1-propylbutyl) carbamate are dissolved, under an inert atmosphere, in 250 cm³ of dichloromethane, at a temperature close to 20° C. 5.43 g of 4-dimethylaminopyridine are added to the reaction mixture. This is cooled to a temperature close to 0° C. 13 cm³ of trifluoromethanesulfonic anhydride in solution in 250 cm³ of anhydrous dichloromethane are poured into the reaction mixture over 45 min. The suspension is kept stirring for 20 h at a temperature close to 20° C. 300 cm³ of a saturated aqueous solution of sodium carbonate are added to the reaction mixture. The stirring is continued for 30 min. The organic phase is washed with 100 cm³ of a 20% aqueous solution of acetic acid, 100 cm³ of a saturated aqueous solution of sodium carbonate, and 100 cm³ of a saturated aqueous solution of sodium chloride, dried over magnesium sulfate, filtered through a pellet (50 g) of silica (particle size: 40-63 µm), rinsed with 500 cm³ of dichloromethane and concentrated using a rotary evaporator under reduced pressure (5 kPa). 4.63 g of 5-bromo-2-(1-propylbutyl)-3,4-dihydroisoquinolin-1 (2H)-one are obtained in the form of a yellow oil.

NMR: 0.86 (t, J=7.3 Hz, 6 H) 1.12-1.30 (m, 4 H) 1.41 (m, 2 H) 1.51 (m, 2 H) 2.96 (t, J=6.6 Hz, 2 H) 3.36 (t, J=6.6 Hz, 2 H) 4.64 (m, 1 H) 7.31 (t, J=7.9 Hz, 1 H) 7.76 (dd, J=7.9, 1.0 Hz, 1 H) 7.91 (dd, J=7.9, 1.0 Hz, 1 H)

LC-MS-DAD-ELSD: $324^{(+)}(^{79}Br)=(M+H)^{(+)}$

2.1.4: 1-Oxo-2-(1-propylbutyl)-1,2,3,4-tetrahydroisoquinoline-5-carboxylic acid Introduced successively, at a temperature close to 20° C., into a three-necked flask that is stirred and purged with carbon monoxide are 350 mg of 5-bromo-2-(1-propylbutyl)-3,4-dihydroisoquinolin-1(2H)-one, 15 cm³ of dimethylformamide, 1.5 cm³ of water, 0.4 g of potassium acetate, 36 mg of potassium iodide, 97 mg of palladium acetate and 227 mg of triphenylphosphine. The reaction mixture is subjected to a carbon monoxide bubbling, then is heated to 100° C. for 5 h 30 min. The reaction mixture is kept at 100° C. for 20 h, then cooled to 25° C. in order to be filtered through a 45 µm Millipore membrane. The residue is washed with 2 lots of 5 cm³ of dimethylformamide and 2 lots of 5 cm³ of ethyl acetate. The filtrate is concentrated using a rotary evaporator under reduced pressure (5 kPa). The oily residue obtained is taken up in 15 cm³ of a water/ice mixture and 20 cm³ of ethyl acetate. The pH is alkanized with 5M sodium hydroxide (pH>10). After decanting the filtrate, the aqueous phase is washed with 3 lots of 20 cm³ of ethyl acetate. It is then acidified, while stirring, with a 5M hydrochloric acid solution (pH=1), then extracted with 3 lots of 20 cm³ of ethyl acetate. The organic phases are concentrated, then washed with 10 cm³ of a saturated aqueous solution of sodium chloride, dried over magnesium sulfate and concentrated using a rotary evaporator under reduced pressure (5 kPa). 125 mg of 1-oxo-2-(1-propylbutyl)-1,2,3,4-tetrahydroisoquinoline-5-carboxylic acid are obtained in the form of a clear yellow oil.

NMR: 0.87 (t, J=7.3 Hz, 6 H) 1.12-1.31 (m, 4 H) 1.40 (m, 2 H) 1.52 (m, 2 H) 3.17-3.42 (partially masked m, 4 H) 4.66 (m, 1 H) 7.44 (t, J=7.8 Hz, 1 H) 7.97 (dd, J=7.8, 1.2 Hz, 1 H) 8.10 (dd, J=7.8, 1.2 Hz, 1 H) 12.56 (broad unresolved m, 1 H)

LC-MS-DAD-ELSD: $290^{(+)}=(M+H)^{(+)}$

The (2R,3S)-3-amino-4-phenyl-1-({1-[3-(trifluoromethyl)phenyl]cyclopropyl}amino)butan-2-ol hydrochloride (2:1), used in step 2.1.5, is prepared as follows.

The preparation of 1-(3-trifluoromethylphenyl)cyclopropylamine is described in the literature (Armin de Meijere et al., Organic Letters 2003, 5(5), 753-755).

4.6 g of 1-(3-trifluoromethylphenyl)cyclopropylamine are dissolved in 12 cm³ of dichloromethane at a temperature close to 20° C. 7.9 g of tert-butyl [S—(R,R)]-(−)-1-oxiranyl-2-phenylethyl)carbamate and 2.3 g of scandium triflate are added. The reaction mixture is kept stirring at 20° C. for 12 h. It is then diluted with 100 cm³ of dichloromethane and washed successively with two lots of 15 cm³ of water, 20 cm³ of a saturated aqueous solution of sodium hydrogen carbonate and with 50 cm³ of a saturated aqueous solution of sodium chloride. The aqueous phases are extracted using dichloromethane, and the organic phases are combined, dried over a phase separator filter and concentrated using a rotary evaporator under reduced pressure (5 kPa). The white solid obtained is purified by flash chromatography through a silica cartridge (column: 600 g; particle size: 40-60 µm; flow rate: 80 cm³/min; eluent: 80% diisopropyl ether/20% ethyl acetate). 6.8 g of tert-butyl [(1S,2R)-1-benzyl-2-hydroxy-3-({1-[3-(trifluoromethyl)phenyl]cyclopropyl}amino)propyl] carbamate are obtained in the form of a white solid.

NMR: 7.64 (s, 1H); 7.53 (m, 3H); 7.23 (m, 2H); 7.15 (m, 3H); 6.56 (d, 1H); 6.12 (d, 1H); 4.70 (d, 1H); 3.51 (m, 1H); 3.38 (m, 1H); 3.18 (m, 1H); 2.98 (dd, 1H); 2.50 (m, 2H); 1.21 (s, 9H); 0.98 (m, 4H)

LC-MS-DAD-ELSD: $465^{(+)}=(M+H)^{(+)}$

MP: 124° C.

6.8 g of tert-butyl [(1S,2R)-1-benzyl-2-hydroxy-3-({1-[3-(trifluoromethyl)phenyl]cyclopropyl}amino)propyl]carbamate are then dissolved in 250 cm³ of dichloromethane at a temperature close to 20° C. 36.6 cm³ of a 4M solution of hydrochloric acid in dioxane are added. The reaction mixture is kept stirring for 1 h 30 min at a temperature close to 20° C. The reaction mixture is concentrated using a rotary evaporator under reduced pressure (5 kPa). The beige solid obtained is triturated in diisopropyl ether then filtered. 5.4 g of (2R, 3S)-3-amino-4-phenyl-1-({1-[3-(trifluoromethyl)phenyl] cyclopropyl}amino)butan-2-ol hydrochloride (2:1) are obtained.

NMR: 1.16 (m, 1H); 1.27 (m, 1H); 1.60 (m, 2H); 2.62 (m, 1H); 2.85 (d, J=7.0 Hz, 2H); 2.95 (m, 1H); 3.52 (m, 1H); 4.15 (m, 1H); 6.17 (m, 1H); 7.24 (m, 5H); 7.65 (t, J=7.5 Hz, 1H); 7.77 (d, J=7.5 Hz, 1H); 7.81 (d, J=7.5 Hz, 1H); 7.94 (s, 1H); 8.23 (broad m, 3H); 9.72 (broad unresolved m, 1H); 10.35 (broad unresolved m, 1H).

LC-MS-DAD-ELSD: $409^{(-)}=(M+formic\ acid-H)^{(-)}$; $365^{(+)}=(M^+)$

2.1.5: N-[(1S,2R)-1-Benzyl-2-hydroxy-3-({1-[3-(trifluoromethyl)phenyl]cyclopropyl}amino)propyl]-1-oxo-2-(1-propylbutyl)-1,2,3,4-tetrahydroisoquinoline-5-carboxamide Poured into a suspension of 125 mg of 1-oxo-2-(1-propylbutyl)-1,2,3,4-tetrahydroisoquinoline-5-carboxylic acid, 170 mg of (2R,3S)-3-amino-4-phenyl-1-({1-[3-(trifluoromethyl)phenyl]cyclopropyl}amino)butan-2-ol hydrochloride (2:1), 9 mg of hydroxybenzotriazole and 104 mg of 1-(3-dimethylaminopropyl)-3-ethylcarbodiimide hydrochloride in 15 cm³ of dichloromethane is 0.444 cm³ of N,N-diisopropylethylamine at a temperature close to 20° C. The solution is kept stirring for 24 h. 15 cm³ of dichloromethane and 15 cm³ of water are added to the reaction medium. The aqueous phase is extracted with 15 cm³ of dichloromethane. The organic phases are combined, washed with 10 cm³ of a saturated aqueous solution of sodium chloride, dried over magnesium sulfate and concentrated using a rotary evaporator under reduced pressure (5 kPa). The 350 mg of oil obtained are purified by flash chromatography over silica (column: 50 g; particle size: 120-40 µm, spherical; eluent: 100% ethyl acetate). After concentrating the fractions under reduced pressure, 79 mg of N-[(1S,2R)-1-benzyl-2-hydroxy-3-({1-[3-(trifluoromethyl)phenyl]cyclopropyl}amino)propyl]-1-oxo-2-(1-propylbutyl)-1,2,3,4-tetrahydroisoquinoline-5-carboxamide are obtained.

NMR: 0.86 (t, J=7.3 Hz, 3 H) 0.87 (t, J=7.3 Hz, 3 H) 0.98 (m, 2 H), 1.04 (m, 2 H) 1.12-1.25 (m, 4 H) 1.32-1.55 (m, 4 H) 2.28-2.45 (m, 2 H) 2.46-2.68 (partially masked m, 3 H) 3.00 (m, 2 H) 3.13 (dd, J=13.9, 3.7 Hz, 1 H) 3.51 (broad m, 1 H)

4.11 (m, 1 H) 4.62 (m, 1 H) 4.86 (broad d, J=5.5 Hz, 1 H) 7.05 (dd, J=7.7, 1.2 Hz, 1 H) 7.11-7.34 (m, 6 H) 7.48-7.62 (m, 3 H) 7.69 (broad s, 1 H) 7.89 (dd, J=7.7, 1.2 Hz, 1 H) 8.09 (d, J=9.2 Hz, 1 H).

LC-MS-DAD-ELSD: 634$^{(-)}$=(M–H)$^{(-)}$; 636$^{(+)}$=(M+H)$^{(+)}$

2.2: Salt N-[(1S,2R)-1-benzyl-2-hydroxy-3-({1-[3-(trifluoromethyl)phenyl]cyclopropyl}amino)propyl]-1-oxo-2-(1-propylbutyl)-1,2,3,4-tetrahydroisoquinoline-5-carboxamide hydrochloride (1:1)

79 mg of N-[(1S,2R)-1-benzyl-2-hydroxy-3-({1-[3-(trifluoromethyl)phenyl]cyclopropyl}amino)propyl]-1-oxo-2-(1-propylbutyl)-1,2,3,4-tetrahydroisoquinoline-5-carboxamide are dissolved in 1.2 cm³ of ethyl ether at a temperature close to 20° C. 0.4 cm³ of a 2M hydrochloric acid solution in ethyl ether is added while stirring under argon, at a temperature of 5° C. The reaction mixture precipitates. The stirring is continued for 20 min, then is stopped in order to remove the supernatant. 5 cm³ of ethyl ether are again added. This operation is carried out twice. The last suspension is then concentrated under reduced pressure (5 kPa). 68 mg of N-[(1S,2R)-1-benzyl-2-hydroxy-3-({1-[3-(trifluoromethyl)phenyl]cyclopropyl}amino)propyl]-1-oxo-2-(1-propylbutyl)-1,2,3,4-tetrahydroisoquinoline-5-carboxamide hydrochloride (1:1) are obtained in the form of a white solid.

NMR: 0.86 (t, J=7.5 Hz, 3 H); 0.88 (t, J=7.5 Hz, 3 H); from 1.11 to 1.64 (m, 12 H); 2.31 (m, 2 H); 2.59 (dd, J=11.5 and 14.0 Hz, 1 H); 2.81 (m, 1 H); 3.02 (m, 3 H); 3.15 (dd, J=3.0 and 14.0 Hz, 1 H); 3.80 (m, 1 H); 4.11 (m, 1 H); 4.63 (m, 1 H); 5.84 (broad m, 1 H); 6.97 (d, J=7.5 Hz, 1 H); from 7.17 to 7.33 (m, 6 H); 7.68 (t, J=7.5 Hz, 1 H); 7.81 (d, J=7.5 Hz, 1 H); 7.90 (d, J=7.5 Hz, 2 H); 8.01 (s, 1 H); 8.20 (d, J=9.0 Hz, 1 H); 9.35 (broad unresolved m, 1 H); 9.70 (broad unresolved m, 1 H).

LC-MS-DAD-ELSD: 634$^{(-)}$=(M–H)$^{(-)}$; 636$^{(+)}$=(M+H)$^{(+)}$
MP: 174° C.

EXAMPLE 3

3.1: Base N-[(1S,2R)-1-(3,5-difluorobenzyl)-2-hydroxy-3-({1-[3-(trifluoromethyl)penyl]cyclopropyl}amino)propyl]-1-oxo-2-(1-propylbutyl)-1,2,3,4-tetrahydroisoquinoline-5-carboxamide The (2R,3S)-3-amino-4-(3,5-difluorophenyl)-1-({1-[3-(trifluoromethyl)phenyl]cyclopropyl}amino)butan-2-ol hydrochloride (2:1) is prepared as follows.

Added to a solution of 0.794 g of 1-(3-trifluoromethylphenyl)cyclopropylamine hydrochloride in 20 cm³ of water are 4 cm³ of 1M sodium hydroxide at a temperature close to 20° C. This solution is stirred for 15 min. 40 cm³ of dichloromethane are added and the mixture is stirred for 5 min. The aqueous phase is extracted with 30 cm³ of dichloromethane. The organic phases are combined, dried over magnesium sulfate and concentrated using a rotary evaporator under reduced pressure (5 kPa). 700 mg of 1-(3-trifluoromethylphenyl)cyclopropylamine are obtained, which are dissolved in 12 cm³ of dichloromethane. 1 g of tert-butyl [(1S)-2-(3,5-difluorophenyl)-1-oxiran-2-ylethyl]carbamate and 0.329 g of scandium triflate are added to the solution. The light orange-colored suspension is kept stirring at ambient temperature for 20 h. The reaction mixture is concentrated using a rotary evaporator under reduced pressure (5 kPa). The crude product obtained is purified by flash chromatography over silica (column: 200 g; particle size: 15-40 µm; flow rate: 50 cm³/min; eluent: 70% cyclohexane/30% ethyl acetate). After concentrating the fractions under reduced pressure, 0.87 g of tert-butyl [(1S,2R)-1-(3,5-difluorobenzyl)-2-hydroxy-3-({1-[3-(trifluoromethyl)phenyl]cyclopropyl}amino)propyl] carbamate is obtained in the form of a white solid.

NMR: 0.90-1.04 (m, 4H) 1.22 (s, 9H) 2.40 (m, 1H) 2.46-2.62 (partially masked m, 2H) 2.99 (dd, J=14.1, 3.2 Hz, 1H) 3.36 (m, 1H) 3.52 (m, 1H) 4.80 (d, J=5.9 Hz, 1H) 6.66 (d, J=9.3 Hz, 1H) 6.86 (m, 2H) 6.99 (tt, J=9.2, 2.4 Hz, 1H) 7.48-7.61 (m, 3H) 7.65 (broad s, 1H)

LC-MS-DAD-ELSD: 545(–)=(M+Formic Ac—H)(–); 501$^{(+)}$=(M+H)$^{(+)}$; 445$^{(+)}$=(M+H)$^{(+)}$-tBu+H At a temperature of 20° C., 870 mg of tert-butyl [1S,2R)-1-(3,5-difluorobenzyl)-2-hydroxy-3-({1-[3-(trifluoromethyl)phenyl]cyclopropyl}amino)propyl]carbamate are dissolved in 20 cm³ of dichloromethane. 17.38 cm³ of a 1M hydrochloric acid solution in ethyl ether are added to the reaction mixture which is kept stirring for 20 h at ambient temperature, then concentrated using a rotary evaporator under reduced pressure (5 kPa). 0.82 g of (2R,3S)-3-amino-4-(3,5-difluorophenyl)-1-({1-[3-(trifluoromethyl)phenyl]cyclopropyl}amino)butan-2-ol hydrochloride (1:1) is obtained in the form of a white solid.

NMR: 1.13-1.37 (m, 2H) 1.53-1.71 (m, 2H) 2.71 (m, 1H) 2.84 (dd, J=14.3, 8.2 Hz, 1H) 2.93 (dd, J=14.3, 5.9 Hz, 1H) 3.09 (m, 1H) 3.57 (m, 1H) 4.18 (m, 1H) 6.19 (m, 1H) 7.01-7.10 (m, 3H) 7.65 (t, J=7.8 Hz, 1H) 7.77 (d, J=7.8 Hz, 1H) 7.87 (d, J=7.8 Hz, 1H) 7.98 (s, 1H) 8.19 (s, 3H) 9.77 (m, 1H) 10.23 (m, 1H)

LC-MS-DAD-ELSD: 401$^{(+)}$=(M+H)$^{(+)}$

Poured into a suspension of 150 mg of (2R,3S)-3-amino-4-(3,5-difluorophenyl)-1-({1-[3-(trifluoromethyl)phenyl]cyclopropyl}amino)butan-2-ol hydrochloride (2:1), 101 mg of 1-oxo-2-(1-propylbutyl)-1,2,3,4-tetrahydroisoquinoline-5-carboxylic acid, 4 mg of hydroxybenzotriazole and 76 mg of 1-(3-dimethylaminopropyl)-3-ethylcarbodiimide hydrochloride in 6 cm³ of dichloromethane is 0.217 cm³ of N,N-diisopropylethylamine at a temperature close to 20° C. The solution is kept stirring for 24 h at a temperature close to 20° C. 15 cm³ of water are added to the reaction medium. The organic phase is washed with 5 cm³ of a saturated aqueous solution of sodium chloride, dried over magnesium sulfate and concentrated using a rotary evaporator under reduced pressure (5 kPa). The product obtained is purified by flash chromatography over silica (column: 15 g; particle size: 120-40 µm, spherical; flow rate: 10 cm³/min; eluent: 100% ethyl acetate). After concentrating the fractions under reduced pressure, 140 mg of N-[(1S,2R)-1-(3,5-difluorobenzyl)-2-hydroxy-3-({1-[3-(trifluoromethyl)phenyl]cyclopropyl}amino)propyl]-1-oxo-2-(1-propylbutyl)-1,2,3,4-tetrahydroisoquinoline-5-carboxamide are obtained in the form of a colorless oil.

3.2: Salt N-[(1S,2R)-1-(3,5-difluorobenzyl)-2-hydroxy-3-({1-[3-(trifluoromethyl)phenyl]cyclopropyl}amino)propyl]-1-oxo-2-(1-propylbutyl)-1,2,3,4-tetrahydroisoquinoline-5-carboxamide hydrochloride (1:1)

40 mg of N-[(1S,2R)-1-(3,5-difluorobenzyl)-2-hydroxy-3-({1-[3-(trifluoromethyl)phenyl]cyclopropyl}amino)propyl]-1-oxo-2-(1-propylbutyl)-1,2,3,4-tetrahydroisoquinoline-5-carboxamide are dissolved in 10 cm³ of ethyl ether at a temperature close to 20° C. 3 cm³ of a 1M hydrochloric acid solution in ether are added while stirring under argon. The reaction mixture precipitates. The precipitate is filtered through sintered glass, washed with 3 lots of 5 cm³ of ethyl ether then dried in a desiccator under vacuum at 35° C. for 2 h. 129 mg of N-[(1S,2R)-1-(3,5-difluorobenzyl)-2-hydroxy- 3-({1-[3-(trifluoromethyl)phenyl]cyclopropyl}amino)propyl]-1-oxo-2-(1-propylbutyl)-1,2,3,4-tetrahydroisoquinoline-5-carboxamide hydrochloride (1:1) are obtained in the form of a white solid.

NMR: for this batch, all the signals are broad with: 0.86 (t, J=7.5 Hz, 3 H); 0.87 (t, J=7.5 Hz, 3 H); from 1.05 to 1.69 (m, 12 H); 2.38 (m, 2 H); 2.63 (m, 1 H); 2.79 (m, 1 H); from 2.95 to 3.19 (m, 4 H); 3.81 (m, 1H); 4.11 (m, 1 H); 4.64 (m, 1 H); 5.86 (m, 1 H); 6.95 (m, 2 H); 7.02 (d, J=7.5 Hz, 1 H); 7.07 (t, J=9.0 Hz, 1 H); 7.33 (t, J=7.5 Hz, 1 H); 7.67 (t, J=7.5 Hz, 1 H); 7.80 (d, J=7.5 Hz, 1 H); 7.90 (partially masked d, J=7.5 Hz, 1 H); 7.93 (d, J=7.5 Hz, 1 H); 8.02 (s, 1 H); 8.26 (d, J=9.0 Hz, 1 H); 9.39 (m, 1 H); 9.81 (m, 1 H).

MP: 172° C.

EXAMPLE 4

4.1: Base N-[(1S,2R)-1-benzyl-2-hydroxy-3-{[3-(trifluoromethyl)benzyl]amino}propyl]-1-oxo-2-(1-propylbutyl)-1,2,3,4-tetrahydroisoquinoline-5-carboxamide 43 mg of 1-oxo-2-(1-propylbutyl)-1,2,3,4-tetrahydroisoquinoline-5-carboxylic acid are dissolved in 2.5 cm³ of dichloromethane under an inert atmosphere at a temperature close to 20° C. 62 mg of (2R,3S)-3-amino-4-phenyl-1-{[3-(trifluoromethyl)benzyl]amino}butan-2-ol hydrochloride (2:1), 3 mg of hydroxybenzotriazole and 34 mg of 1-(3-dimethylaminopropyl)-3-ethylcarbodiimide hydrochloride are added to the solution. 0.124 cm³ of N,N-diisopropylethylamine is poured into the reaction medium. This medium is kept stirring for 20 h at a temperature close to 20° C. 10 cm³ of dichloromethane are added to the reaction mixture, then 10 cm³ of water. After decantation, the organic phase is washed with 5 cm³ of a saturated aqueous solution of sodium chloride, dried over magnesium sulfate and concentrated using a rotary evaporator under reduced pressure (5 kPa). The 100 mg of colorless oil obtained are purified by flash chromatography over silica (column: 7 g; particle size: 20-40 μm spherical; flow rate: 20 cm³/min; eluent: 100% ethyl acetate). After concentrating the fractions under reduced pressure, 40 mg of N-[(1S,2R)-1-benzyl-2-hydroxy-3-{[3-(trifluoromethyl)benzyl]amino}propyl]-1-oxo-2-(1-propylbutyl)-1,2,3,4-tetrahydroisoquinoline-5-carboxamide are obtained in the form of a colorless oil.

NMR: 0.88 (t, J=7.5 Hz, 3 H); 0.90 (t, J=7.5 Hz, 3 H); from 1.17 to 1.29 (m, 4 H); 1.37 to 1.56 (m, 4 H); from 2.46 to 2.60 (partially masked m, 2 H); from 2.62 to 2.78 (m, 3 H); from 2.97 to 3.18 (partially masked m, 3 H); 3.67 (m, 1 H); 3.87 (m, 2 H); 4.22 (m, 1 H); 4.62 (m, 1 H); 4.70 (m, 1 H); 7.17 (m, 2 H); from 7.22 to 7.30 (partially masked m, 5 H); 7.52 (t, J=7.5 Hz, 1 H); 7.56 (d, J=7.5 Hz, 1 H); 7.64 (d, J=7.5 Hz, 1 H); 7.69 (s, 1 H); 7.91 (m, 2 H)

4.2: Salt N-[(1S,2R)-1-benzyl-2-hydroxy-3-{[3-(trifluoromethyl)benzyl]amino}propyl]-1-oxo-2-(1-propylbutyl)-1,2,3,4-tetrahydroisoquinoline-5-carboxamide hydrochloride (1:1)

38 mg of N-[(1S,2R)-1-benzyl-2-hydroxy-3-{[3-(trifluoromethyl)benzyl]amino}propyl]-1-oxo-2-(1-propylbutyl)-1,2,3,4-tetrahydroisoquinoline-5-carboxamide are dissolved in 8 cm³ of ethyl ether at a temperature close to 20° C. 0.2 cm³ of a 4M hydrochloric acid solution in dioxane is added while stirring under argon. The reaction mixture precipitates. The stirring is stopped in order to remove the supernatant, then 5 cm³ of ethyl ether are again added. This operation is carried out 3 times. The last suspension is then concentrated under reduced pressure (5 kPa). 26 mg of N-[(1S,2R)-1-benzyl-2-hydroxy-3-{[3-(trifluoromethyl)benzyl]amino}propyl]-1-oxo-2-(1-propylbutyl)-1,2,3,4-tetrahydroisoquinoline-5-carboxamide hydrochloride (1:1) are obtained in the form of a white solid.

NMR: 0.85 (t, J=7.5 Hz, 3 H); 0.89 (t, J=7.5 Hz, 3 H); from 1.10 to 1.27 (m, 4 H); from 1.32 to 1.57 (m, 4 H); 2.33 (m, 2 H); 2.62 (m, 1 H); 2.91 (m, 1 H); 3.03 (m, 2 H); 3.13 (m, 1 H); 3.21 (m, 1 H); 3.85 (m, 1 H); 4.17 (m, 1 H); 4.34 (broad s, 2 H); 4.63 (m, 1 H); 5.93 (broad d, J=6.0 Hz, 1 H); from 7.15 to 7.36 (m, 7 H); 7.69 (t, J=7.5 Hz, 1 H); 7.80 (d, J=7.5 Hz, 1 H); 7.87 (d, J=7.5 Hz, 1 H); 7.91 (d, J=7.5 Hz, 1 H); 8.00 (s, 1 H); 8.27 (d, J=9.0 Hz, 1 H); 9.04 (broad unresolved m, 1 H); 9.30 (broad unresolved m, 1 H)

LC-MS-DAD-ELSD: $608^{(-)}$=$(M-H)^{(-)}$; $654^{(-)}$=(M+formic acid-H)$^{(-)}$; $610^{(+)}$=$(M+H)^{(+)}$

EXAMPLE 5

5.1: Base 2-benzyl-N-[(1S,2R)-1-(3,5-difluorobenzyl)-2-hydroxy-3-({1-[3-(trifluoromethyl)phenyl]cyclopropyl}amino)propyl]-1-oxo-1,2,3,4-tetrahydroisoquinoline-5-carboxamide

5.1.1: 2-(2-Bromophenyl)ethyl methanesulfonate 9.8 g of 2-(2-bromophenyl)ethanol and 4.7 cm³ of pyridine are dissolved under an inert atmosphere in 200 cm³ of dichloromethane at a temperature close to 20° C. The reaction mixture is cooled to a temperature close to 0° C. and 4.55 cm³ of methanesulfonyl chloride are introduced dropwise. The stirring is continued for 72 h, during which time the medium is allowed to gradually climb back up to a temperature close to 20° C. 100 cm³ of a saturated aqueous solution of sodium hydrogen carbonate are added to the reaction mixture. Stirring is continued for 10 min. The aqueous phase is extracted with dichloromethane. The organic phases are combined, washed with a saturated aqueous solution of sodium chloride, dried over magnesium sulfate, filtered then concentrated using a rotary evaporator under reduced pressure (5 kPa). The 18 g of brown oil obtained are purified by flash chromatography over silica (column: 200 g; particle size: 15-40 μm; eluent: 100% dichloromethane to 90% dichloromethane/10% ethyl acetate gradient). After concentrating the fractions under reduced pressure, 12.9 g of 2-(2-bromophenyl)ethyl methanesulfonate are obtained in the form of a colorless oil.

EI: m/z=278$^+$ $^{79}$Br=M$^+$; m/z=183 (M-OSO$_2$CH$_3$)$^+$; m/z=169 (m/z=183-CH$_2$)$^+$; m/z=90 (m/z=169-Br)$^+$.

5.1.2: N-Benzyl-2-(2-bromophenyl)ethanamine 3.18 g of 2-(2-bromophenyl)ethyl methanesulfonate, 6.2 g of 1-phenylmethanamine, 7.87 g of potassium carbonate and 65 cm³ of tetrahydrofuran are stirred under an inert atmosphere for 16 h under the reflux of the solvent. The reaction mixture is cooled to a temperature close to 20° C., then in ice. 100 cm³ of ethyl acetate and 200 cm³ of water are then added thereto. Stirring is continued for 5 min. The aqueous phase is extracted using ethyl acetate. The organic phases are combined, washed with a saturated aqueous solution of sodium chloride, dried over magnesium sulfate and concentrated using a rotary evaporator under reduced pressure (5 kPa). The 7.8 g of brown oil obtained are purified by flash chromatography over silica (column: 400 g; particle size: 15-40 μm; eluent: 100% dichloromethane to 90% dichloromethane/10% methanol gradient). After concentrating the fractions under reduced pressure, 2.49 g of N-benzyl-2-(2-bromophenyl) ethanamine are obtained.

NMR: 2.21 (broad unresolved m, 1 H) 2.72 (t, J=7.6 Hz, 2 H) 2.86 (t, J=7.6 Hz, 2 H) 3.73 (s, 2 H) 7.09-7.38 (m, 8 H) 7.55 (broad d, J=8.1 Hz, 1 H)

LC-MS-DAD-ELSD: m/z=290 $^{79}$Br=MH$^+$; m/z=198 (M-CH$_2$Ph)$^+$; m/z=91=(CH$_2$Ph)$^+$

5.1.3: Methyl benzyl[2-(2-bromophenyl)ethyl]carbamate 2.48 g of N-benzyl-2-(2-bromophenyl)ethanamine in solution in 50 cm$^3$ of anhydrous tetrahydrofuran are stirred under an inert atmosphere at 0° C. 1.2 cm$^3$ of triethylamine are added to the reaction mixture, then 0.67 cm$^3$ of methyl chloroformate is introduced using a syringe. The reaction mixture is kept stirring for 1 h at 0° C., then 5 h at a temperature close to 20° C. The reaction mixture is poured into a mixture containing ice, ethyl acetate and water. Stirring is continued for 10 min. The aqueous phase is extracted with ethyl acetate. The organic phases are combined, washed with a saturated aqueous solution of sodium chloride, dried over magnesium sulfate, then concentrated using a rotary evaporator under reduced pressure (5 kPa). The brown oil obtained is purified by flash chromatography over silica (column: 200 g; particle size: 15-40 μm; eluent: 70% cyclohexane/30% ethyl acetate). After concentrating the fractions under reduced pressure, 2.51 g of methyl benzyl[2-(2-bromophenyl)ethyl]carbamate are obtained in the form of an oil.

NMR: 2.89 (t, J=7.6 Hz, 2 H) 3.37 (t, J=7.6 Hz, 2 H) 3.50-3.67 (broad unresolved m, 3 H) 4.39 (s, 2 H) 7.11-7.39 (m, 8 H) 7.57 (broad d, J=8.1 Hz, 1 H)

LC-MS-DAD-ELSD: m/z=348 $^{79}$Br=MH$^+$; m/z=270=(M-Ph)$^+$; m/z=91=(CH$_2$Ph)$^+$

EI: m/z=347 $^{79}$Br=M$^+$; m/z=268=(M-Br)$^+$; m/z=178=(m/z=268-(CH$_2$Ph)$^+$; m/z=91=(CH$_2$)Ph)$^+$

5.1.4: 2-Benzyl-5-bromo-3,4-dihydroisoquinolin-1(2H)-one 0.5 g of methyl benzyl[2-(2-bromophenyl)ethyl]carbamate is dissolved under an inert atmosphere in 20 cm$^3$ of dichloromethane at a temperature close to 20° C. 0.526 g of N,N-dimethylpyridin-4-amine is added, then the reaction mixture is cooled to a temperature close to 0° C. 1.2 cm$^3$ of trifluoromethanesulfonic anhydride is introduced dropwise. The suspension obtained is stirred for 15 min at a temperature close to 0° C., then for 4 h 30 min while allowing it to gradually climb back up to a temperature close to 20° C. Dichloromethane is added to the reaction mixture and also a saturated aqueous solution of ammonium chloride. The aqueous phase is extracted with dichloromethane. The organic phases are combined, dried over magnesium sulfate then concentrated using a rotary evaporator under reduced pressure (5 kPa). The crude product obtained (1 g) is purified by flash chromatography over silica (column: 90 g; particle size: 15-40 μm; eluent: 100% dichloromethane to 95% dichloromethane/5% ethyl acetate gradient). After concentrating the fractions under reduced pressure, 0.22 g of 2-benzyl-5-bromo-3,4-dihydroisoquinolin-1(2 H)-one is obtained.

NMR: 3.01 (t, J=6.7 Hz, 2 H) 3.52 (t, J=6.7 Hz, 2 H) 4.71 (s, 2 H) 7.22-7.40 (m, 6 H) 7.79 (dd, J=7.8, 1.4 Hz, 1 H) 7.98 (dd, J=7.8, 1.4 Hz, 1 H)

ES: m/z=316 $^{79}$Br=MH$^+$; m/z=238=(M+H-Ph)$^+$

5.1.5: 2-Benzyl-1-oxo-1,2,3,4-tetrahydroisoquinoline-5-carboxylic acid

Introduced successively, at a temperature close to 20° C., into a three-necked flask that is stirred and purged using carbon monoxide are 0.46 g of 2-benzyl-5-bromo-3,4-dihydroisoquinolin-1(2H)-one, 18 cm$^3$ of dimethylformamide, 1.8 cm$^3$ of water, 0.543 g of potassium acetate, 48 mg of potassium iodide, 131 mg of palladium acetate and 305 mg of triphenyl phosphine. The reaction mixture is subjected to a carbon monoxide bubbling, then is heated at 100° C. for 6 h. The reaction mixture is kept at 100° C. under an overpressure of carbon monoxide for 20 h, then is cooled to 25° C. in order to be filtered through a 45 μm Millipore membrane. The residue is washed with ethyl acetate. The filtrate is concentrated using a rotary evaporator under reduced pressure (5 kPa). The oily residue obtained is taken up in a mixture of ice and ethyl acetate. The pH is alkanized with 5M sodium hydroxide (pH>10). After decanting the filtrate, the aqueous phase is washed with 2 lots of ethyl acetate. It is then acidified, with stirring, with a 5M hydrochloric acid solution (pH=1), then extracted with ethyl acetate. The organic phases are combined, washed with a saturated aqueous solution of sodium chloride, dried over magnesium sulfate and concentrated using a rotary evaporator under reduced pressure (5 kPa). The 440 mg of crude product obtained are purified by flash chromatography over silica (particle size: 15-40 μm; eluent: 95% dichloromethane/5% methanol). After concentrating the fractions under reduced pressure, 315 mg of 2-benzyl-1-oxo-1,2,3,4-tetrahydroisoquinoline-5-carboxylic acid are obtained in the form of yellow crystals.

NMR: 3.30 (t, J=6.5 Hz, 2 H) 3.47 (t, J=6.5 Hz, 2 H) 4.73 (s, 2 H) 7.25-7.39 (m, 5 H) 7.47 (t, J=7.8 Hz, 1 H) 8.00 (dd, J=7.8, 1.5 Hz, 1 H) 8.15 (dd, J=7.8, 1.5 Hz, 1 H)

ES: m/z=282=MH$^+$

5.1.6: 2-Benzyl-N-[(1S,2R)-1-(3,5-difluorobenzyl)-2-hydroxy-3-({1-[3-(trifluoromethyl)phenyl]cyclopropyl}amino)propyl]-1-oxo-1,2,3,4-tetrahydroisoquinoline-5-carboxamide A solution of 100 mg of 2-benzyl-1-oxo-1,2,3,4-tetrahydroisoquinoline-5-carboxylic acid, 168 mg of (2R,3S)-3-amino-4-(3,5-difluorophenyl)-1-({1-[3-(trifluoromethyl)phenyl]cyclopropyl}amino)butan-2-ol hydrochloride (2:1), 7.2 mg of hydroxybenzotriazole, 85 mg of 1-(3-dimethylaminopropyl)-3-ethylcarbodiimide hydrochloride and 0.243 cm$^3$ of N,N-diisopropylethylamine in 10 cm$^3$ of dichloromethane is stirred at a temperature close to 20° C. for 20 h. Dichloromethane is added to the reaction medium. The organic phase is washed with water then with a saturated aqueous solution of sodium chloride, dried over sodium sulfate and concentrated using a rotary evaporator under reduced pressure (5 kPa). The 400 mg of product obtained are purified by flash chromatography over silica (column: 50 g; particle size: 15-40 μm; eluent: 100% ethyl acetate). After concentrating the fractions under reduced pressure, 103 mg of 2-benzyl-N-[(1S,2R)-1-(3,5-difluorobenzyl)-2-hydroxy-3-({1-[3-(trifluoromethyl)phenyl]cyclopropyl}amino)propyl]-1-oxo-1,2,3,4-tetrahydroisoquinoline-5-carboxamide are obtained.

NMR: 0.95 (m, 2 H) 1.02 (m, 2 H) 2.38-2.55 (partially masked m, 5 H) 3.11 (dd, J=13.7, 3.1 Hz, 1 H) 3.28 (partially masked m, 2 H) 3.50 (m, 1 H) 4.11 (m, 1 H) 4.69 (m, 2 H) 4.89 (d, J=5.9 Hz, 1 H) 6.91 (m, 2 H) 6.97 (tt, J=9.2, 2.2 Hz, 1 H) 7.11 (dd, J=7.7, 1.2 Hz, 1 H) 7.26-7.39 (m, 6 H) 7.46 (m, 2 H) 7.55 (m, 1 H) 7.67 (broad s, 1 H) 7.97 (dd, J=7.7, 1.2 Hz, 1 H) 8.15 (d, J=9.3 Hz, 1 H)

ES: m/z=664=MH$^+$ 5.2: Salt 2-benzyl-N-[(1S,2R)-1-(3,5-difluorobenzyl)-2-hydroxy-3-({1-[3-(trifluoromethyl)phenyl]cyclopropyl}amino)propyl]-1-oxo-1,2,3,4-tetrahydroisoquinoline-5-carboxamide hydrochloride (1:1)

At a temperature close to 20° C., 100 mg of 2-benzyl-N-[(1S,2R)-1-(3,5-difluorobenzyl)-2-hydroxy-3-({1-[3-(trifluoromethyl)phenyl]cyclopropyl}amino)propyl]-1-oxo-1,2,3,4-tetrahydroisoquinoline-5-carboxamide are dissolved in 2 cm$^3$ of ethyl ether. Since the product crystallizes, the ethyl ether is removed under reduced pressure (5 kPa). The residue is dissolved at high temperature in ethyl acetate then the solution obtained is cooled to a temperature close to 0° C. and 0.7 cm$^3$ of a 2M solution of hydrochloric acid in ethyl ether is added. Stirring is continued for 15 min. The solution is then concentrated under reduced pressure (5 kPa). 3 cm$^3$ of ethyl ether are added. The reaction mixture precipitates. The stirring is stopped in order to remove the supernatant, then ethyl ether is again added. This operation is carried out twice. The last suspension is then concentrated under reduced pressure (5 kPa). 94 mg of 2-benzyl-N-[(1S,2R)-1-(3,5-difluorobenzyl)-2-hydroxy-3-({1-[3-(trifluoromethyl)phenyl]cyclopropyl}amino)propyl]-1-oxo-1,2,3,4-tetrahydroisoquinoline-5-carboxamide hydrochloride (1:1) are obtained in the form of a pale yellow solid.

NMR: from 1.11 to 1.65 (m, 4 H); from 2.30 to 3.40 (partially masked m, 8 H); 3.78 (m, 1 H); 4.10 (m, 1 H); 4.65 (d, J=15.0 Hz, 1 H); 4.72 (d, J=15.0 Hz, 1 H); 5.81 (broad unresolved m, 1 H); 6.81 (m, 2 H); 7.00 (tt, J=2.5 and 9.5 Hz, 1 H); 7.05 (dd, J=1.5 and 7.5 Hz, 1 H); 7.29 (m, 3 H); 7.38 (m, 3 H); 7.61 (t, J=7.5 Hz, 1 H); 7.72 (broad d, J=7.5 Hz, 1 H); 7.85 (broad d, J=7.5 Hz, 1 H); 7.98 (masked m, 1 H); 7.99 (dd, J=1.5 and 7.5 Hz, 1 H); 8.28 (d, J=9.0 Hz, 1 H); from 9.20 to 9.80 (broad unresolved m, 2 H)

ES: m/z=663=MH$^+$

MP: 178° C.

EXAMPLE 6

6.1: Base N-[(1S,2R)-1-(3,5-difluorobenzyl)-2-hydroxy-3-({1-[3-(trifluoromethyl)phenyl]cyclopropyl}amino)propyl]-1-oxo-2-pentyl-1,2,3,4-tetrahydroisoquinoline-5-carboxamide 6.1.1: N-[2-(2-bromophenyl)ethyl]pentan-1-amine 7 g of 2-(2-bromophenyl)ethyl methanesulfonate, 14.5 cm$^3$ of 1-pentanamine, 17.33 g of potassium carbonate and 200 cm$^3$ of tetrahydrofuran are stirred at a temperature between 65° C. and 70° C. under an inert atmosphere for 72 h. The reaction mixture is brought to 30° C. in order to be poured over a mixture of water, ice and ethyl acetate. The phases are stirred for 5 min, then are separated. The aqueous phase is extracted 3 times with ethyl acetate. The organic phases are combined, washed with a saturated aqueous solution of sodium chloride, dried over magnesium sulfate and concentrated using a rotary evaporator under reduced pressure (5 kPa). The 6.6 g of oil obtained are purified by flash chromatography over silica (column: 200 g; particle size: 15-40 µm; eluent: 95% dichloromethane/5% methanol to 90% dichloromethane/10% methanol gradient). After concentrating the fractions under reduced pressure, 4.56 g of N-[2-(2-bromophenyl)ethyl]pentan-1-amine are obtained in the form of a white oil.

NMR: 0.86 (t, J=7.0 Hz, 3 H) 1.21-1.32 (m, 4 H) 1.41 (m, 2 H) 2.55 (t, J=7.3 Hz, 2 H) 2.74 (m, 2 H) 2.84 (m, 2 H) 3.14 (broad unresolved m, 1 H) 7.14 (td, J=7.7, 2.0 Hz, 1 H) 7.22-7.39 (m, 2 H) 7.56 (dd, J=7.7, 2.0 Hz, 1 H)

ES: m/z=270 ($^{79}$Br)=MH$^+$ 6.1.2: Methyl[2-(2-bromophenyl)ethyl]pentylcarbamate 4.51 g of N-[2-(2-bromophenyl)ethyl]pentan-1-amine in suspension in 120 cm$^3$ of anhydrous tetrahydrofuran are stirred under an inert atmosphere at 5° C. 2.33 cm$^3$ of triethylamine, then 1.3 cm$^3$ of methyl chloroformate are added to the reaction mixture. This mixture is then stirred for 20 h at a temperature close to 20° C. before being poured over a mixture of water and ice. The phases are stirred for 5 min, then separated. The aqueous phase is extracted 3 times with ethyl acetate. The organic phases are combined, washed with a saturated aqueous solution of sodium chloride, dried over magnesium sulfate and concentrated using a rotary evaporator under reduced pressure (5 kPa). The 6.33 g of oil obtained are purified by flash chromatography over silica (column: 200 g; particle size: 15-40 µm; eluent: 20% heptane/80% ethyl acetate). After concentrating the fractions under reduced pressure, 5.45 g of methyl[2-(2-bromophenyl)ethyl]pentylcarbamate are obtained in the form of a colorless oil NMR: 0.85 (t, J=7.3 Hz, 3 H) 1.18 (m, 2 H) 1.27 (m, 2 H) 1.43 (m, 2 H) 2.91 (m, 2 H) 3.11 (broad t, J=7.6 Hz, 2 H) 3.38 (m, 2 H) 3.45-3.70 (broad unresolved m, 3 H) 7.17 (m, 1 H) 7.32 (m, 2 H) 7.59 (d, J=7.8 Hz, 1 H)

ES: m/z=328 ($^{79}$Br)=MH$^+$; m/z=258=(M-C$_5$H$_{10}$)$^+$; m/z=226=(m/z=258-OCH$_4$)$^+$; m/z=183=(m/z=226-NHCO)$^+$ 6.1.3: 5-Bromo-2-pentyl-3,4-dihydroisoquinolin-1(2H)-one 5.44 g of methyl[2-(2-bromophenyl)ethyl]pentylcarbamate are dissolved, under an inert atmosphere, in 200 cm$^3$ of dichloromethane at a temperature close to 20° C. 6.07 g of 4-dimethylaminopyridine are added to the reaction mixture. It is cooled to a temperature in the vicinity of 0° C. 13.94 cm$^3$ of trifluoromethanesulfonic anhydride are poured into the reaction mixture over 15 min. The suspension is kept stirring for 4 h at a temperature close to 20° C. Dichloromethane and also 50 cm$^3$ of a water/ice mixture are added to the reaction medium. The 4-dimethylaminopyridine is filtered. The filtrate is decanted, the aqueous phase is extracted with dichloromethane. The organic phases are combined, washed with a saturated aqueous solution of sodium chloride, dried over magnesium sulfate and concentrated using a rotary evaporator under reduced pressure (5 kPa). The crude product obtained is purified by flash chromatography over silica (column: 200 g; particle size: 15-40 µm; eluent: 90% dichloromethane/10% ethyl acetate). After concentrating the fractions under reduced pressure, 4.14 g of 5-bromo-2-pentyl-3,4-dihydroisoquinolin-1(2H)-one are obtained in the form of a colorless oil.

NMR: 0.87 (t, J=7.1 Hz, 3 H) 1.20-1.38 (m, 4 H) 1.55 (m, 2 H) 3.00 (t, J=6.7 Hz, 2 H) 3.45 (t, J=7.3 Hz, 2 H) 3.56 (t, J=6.7 Hz, 2 H) 7.30 (t, J=7.8 Hz, 1 H) 7.76 (dd, J=7.8, 1.2 Hz, 1 H) 7.90 (dd, J=7.8, 1.2 Hz, 1 H)

ES: m/z=296($^{79}$Br)=MH$^+$; m/z=318=MNaH$^+$; m/z=359=MNaACNH$^+$; m/z=613=(2MNaH$^+$)

6.1.4: 1-Oxo-2-pentyl-1,2,3,4-tetrahydroisoquinoline-5-carboxylic acid

Introduced successively at a temperature close to 20° C., into a three-necked flask that is stirred and purged using carbon monoxide are 500 mg of 5-bromo-2-pentyl-3,4-dihydroisoquinolin-1(2H)-one, 18 cm³ of dimethylformamide, 2 cm³ of water, 0.63 g of potassium acetate, 56 mg of potassium iodide, 152 mg of palladium acetate and 354 mg of triphenylphosphine. The reaction mixture is subjected to a carbon monoxide bubbling, then is heated at 100° C. for 6 h 30 min. The reaction mixture is kept at 100° C. for 20 h, then cooled to 25° C. in order to be filtered over a 45 µm Millipore membrane. The filtrate is concentrated using a rotary evaporator under reduced pressure (5 kPa). The residue obtained is taken up in a water/ice mixture and ethyl acetate. The pH is alkanized with 5M sodium hydroxide (pH>10). After decanting, the aqueous phase is washed 3 times with ethyl acetate. It is then acidified, while stirring, with a 5M hydrochloric acid solution (pH=1) then extracted 3 times with ethyl acetate. The organic phases are combined, washed with a saturated aqueous solution of sodium chloride, dried over magnesium sulfate, filtered and concentrated using a rotary evaporator under reduced pressure (5 kPa). 430 mg of 1-oxo-2-pentyl-1,2,3,4-tetrahydroisoquinoline-5-carboxylic acid are obtained in the form of a beige solid.

NMR: 0.87 (t, J=7.1 Hz, 3 H) 1.19-1.39 (m, 4 H) 1.56 (m, 2 H) 3.30 (partially masked m, 2 H) 3.44-3.53 (m, 4 H) 7.44 (t, J=7.8 Hz, 1 H) 7.97 (dd, J=7.8, 1.5 Hz, 1 H) 8.08 (dd, J=7.8, 1.5 Hz, 1 H) 13.15 (broad unresolved m, 1 H)

ES: m/z=262=MH⁺; m/z=523 (2 MH⁺)

6.1.5: N-[(1S,2R)-1-(3,5-Difluorobenzyl)-2-hydroxy-3-({1-[3-(trifluoromethyl)phenyl]cyclopropyl}amino)propyl]-1-oxo-2-pentyl-1,2,3,4-tetrahydroisoquinoline-5-carboxamide 326 mg of (2R,3S)-3-amino-4-(3,5-difluorophenyl)-1-({1-[3-(trifluoromethyl)phenyl]cyclopropyl}amino)butan-2-ol hydrochloride (2:1), 180 mg of 1-oxo-2-pentyl-1,2,3,4-tetrahydroisoquinoline-5-carboxylic acid, 14 mg of hydroxybenzotriazole, 165 mg of 1-(3-dimethylaminopropyl)-3-ethylcarbodiimide hydrochloride and 0.47 cm³ of N,N-diisopropylethylamine in 18 cm³ of dichloromethane are stirred for 20 h at a temperature close to 20° C. 10 cm³ of water and dichloromethane are added to the reaction medium. The suspension is filtered, washed successively with water and dichloromethane. The solid obtained is taken up in ethyl ether, filtered, washed with ethyl ether and dried under vacuum at 20° C. 360 mg of N-[(1S,2R)-1-(3,5-difluorobenzyl)-2-hydroxy-3-({1-[3-(trifluoromethyl)phenyl]cyclopropyl}amino)propyl]-1-oxo-2-pentyl-1,2,3,4-tetrahydroisoquinoline-5-carboxamide are obtained in the form of a white solid.

NMR: 0.87 (t, J=7.1 Hz, 3 H) 0.98 (m, 2 H) 1.04 (m, 2 H) 1.18-1.38 (m, 4 H) 1.53 (m, 2 H) 2.36-2.69 (partially masked m, 3 H) 3.13 (dd, J=14.2, 3.4 Hz, 1 H) 3.31 (partially masked m, 6 H) 4.12 (m, 1 H) 4.93 (d, J=5.9 Hz, 1 H) 6.93 (m, 2 H) 7.03 (tt, J=9.2, 2.0 Hz, 1 H) 7.08 (broad d, J=7.8 Hz, 1 H) 7.31 (t, J=7.8 Hz, 1 H) 7.46-7.65 (m, 4 H) 7.69 (broad s, 1 H) 7.89 (broad d, J=7.8 Hz, 1 H) 8.16 (d, J=9.3 Hz, 1 H)

ES: m/z=644=MH⁺; m/z=642=MH⁻; m/z=688=MHCOO⁻

6.2: Salt N-[(1S,2R)-1-(3,5-difluorobenzyl)-2-hydroxy-3-({1-[3-(trifluoromethyl)phenyl]cyclopropyl}amino)propyl]-1-oxo-2-pentyl-1,2,3,4-tetrahydroisoquinoline-5-carboxamide hydrochloride (1:1)

360 mg of N-[(1S,2R)-1-(3,5-difluorobenzyl)-2-hydroxy-3-({1-[3-(trifluoromethyl)phenyl]cyclopropyl}amino)propyl]-1-oxo-2-pentyl-1,2,3,4-tetrahydroisoquinoline-5-carboxamide are stirred under an inert atmosphere in 6 cm³ of ethyl ether at a temperature close to 5° C. 1.9 cm³ of a 2M solution of hydrochloric acid in ether are added. The solution is concentrated under reduced pressure (5 kPa). Ethyl ether is added. The suspension is stirred then, after stopping the stirring, the supernatant is removed. Ethyl ether is again added. This operation is carried out several times. The last suspension is then concentrated under reduced pressure (5 kPa). 363 mg of N-[(1S,2R)-1-(3,5-difluorobenzyl)-2-hydroxy-3-({1-[3-(trifluoromethyl)phenyl]cyclopropyl}amino)propyl]-1-oxo-2-pentyl-1,2,3,4-tetrahydroisoquinoline-5-carboxamide hydrochloride (1:1) are obtained in the form of a white solid.

NMR: 0.88 (t, J=7.0 Hz, 3 H); from 1.18 to 1.40 (m, 6 H); from 1.47 to 1.70 (m, 4 H); from 2.30 to 2.82 (partially masked m, 4 H); 3.02 (m, 1 H); 3.12 (m, 1 H); from 3.20 to 3.60 (partially masked m, 4 H); 3.83 (m, 1 H); 4.10 (m, 1 H); 5.87 (broad unresolved m, 1 H); 6.95 (m, 2 H); 7.05 (m, 2 H); 7.32 (t, J=7.5 Hz, 1 H); 7.68 (t, J=7.5 Hz, 1 H); 7.81 (broad d, J=7.5 Hz, 1 H); 7.91 (broad d, J=7.5 Hz, 2 H); 8.03 (broad s, 1 H); 8.31 (d, J=8.5 Hz, 1 H); 9.44 (broad m, 1 H); 9.96 (broad m, 1 H)

ES: m/z=644=MH⁺; m/z=1287=(2 MH⁺)

MP: 165° C.

EXAMPLE 7

7.1: Base N-[(1S,2R)-1-(3,5-difluorobenzyl)-2-hydroxy-3-({1-[3-(trifluoromethyl)phenyl]cyclopropyl}amino)propyl]-2-(2-methoxyethyl)-1-oxo-1,2,3,4-tetrahydroisoquinoline-5-carboxamide

7.1.1: 2-(2-Bromophenyl)-N-(2-ethoxyethyl)ethanamine 3.5 g of 2-(2-bromophenyl)ethyl methanesulfonate, 5.59 g of 2-ethoxyethanamine, 8.67 g of potassium carbonate and 70 cm³ of tetrahydrofuran are stirred under the reflux of the solvent under an inert atmosphere for 48 h. The heating is stopped, then the reaction mixture is filtered. The insoluble material is washed twice with ethyl acetate. The filtrate is concentrated using a rotary evaporator under reduced pressure (5 kPa). The product obtained is purified by flash chromatography over silica (column: 330 g; particle size: 20-40 µm, spherical; eluent: 100% ethyl acetate to 90% ethyl acetate/10% methanol gradient). After concentrating the fractions under reduced pressure, 2.45 g of 2-(2-bromophenyl)-N-(2-ethoxyethyl)ethanamine are obtained in the form of a yellow oil.

NMR: 1.09 (t, J=7.1 Hz, 3 H) 1.78 (broad unresolved m, 1 H) 2.68 (t, J=5.9 Hz, 2 H) 2.74 (m, 2 H) 2.82 (m, 2 H) 3.37-3.44 (m, 4 H) 7.14 (td, J=7.7, 2.0 Hz, 1 H) 7.28-7.37 (m, 2 H) 7.56 (dd, J=7.7, 2.0 Hz, 1 H)

EI-MS: 283 m/z=212=(M-CH₂OC₂H₅)⁺; m/z=183=(m/z=212-NHCH₂)⁺

ES-MS: m/z=272 (⁷⁹Br)=MH⁺; m/z=226=(M-OC₂H₅)⁺; m/z=183=(m/z=226-NHC₂H₄)⁺

7.1.2: Methyl[2-(2-bromophenyl)ethyl](2-ethoxyethyl)carbamate 2.45 g of 2-(2-bromophenyl)-N-(2-ethoxyethyl)ethanamine and 1.4 cm³ of triethylamine in solution in 22 cm³ of anhydrous tetrahydrofuran are stirred under an inert atmosphere at 0° C. 1.3 cm³ of methyl chloroformate in solution in 4 cm³ of tetrahydrofuran are poured into the reaction mixture. This mixture is then stirred for 20 h at a temperature close to 20° C. 50 cm³ of a saturated aqueous solution of ammonium chloride and 50 cm³ of ethyl acetate are added. After decanting, the organic phase is washed twice with 20 cm³ of water then 20 cm³ of a saturated aqueous solution of sodium chloride, it is dried over magnesium sulfate and filtered through a bed of silica of 30 g. The latter is washed twice with 75 cm³ of ethyl acetate. The filtrate is concentrated using a rotary evaporator under reduced pressure (5 kPa). 2.97 g of methyl [2-(2-bromophenyl)ethyl](2-ethoxyethyl)carbamate are obtained in the form of a yellow oil.

NMR: 1.08 (t, J=7.1 Hz, 3 H) 2.92 (m, 2 H) 3.28 (partially masked m, 2 H) 3.34-3.63 (m, 9 H) 7.17 (m, 1 H) 7.26-7.39 (m, 2 H) 7.59 (broad d, J=7.8 Hz, 1 H)

ES-MS: m/z: 330 ($^{79}$Br)=MH⁺; m/z: 298=(M-OCH$_3$)⁺; m/z: 284=(M-OC$_2$H$_5$)⁺

7.1.3: 5-Bromo-2-(2-hydroxyethyl)-3,4-dihydroisoquinolin-1(2H)-one 1.5 g of methyl[2-(2-bromophenyl)ethyl](2-ethoxyethyl) carbamate are dissolved under an inert atmosphere in 140 cm³ of dichloromethane at a temperature close to 20° C. 1.6 g of 4-dimethylaminopyridine are added to the reaction mixture, which is cooled to a temperature in the vicinity of 0° C. 3.7 cm³ of trifluoromethanesulfonic anhydride in solution in 15 cm³ of dichloromethane are poured in to the reaction mixture over 30 min. The suspension is kept stirring for 1 h at 0° C., then for 48 h at a temperature close to 20° C. 100 cm³ of a saturated aqueous solution of sodium hydrogen carbonate are added to the reaction medium. Stirring is continued for 1 h at a temperature close to 20° C. After decanting, the organic phase is washed with 100 cm³ of a 20% aqueous solution of acetic acid then with 150 cm³ of a saturated aqueous solution of sodium hydrogen carbonate, dried over magnesium sulfate, filtered and concentrated using a rotary evaporator under reduced pressure (5 kPa). The crude product obtained is purified by filtration through a bed of silica of 20 g. The latter is washed with 100 cm³ of ethyl acetate. The filtrate is concentrated using a rotary evaporator under reduced pressure (5 kPa). 0.8 g of 5-bromo-2-(2-hydroxyethyl)-3,4-dihydroisoquinolin-1(2H)-one is obtained in the form of a beige oil.

NMR: 3.01 (t, J=6.6 Hz, 2 H) 3.47-3.67 (m, 6 H) 4.74 (t, J=5.4 Hz, 1 H) 7.31 (t, J=7.8 Hz, 1 H) 7.76 (dd, J=7.8, 1.1 Hz, 1 H) 7.90 (dd, J=7.8, 1.1 Hz, 1 H)

ES-MS: m/z: 270 ($^{79}$Br)=MH⁺; m/z: 252=(M−H$_2$O)⁺; m/z: 292=MNaH⁺

7.1.4: 5-Bromo-2-(2-methoxyethyl)-3,4-dihydroisoquinolin-1(2H)-one 0.39 g of 5-bromo-2-(2-hydroxyethyl)-3,4-dihydroisoquinolin-1(2H)-one is dissolved under an inert atmosphere in 3 cm³ of dimethylsulfoxide at a temperature close to 20° C. 105 mg of finely ground potassium hydroxide are added. The reaction mixture is stirred for 30 min at a temperature close to 20° C., then 0.108 cm³ of iodomethane is introduced. The stirring is continued for 20 h at a temperature close to 20° C. 30 cm³ of water and 30 cm³ of ethyl ether are added. After decanting, the organic phase is washed with 30 cm³ of a saturated aqueous solution of sodium chloride, dried over magnesium sulfate, filtered and concentrated using a rotary evaporator under reduced pressure (5 kPa). 170 mg of 5-bromo-2-(2-methoxyethyl)-3,4-dihydroisoquinolin-1 (2H)-one are obtained in the form of a yellow oil.

NMR: 2.99 (t, J=6.8 Hz, 2 H) 3.26 (s, 3 H) 3.52 (m, 2 H) 3.59-3.66 (m, 4 H) 7.31 (t, J=7.8 Hz, 1 H) 7.77 (dd, J=7.9, 1.2 Hz, 1 H) 7.90 (dd, J=7.9, 1.2 Hz, 1 H)

ES-MS: m/z=284 ($^{79}$Br)=MH⁺; m/z=252 ($^{79}$Br)=(m/z=284-CH$_3$OH)⁺; m/z=306 ($^{79}$Br)=MNaH⁺

7.1.5: 2-(2-Methoxyethyl)-1-oxo-1,2,3,4-tetrahydroisoquinoline-5-carboxylic acid Introduced successively, at a temperature close to 20° C., into a three-necked flask that is stirred and purged using carbon monoxide are 165 mg of 5-bromo-2-(2-methoxyethyl)-3,4-dihydroisoquinolin-1(2H)-one, 4 cm³ of dimethylformamide, 0.27 cm³ of water, 0.217 g of potassium acetate, 96 mg of potassium iodide, 26 mg of palladium acetate and 61 mg of triphenylphosphine. The reaction mixture is subjected to a carbon monoxide bubbling, then is heated at 100° C. for 4 h, then at a temperature close to 20° C. for 20 h. The reaction mixture is filtered through a Celite 545 pellet, which is washed twice with 10 cm³ of dimethylformamide. The filtrate is concentrated using a rotary evaporator under reduced pressure (5 kPa). The residue obtained is taken up in 20 cm³ of water, 2 cm³ of 5M sodium hydroxide and 10 cm³ of ethyl acetate. After decanting, the aqueous phase is washed with 10 cm³ of ethyl ether. It is then acidified, while stirring, with a 5M hydrochloric acid solution (pH=3-4), then extracted with 15 cm³ of ethyl acetate and 10 cm³ of dichloromethane. The organic phases are combined, dried over magnesium sulfate, filtered and concentrated using a rotary evaporator under reduced pressure (5 kPa). 107 mg of 2-(2-methoxyethyl)-1-oxo-1,2,3,4-tetrahydroisoquinoline-5-carboxylic acid are obtained in the form of an orange powder.

NMR: 3.27 (s, 3 H) 3.29 (t, J=6.6 Hz, 2 H) 3.50-3.58 (m, 4 H) 3.65 (t, J=5.7 Hz, 2 H) 7.44 (t, J=7.8 Hz, 1 H) 7.98 (dd, J=7.8, 1.5 Hz, 1 H) 8.09 (dd, J=8.1, 1.2 Hz, 1 H) 12.79 (broad unresolved m, 1 H)

ES-MS: m/z=250=MH⁺; m/z=272 MNaH⁺; m/z=521=(2MNaH⁺)

7.1.6: N-[(1S,2R)-1-(3,5-Difluorobenzyl)-2-hydroxy-3-({1-[3-(trifluoromethyl)phenyl] cyclopropyl}amino)propyl]-2-(2-methoxyethyl)-1-oxo-1,2,3,4-tetrahydroisoquinoline-5-carboxamide Poured into a suspension of 242 mg of (2R,3S)-3-amino-4-(3,5-difluorophenyl)-1-({1-[3-(trifluoromethyl)phenyl] cyclopropyl}amino)butan-2-ol hydrochloride (2:1), 104 mg of 2-(2-methoxyethyl)-1-oxo-1,2,3,4-tetrahydroisoquinoline-5-carboxylic acid, 8 mg of hydroxybenzotriazole, 99 mg of 1-(3-dimethylaminopropyl)-3-ethylcarbodiimide hydrochloride in 7 cm³ of dichloromethane is 0.28 cm³ of N,N-diisopropylethylamine at a temperature close to 20° C. The reaction mixture is kept stirring for 20 h at a temperature close to 20° C. The suspension obtained is filtered and the precipitate is washed 3 times with 5 cm³ of ethyl ether, then dried under vacuum. 79 mg of N-[(1S,2R)-1-(3,5-difluorobenzyl)-2-hydroxy-3-({1-[3-(trifluoromethyl)phenyl] cyclopropyl}amino)propyl]-2-(2-methoxyethyl)-1-oxo-1,2,3,4-tetrahydroisoquinoline-5-carboxamide are obtained in the form of a white powder.

NMR: 0.94-1.08 (m, 4 H) 1.25 (broad unresolved m, 1 H) 2.34-2.83 (partially masked m, 5 H) 3.12 (dd, J=13.9, 3.7 Hz, 1 H) 3.26 (s, 3 H) 3.36 (m, 2 H) 3.46-3.70 (m, 5 H) 4.13 (m, 1 H) 4.91 (d, J=6.4 Hz, 1 H) 6.93 (m, 2 H) 7.02 (tt, J=9.4, 2.2 Hz, 1 H) 7.09 (dd, J=7.8, 1.0 Hz, 1 H) 7.32 (t, J=7.8 Hz, 1 H) 7.46-7.60 (m, 3 H) 7.69 (s, 1 H) 7.90 (dd, J=7.8, 1.0 Hz, 1 H) 8.17 (d, J=9.3 Hz, 1 H)

7.2: Salt N-[(1S,2R)-1-(3,5-difluorobenzyl)-2-hydroxy-3-({1-[3-(trifluoromethyl)phenyl]cyclopropyl}amino)propyl]-2-(2-methoxyethyl)-1-oxo-1,2,3,4-tetrahydroisoquinoline-5-carboxamide hydrochloride (1:1)

79 mg of N-[(1S,2R)-1-(3,5-difluorobenzyl)-2-hydroxy-3-({1-[3-(trifluoromethyl)phenyl]cyclopropyl}amino)propyl]-2-(2-methoxyethyl)-1-oxo-1,2,3,4-tetrahydroisoquinoline-5-carboxamide are dissolved in 2 cm³ of dioxane at a temperature close to 20° C. 1 cm³ of a 4M solution of hydrochloric acid in ethyl ether is added while stirring under argon, at a temperature of 20° C. The reaction mixture is concentrated under vacuum at a temperature of 40° C. 83 mg of N-[(1S,2R)-1-(3,5-difluorobenzyl)-2-hydroxy-3-({1-[3-(trifluoromethyl)phenyl]cyclopropyl}amino)propyl]-2-(2-methoxyethyl)-1-oxo-1,2,3,4-tetrahydroisoquinoline-5-carboxamide hydrochloride (1:1) are obtained in the form of a white powder.

NMR: from 1.20 to 1.68 (m, 4 H); from 2.30 to 2.86 (partially masked m, 4 H); 3.00 (m, 1 H); 3.12 (m, 1 H); from 3.20 to 3.70 (partially masked m, 9 H); 3.79 (m, 1 H); 4.12 (m, 1 H); 5.83 (m, 1 H); 6.93 (m, 2 H); 7.04 (m, 2 H); 7.33 (t, J=7.5 Hz, 1 H); 7.69 (broad t, J=7.5 Hz, 1 H); 7.81 (broad d, J=7.5 Hz, 1 H); 7.89 (broad m, 1 H); 7.92 (d, J=7.5 Hz, 1 H); 8.01 (broad s, 1 H); 8.26 (broad d, J=8.5 Hz, 1 H); 9.32 (broad m, 1 H); 9.49 (broad m, 1 H)

ES-MS: m/z: 632=MH$^+$

EXAMPLE 8

8.1: Base N-[(1S,2R)-1-(3,5-difluorobenzyl)-2-hydroxy-3-({1-[3-(trifluoromethyl)phenyl]cyclopropyl}amino)propyl]-2-(2-ethoxyethyl)-1-oxo-1,2,3,4-tetrahydroisoquinoline-5-carboxamide 8.1.1: 5-Bromo-2-(2-ethoxyethyl)-3,4-dihydroisoquinolin-1(2H)-one 0.363 g of 5-bromo-2-(2-hydroxyethyl)-3,4-dihydroisoquinolin-1(2H)-one is dissolved under an inert atmosphere in 3 cm³ of dimethylsulfoxide at a temperature close to 20° C. 98 mg of finely ground potassium hydroxide are added. The reaction mixture is stirred for 30 min at a temperature close to 20° C., then 0.131 cm³ of iodoethane is introduced. The stirring is continued for 20 h at a temperature close to 20° C. 50 cm³ of a water/ice mixture and 80 cm³ of ethyl ether are added. After decanting, the organic phase is washed with 3 times with 10 cm³ of water, 30 cm³ of a saturated aqueous solution of sodium chloride, dried over magnesium sulfate, filtered and concentrated using a rotary evaporator under reduced pressure (5 kPa). 356 mg of 5-bromo-2-(2-ethoxyethyl)-3,4-dihydroisoquinolin-1(2H)-one are obtained in the form of a colorless oil.

NMR: 1.09 (t, J=7.1 Hz, 3 H) 3.00 (t, J=6.6 Hz, 2 H) 3.45 (q, J=7.1 Hz, 2 H) 3.55 (m, 2 H) 3.62 (m, 4 H) 7.31 (t, J=7.8 Hz, 1 H) 7.77 (dd, J=7.8, 1.2 Hz, 1 H) 7.90 (dd, J=7.8, 1.2 Hz, 1 H)

ES-MS: m/z: 298 ($^{79}$Br)=MH$^+$; m/z: 252 ($^{79}$Br)=(M-OC$_2$H$_6$)$^+$; m/z: 320 ($^{79}$Br)=MNaH$^+$

EI-MS: m/z: 297 ($^{79}$Br)=M$^+$; m/z: 268 ($^{79}$Br)=(M-C$_2$H$_5$)$^+$; m/z: 251 ($^{79}$Br)=(m/z=268-OH)$^+$; m/z: 238 ($^{79}$Br)=(m/z=251-CH)$^+$; m/z: 159=(m/z=238-Br)$^+$ 8.1.2: 2-(2-Ethoxyethyl)-1-oxo-1,2,3,4-tetrahydroisoquinoline-5-carboxylic acid Introduced successively, at a temperature close to 20° C., into a three-necked flask that is stirred and purged using carbon monoxide are 350 mg of 5-bromo-2-(2-ethoxyethyl)-3,4-dihydroisoquinolin-1(2H)-one, 9 cm³ of dimethylformamide, 0.5 cm³ of water, 0.438 g of potassium acetate, 195 mg of potassium iodide, 53 mg of palladium acetate and 123 mg of triphenylphosphine. The reaction mixture is subjected to a carbon monoxide bubbling, then is heated at 100° C. for 4 h, then at a temperature close to 20° C. for 20 h. The reaction mixture is filtered through a Celite 545 pellet, which is washed twice with 10 cm³ of dimethylformamide. The filtrate is concentrated using a rotary evaporator under reduced pressure (5 kPa). The residue obtained is taken up in 20 cm³ of water, 2 cm³ of 5M sodium hydroxide and 30 cm³ of ethyl acetate. After decanting, the aqueous phase is washed with 10 cm³ of ethyl ether. It is then acidified, while stirring, with a 5M hydrochloric acid solution (pH=4) then extracted twice with 20 cm³ of dichloromethane. The organic phases are combined, dried over magnesium sulfate, filtered and concentrated using a rotary evaporator under reduced pressure (5 kPa). 114 mg of 2-(2-ethoxyethyl)-1-oxo-1,2,3,4-tetrahydroisoquinoline-5-carboxylic acid are obtained in the form of a beige powder.

NMR: 1.09 (t, J=7.1 Hz, 3 H) 3.29 (t, J=6.6 Hz, 2 H) 3.45 (q, J=7.1 Hz, 2 H) 3.56 (m, 4 H) 3.63 (m, 2 H) 7.44 (t, J=7.8 Hz, 1 H) 7.97 (d, J=7.8 Hz, 1 H) 8.08 (d, J=7.8 Hz, 1 H) 13.04 (broad unresolved m, 1 H)

ES-MS: m/z=264=MH$^+$; m/z=218=(M-OC$_2$H$_6$)$^+$; m/z=286=MNaH$^+$ 8.1.3: N-[(1S,2R)-1-(3,5-Difluorobenzyl)-2-hydroxy-3-({1-[3-(trifluoromethyl)phenyl]cyclopropyl}amino)propyl]-2-(2-ethoxyethyl)-1-oxo-1,2,3,4-tetrahydroisoquinoline-5-carboxamide Poured into a suspension of 255 mg of (2R,3S)-3-amino-4-(3,5-difluorophenyl)-1-({1-[3-(trifluoromethyl)phenyl]cyclopropyl}amino)butan-2-ol hydrochloride (2:1), 113.5 mg of 2-(2-ethoxyethyl)-1-oxo-1,2,3,4-tetrahydroisoquinoline-5-carboxylic acid, 9 mg of hydroxybenzotriazole, 104 mg of 1-(3-dimethylaminopropyl)-3-ethylcarbodiimide hydrochloride in 7.6 cm³ of dichloromethane is 0.3 cm³ of N,N-diisopropylethylamine at a temperature close to 20° C. The reaction mixture is kept stirring for 20 h at a temperature close to 20° C. The suspension obtained is filtered and the precipitate is washed once with 5 cm³ of dichloromethane, twice with 5 cm³ of diisopropyl ether, then dried under vacuum. 82 mg of N-[(1S,2R)-1-(3,5-difluorobenzyl)-2-hydroxy-3-({1-[3-(trifluoromethyl)phenyl]cyclopropyl}amino)propyl]-2-(2-ethoxyethyl)-1-oxo-1,2,3,4-tetrahydroisoquinoline-5-carboxamide are obtained in the form of a white powder.

LC-MS-DAD-ELSD: [M+H]$^+$: m/z 646; [M+H]$^-$: m/z 644

8.2: Salt N-[(1S,2R)-1-(3,5-difluorobenzyl)-2-hydroxy-3-({1-[3-(trifluoromethyl)phenyl]cyclopropyl}amino)propyl]-2-(2-ethoxyethyl)-1-oxo-1,2,3,4-tetrahydroisoquinoline-5-carboxamide hydrochloride (1:1)

82 mg of N-[(1S,2R)-1-(3,5-difluorobenzyl)-2-hydroxy-3-({1-[3-(trifluoromethyl)phenyl]cyclopropyl}amino)propyl]-2-(2-ethoxyethyl)-1-oxo-1,2,3,4-tetrahydroisoquinoline-5-carboxamide and 1 cm³ of a 2M solution of hydrochloric acid in ethyl ether are stirred at a temperature close to 20° C., under argon. The stirring is stopped and the ethyl ether is drawn off. The paste obtained is dried under vacuum at a temperature of 40° C. 86 mg of N-[(1S,2R)-1-(3,5-difluorobenzyl)-2-hydroxy-3-({1-[3-(trifluoromethyl)

phenyl]cyclopropyl}amino)propyl]-2-(2-ethoxyethyl)-1-oxo-1,2,3,4-tetrahydroisoquinoline-5-carboxamide hydrochloride (1:1) are obtained in the form of a white powder.

NMR: 1.09 (t, J=J=7.0 Hz, 3 H); from 1.20 to 1.40 (m, 2 H); from 1.48 to 1.65 (m, 2 H); from 2.30 to 2.85 (partially masked m, 4 H); from 2.97 to 3.72 (partially masked m, 10 H); 3.80 (m, 1 H); 4.12 (m, 1 H); 5.84 (broad m, 1 H); 6.93 (m, 2 H); 7.03 (m, 2 H); 7.34 (t, J=7.5 Hz, 1 H); 7.69 (t, J=7.5 Hz, 1 H); 7.81 (broad d, J=7.5 Hz, 1 H); 7.89 (broad d, J=7.5 Hz, 1 H); 7.92 (broad d, J=7.5 Hz, 1 H); 8.02 (broad s, 1 H); 8.29 (d, J=8.5 Hz, 1 H); 9.35 (broad m, 1 H); 9.60 (broad m, 1 H)

ES-MS: m/z: 646=MH$^+$; m/z: 668=MNaH$^+$

EXAMPLE 9

9.1: Base N-[(1S,2R)-1-(3,5-Difluorobenzyl)-2-hydroxy-3-({1-[3-(trifluoromethyl)phenyl]cyclopropyl}amino)propyl]-7-[methyl(methylsulfonyl)amino]-1-oxo-2-(1-propylbutyl)-1,2,3,4-tetrahydroisoquinoline-5-carboxamide 9.1.1: Methyl 1-oxo-2-(1-propylbutyl)-1,2,3,4-tetrahydroisoquinoline-5-carboxylate Introduced successively, at a temperature close to 20° C., into a three-necked flask that is stirred and purged using carbon monoxide are 10 g of 5-bromo-2-(1-propylbutyl)-3,4-dihydroisoquinolin-1(2H)-one, 65 cm$^3$ of methanol and 130 cm$^3$ of dimethylformamide. 1.354 g of [1,1'-bis(diphenylphosphino)ferrocene]dichloropalladium are added to the reaction medium and 10.5 cm$^3$ of N,N-diisopropylethylamine are poured into the reaction mixture. The latter is subjected to a carbon monoxide bubbling, then is heated at 70° C. for 20 h. The reaction mixture is cooled to a temperature close to 0° C., purged with argon, poured over a mixture containing 300 cm$^3$ of a 0.5M aqueous solution of hydrochloric acid and 1000 cm$^3$ of ethyl acetate before being filtered through a Celite 545 pellet. After decanting the filtrate, the organic phase is washed with 5 lots of 100 cm$^3$ of water, then 2 lots of 100 cm$^3$ of a saturated aqueous solution of sodium chloride, it is dried over magnesium sulfate and concentrated using a rotary evaporator under reduced pressure (5 kPa). The 12.5 g of product obtained are purified by flash chromatography over silica (column: 400 g; particle size: 15-40 μm; eluent: 50% heptane/50% ethyl acetate). After concentrating the fractions under reduced pressure, 8.8 g of methyl 1-oxo-2-(1-propylbutyl)-1,2,3,4-tetrahydroisoquinoline-5-carboxylate are obtained in the form of a yellow oil.

NMR: 0.87 (t, J=7.1 Hz, 6 H) 1.13-1.30 (m, 4 H) 1.41 (m, 2 H) 1.51 (m, 2 H) 3.22 (m, 2 H) 3.30 (m, 2 H) 3.85 (s, 3 H) 4.66 (m, 1 H) 7.47 (t, J=7.8 Hz, 1 H) 7.98 (dd, J=7.8, 1.5 Hz, 1 H) 8.13 (dd, J=7.8, 1.5 Hz, 1 H)

EI: m/z=303=M$^+$; m/z=260=(M-C$_3$H$_7$)$^+$; m/z=145=(m/z=260-COOCH$_3$CHC$_3$H$_7$)$^+$

ES: m/z=304=MH$^+$; m/z=326=MNaH$^+$; m/z=367=MACNH$^+$; m/z=629=(2MNaH$^+$)

9.1.2: Methyl 7-nitro-1-oxo-2-(1-propylbutyl)-1,2,3,4-tetrahydroisoquinoline-5-carboxylate 7.9 g of methyl 1-oxo-2-(1-propylbutyl)-1,2,3,4-tetrahydroisoquinoline-5-carboxylate are dissolved under an inert atmosphere in 60 cm$^3$ of concentrated (95%) sulfuric acid at a temperature close to 20° C. The reaction mixture is cooled to a temperature close to 0° C., then 12 cm$^3$ of nitric acid are introduced over 1 h. The temperature is kept close to 0° C. for 3 h, then 12 cm$^3$ of nitric acid are again introduced over 1 h. The reaction mixture is kept stirring at a temperature of less than 5° C. for 8 h before being poured into a mixture containing 100 g of ice and 100 cm$^3$ of water. The aqueous phase is extracted with 700 cm$^3$ of dichloromethane. After decanting, the organic phase is washed with 2 lots of 100 cm$^3$ of a saturated aqueous solution of sodium chloride, dried over magnesium sulfate then concentrated using a rotary evaporator under reduced pressure (5 kPa). The 9 g of crude product obtained are purified by trituration in 50 cm$^3$ of hot diisopropyl ether. After filtering at a temperature close to 20° C., washing with 2 lots of 20 cm$^3$ of diisopropyl ether and drying under vacuum, 8.6 g of methyl 7-nitro-1-oxo-2-(1-propylbutyl)-1,2,3,4-tetrahydroisoquinoline-5-carboxylate are obtained in the form of beige crystals.

NMR: 4.66 (tt, J=10.0, 4.9 Hz, 1 H) 8.69 (d, J=2.9 Hz, 1 H) 8.78 (d, J=2.9 Hz, 1 H)

ES: m/z: 349=MH$^+$; m/z: 390=MACNH$^+$(acetonitrile); m/z: 719=(2MNaH$^+$); m/z: 697=2MH$^+$ 9.1.3: Methyl 7-amino-1-oxo-2-(1-propylbutyl)-1,2,3,4-tetrahydroisoquinoline-5-carboxylate 8.6 g of 7-nitro-1-oxo-2-(1-propylbutyl)-1,2,3,4-tetrahydroisoquinoline-5-carboxylate, 10 cm$^3$ of methanol and 28 mg of 10% (dry basis) palladium-on-carbon are stirred under 2 bar of hydrogen in an autoclave for 2 h 20 min at a temperature of 25° C. The catalyst is filtered through a Celite 545 pellet and washed with 2 lots of 100 cm$^3$ of methanol. The filtrate is then concentrated under reduced pressure (5 kPa). 7.7 g of methyl 7-amino-1-oxo-2-(1-propylbutyl)-1,2,3,4-tetrahydroisoquinoline-5-carboxylate are obtained in the form of a light green powder.

NMR: 0.86 (t, J=7.1 Hz, 6 H) 1.13-1.29 (m, 4 H) 1.38 (m, 2 H) 1.49 (m, 2 H) 3.01 (t, J=6.4 Hz, 2 H) 3.20 (t, J=6.4 Hz, 2 H) 3.80 (s, 3 H) 4.64 (m, 1 H) 5.39 (s, 2 H) 7.22 (d, J=2.9 Hz, 1 H) 7.38 (d, J=2.9 Hz, 1 H)

ES: m/z: 319=MH$^+$; m/z: 360=MACNH$^+$; m/z: 659=(2MNaH$^+$); m/z: 637=2MH$^+$ 9.1.4: Methyl 7-[(methylsulfonyl)amino]-1-oxo-2-(1-propylbutyl)-1,2,3,4-tetrahydroisoquinoline-5-carboxylate 0.5 g of methyl 7-amino-1-oxo-2-(1-propylbutyl)-1,2,3,4-tetrahydroisoquinoline-5-carboxylate is dissolved under an inert atmosphere in 5 cm$^3$ of dichloromethane at a temperature close to 20° C. 0.142 cm$^3$ of pyridine is poured into the reaction mixture which is then cooled to a temperature close to 5° C. 0.122 cm$^3$ of methanesulfonyl chloride is introduced over 30 min. The stirring is continued for 20 h while gradually allowing it to climb back up to a temperature close to 20° C. 20 cm$^3$ of a saturated aqueous solution of sodium hydrogen carbonate and 5 cm$^3$ of water are added to the reaction mixture. Stirring is continued for 1 h at a temperature close to 20° C. The aqueous phase is extracted with 10 cm$^3$ of dichloromethane. After decanting, the organic phase is dried over magnesium sulfate, filtered then concentrated using a rotary evaporator under reduced pressure (5 kPa). The crude product obtained is purified by trituration in 10 cm$^3$ of hot diisopropyl ether. After filtering at a temperature close to 20° C., washing with 2 lots of 5 cm$^3$ of diisopropyl ether and drying under vacuum, 0.6 g of methyl 7-[(methylsulfonyl)amino]-1-oxo-2-(1-propylbutyl)-1,2,3,4-tetrahydroisoquinoline-5-carboxylate is obtained in the form of pink crystals.

NMR: 0.86 (t, J=7.1 Hz, 6 H) 1.21 (m, 4 H) 1.34-1.58 (m, 4 H) 3.00 (s, 3 H) 3.16 (m, 2 H) 3.29 (masked m, 2 H) 3.85 (s, 3 H) 4.62 (m, 1 H) 7.86 (s, 1 H) 8.00 (s, 1 H) 9.99 (s, 1 H)

ES: m/z: 397=MH$^+$; m/z: 816=(2MNaH$^+$); m/z: 793=2MH$^+$

9.1.5: Methyl 7-[methyl(methylsulfonyl)amino]-1-oxo-2-(1-propylbutyl)-1,2,3,4-tetrahydroisoquinoline-5-carboxylate 1.4 g of methyl 7-[(methylsulfonyl)amino]-1-oxo-2-(1-propylbutyl)-1,2,3,4-tetrahydroisoquinoline-5-carboxylate is dissolved under an inert atmosphere in 18 cm$^3$ of dimethylformamide at a temperature close to 20° C. This solution is cooled to a temperature close to 0° C., then 141 mg of sodium hydride (60% in oil) are added in 2 lots. The reaction mixture is stirred for 2 h at a temperature close to 0° C. 0.264 cm$^3$ of iodomethane is introduced then the stirring is continued for 20 h while gradually allowing it to climb back up to a temperature close to 20° C. 20 cm$^3$ of iced water and 50 cm$^3$ of ethyl acetate are added to the reaction mixture. After decanting, the organic phase is washed with 20 cm$^3$ of a 2M aqueous solution of hydrochloric acid, 3 lots of 20 cm$^3$ of water then 30 cm$^3$ of a saturated aqueous solution of sodium chloride. It is then dried over magnesium sulfate, filtered then concentrated using a rotary evaporator under reduced pressure (5 kPa). 1.187 g of methyl 7-[methyl(methylsulfonyl)amino]-1-oxo-2-(1-propylbutyl)-1,2,3,4-tetrahydroisoquinoline-5-carboxylate are obtained in the form of beige crystals.

NMR: 0.87 (t, J=7.3 Hz, 6 H) 1.14-1.31 (m, 4 H) 1.34-1.45 (m, 2 H) 1.49-1.60 (m, 2 H) 2.99 (s, 3 H) 3.21 (t, J=6.5 Hz, 2 H) 3.29 (s, 3 H) 3.33 (t, J=6.5 Hz, 2 H) 3.87 (s, 3 H) 4.66 (m, 1 H) 7.97 (d, J=2.6 Hz, 1 H) 8.13 (d, J=2.6 Hz, 1 H)

ES: m/z: 411=MH$^+$; m/z: 455=(MHCOO$^-$)

9.1.6: 7-[Methyl(methylsulfonyl)amino]-1-oxo-2-(1-propylbutyl)-1,2,3,4-tetrahydroisoquinoline-5-carboxylic acid 0.25 g of methyl 7-[methyl(methylsulfonyl)amino]-1-oxo-2-(1-propylbutyl)-1,2,3,4-tetrahydroisoquinoline-5-carboxylate is dissolved in 5 cm$^3$ of dioxane at a temperature close to 20° C. 1.52 cm$^3$ of a 1M aqueous solution of sodium hydroxide are added, then the reaction mixture is heated at a temperature close to 60° C. for 1 h. The dioxane contained in the reaction mixture is concentrated using a rotary evaporator under reduced pressure (5 kPa). 20 cm$^3$ of ethyl ether and 10 cm$^3$ of water are added to the residue obtained. After decanting, the aqueous phase is acidified with 1.6 cm$^3$ of a 1M aqueous solution of hydrochloric acid. The aqueous phase is extracted with 20 cm$^3$ of dichloromethane. After decanting, the organic phase is dried over magnesium sulfate, filtered then concentrated using a rotary evaporator under reduced pressure (5 kPa). 0.233 g of 7-[methyl(methylsulfonyl)amino]-1-oxo-2-(1-propylbutyl)-1,2,3,4-tetrahydroisoquinoline-5-carboxylic acid is obtained in the form of a pale pink powder.

NMR: 0.87 (t, J=7.3 Hz, 6 H) 1.13-1.30 (m, 4 H) 1.35-1.45 (m, 2 H) 1.42-1.57 (m, 2 H) 2.98 (s, 3 H) 3.25 (m, 4 H) 3.28 (s, 3 H) 4.66 (m, 1 H) 7.97 (d, J=2.6 Hz, 1 H) 8.09 (d, J=2.6 Hz, 1 H) 13.35 (broad unresolved m, 1 H)

ES: m/z=397=MH$^+$; m/z=419=MNaH$^+$; m/z=815=(2MNaH$^+$); m/z=793=2MH$^+$

9.1.7: N-[(1S,2R)-1-(3,5-difluorobenzyl)-2-hydroxy-3-({1-[3-(trifluoromethyl)phenyl]cyclopropyl}amino)propyl]-7-[methyl(methylsulfonyl)amino]-1-oxo-2-(1-propylbutyl)-1,2,3,4-tetrahydroisoquinoline-5-carboxamide Poured into a suspension of 233 mg of (2R,3S)-3-amino-4-(3,5-difluorophenyl)-1-({1-[3-(trifluoromethyl)phenyl]cyclopropyl}amino)butan-2-ol hydrochloride (2:1), 278 mg of 7-[methyl(methylsulfonyl)amino]-1-oxo-2-(1-propylbutyl)-1,2,3,4-tetrahydroisoquinoline-5-carboxylic acid, 12 mg of hydroxybenzotriazole and 142 mg of 1-(3-dimethylaminopropyl)-3-ethylcarbodiimide hydrochloride in 10 cm$^3$ of dichloromethane is 0.4 cm$^3$ of N,N-diisopropylethylamine at a temperature close to 20° C. The solution is kept stirring for 20 h at a temperature close to 20° C. 20 cm$^3$ of water are added to the reaction medium. After decanting, the organic phase is filtered through a pellet of 15 g of 40-63 μm silica. The silica pellet is washed firstly with 150 cm$^3$ of dichloromethane then secondly with 150 cm$^3$ of a mixture of 50% ethyl acetate/50% dichloromethane. This second filtrate is concentrated using a rotary evaporator under reduced pressure (5 kPa). 330 mg of N-[(1S,2R)-1-(3,5-difluorobenzyl)-2-hydroxy-3-({1-[3-(trifluoromethyl)phenyl]cyclopropyl}amino)propyl]-7-[methyl(methylsulfonyl)amino]-1-oxo-2-(1-propylbutyl)-1,2,3,4-tetrahydroisoquinoline-5-carboxamide are obtained in the form of a white foam.

NMR: 0.86 (t, J=7.5 Hz, 3 H) 0.87 (t, J=7.5 Hz, 3 H) 0.94-1.09 (m, 4 H) 1.20 (m, 4 H) 1.33-1.56 (m, 4 H) 2.45-2.54 (partially masked m, 3 H) 2.64 (m, 2 H) 2.72 (broad unresolved m, 1 H) 2.96 (s, 3 H) 3.03-3.13 (m, 3 H) 3.22 (s, 3 H) 3.55 (m, 1 H) 4.14 (m, 1 H) 4.64 (m, 1 H) 4.95 (d, J=5.8 Hz, 1 H) 6.95 (m, 2 H) 7.05 (tt, J=9.5, 1.9 Hz, 1 H) 7.18 (d, J=2.5 Hz, 1 H) 7.47-7.55 (m, 2 H) 7.59 (m, 1 H) 7.68 (s, 1 H) 7.90 (d, J=2.5 Hz, 1 H) 8.22 (d, J=9.3 Hz, 1 H)

LC-MS-DAD-ELSD: [M+H]+m/z=779; [M−H]−m/z=777

9.2: Salt N-[(1S,2R)-1-(3,5-difluorobenzyl)-2-hydroxy-3-({1-[3-(trifluoromethyl)phenyl]cyclopropyl}amino)propyl]-7-[methyl(methylsulfonyl)amino]-1-oxo-2-(1-propylbutyl)-1,2,3,4-tetrahydroisoquinoline-5-carboxamide hydrochloride (1:1)

330 mg of N-[(1S,2R)-1-(3,5-difluorobenzyl)-2-hydroxy-3-({1-[3-(trifluoromethyl)phenyl]cyclopropyl}amino)propyl]-7-[methyl(methylsulfonyl)amino]-1-oxo-2-(1-propylbutyl)-1,2,3,4-tetrahydroisoquinoline-5-carboxamide are dissolved in 10 cm$^3$ of ethyl ether at a temperature close to 20° C. 1 cm$^3$ of a 2M solution of hydrochloric acid in ethyl ether is added, while stirring under argon, at a temperature of 20° C. The reaction mixture precipitates. The solid is filtered, washed with 5 cm$^3$ of ethyl ether and dried under vacuum at a temperature of 35° C. for 3 h. 310 mg of N-[(1S,2R)-1-(3,5-difluorobenzyl)-2-hydroxy-3-({1-[3-(trifluoromethyl)phenyl]cyclopropyl}amino)propyl]-7-[methyl(methylsulfonyl)amino]-1-oxo-2-(1-propylbutyl)-1,2,3,4-tetrahydroisoquinoline-5-carboxamide hydrochloride (1:1) are obtained in the form of a white powder.

NMR: for this batch, all the signals are broad with: 0.88 (m, 6 H); from 1.11 to 1.67 (m, 12 H); from 2.35 to 3.40 (partially masked m, 8 H); 2.99 (s, 3 H); 3.26 (s, 3 H); 3.83 (m, 1 H); 4.12 (m, 1 H); 4.65 (m, 1 H); 5.88 (m, 1 H); 6.97 (d, J=9.5 Hz, 2 H); 7.10 (t, J=9.5 Hz, 1 H); 7.22 (d, J=2.0 Hz, 1 H); 7.69 (t, J=8.0 Hz, 1 H); 7.80 (d, J=8.0 Hz, 1 H); 7.90 (d, J=8.0 Hz, 1 H); 7.92 (d, J=2.0 Hz, 1 H); 8.00 (s, 1 H); 8.39 (d, J=8.5 Hz, 1 H); 9.38 (broad unresolved m, 1 H); 9.69 (broad unresolved m, 1 H)

ES: m/z=779=MH$^+$; m/z=778=MH$^-$; m/z=823=(MH-COO$^-$)

EXAMPLE 10

10.1: Base N-[(1S,2R)-1-(3,5-difluorobenzyl)-2-hydroxy-3-({1-[3-(trifluoromethyl)phenyl]cyclopropyl}amino)propyl]-2-[1-(4-fluorophenyl)ethyl]-1-oxo-1,2,3,4-tetrahydroisoquinoline-5-carboxamide

10.1.1: 1-(1-Bromoethyl)-4-fluorobenzene 0.5 g of 1-(4-fluorophenyl)ethanol is dissolved in 20 cm$^3$ of dichloromethane, under an inert atmosphere, at a temperature close to 20° C. 1.24 cm$^3$ of pure bromo(trimethyl)silane are introduced in two lots to the reaction mixture. The latter is stirred at a temperature close to 20° C. for 48 h, then it is washed with a saturated aqueous solution of sodium chloride, dried over a phase separation cartridge and concentrated using a rotary evaporator under reduced pressure (5 kPa). The 700 mg of crude product obtained are purified by filtration through a silica pellet (eluent: 10% ethyl acetate/90% cyclohexane). After concentrating the fractions under reduced pressure, 439 mg of 1-(1-bromoethyl)-4-fluorobenzene are obtained in the form of a colorless thick oil.

NMR: ppm: 1.98 (d, J=6.8 Hz, 3 H) 5.53 (q, J=6.8 Hz, 1 H) 7.19 (t, J=8.8 Hz, 2 H) 7.56 (dd, J=8.8, 5.4 Hz, 2 H)

EI: [M]$^+$ m/z=202; [M-Br]$^+$ m/z=123

10.1.2: Methyl[2-(2-bromophenyl)ethyl]carbamate 5 g of 2-(2-bromophenyl)ethanamine and 10 g of potassium carbonate in 30 cm$^3$ of anhydrous tetrahydrofuran are stirred under an inert atmosphere at a temperature close to 10° C. 2.5 cm$^3$ of methyl chlorocarbonate in solution in 10 cm$^3$ of tetrahydrofuran are poured into the reaction mixture. After returning to a temperature close to 20° C., the reaction mixture is heated for 2 h at the reflux of the solvent. The potassium carbonate is filtered and washed with tetrahydrofuran. The filtrate is concentrated using a rotary evaporator under reduced pressure (5 kPa). 3.43 g of methyl[2-(2-bromophenyl)ethyl]carbamate are obtained in the form of a colorless thick oil NMR: 2.85 (t, J=6.5 Hz, 2 H); 3.22 (q, J=6.5 Hz, 2 H); 3.51 (s, 3 H); 7.18 (m, 1 H); 7.22 (broad t, J=6.5 Hz, 1 H); 7.31 (m, 2 H); 7.59 (d, J=8.0 Hz, 1 H)

10.1.3: 5-Bromo-3,4-dihydroisoquinolin-1(2H)-one 1.36 g of methyl[2-(2-bromophenyl)ethyl]carbamate and 5.2 g of phosphoric acid are stirred under an inert atmosphere at a temperature close to 150° C. The reaction mixture is cooled to a temperature close to 20° C., then it is hydrolysed with a mixture of water and ethyl acetate using ultrasound treatment. After decanting, the organic phase is washed with a saturated aqueous solution of sodium hydrogen carbonate, water, a saturated aqueous solution of sodium chloride, then concentrated using a rotary evaporator under reduced pressure (5 kPa). 0.105 g of 5-bromo-3,4-dihydroisoquinolin-1(2H)-one is obtained in the form of an amorphous beige solid.

NMR: 2.98 (t, J=6.5 Hz, 2 H); 3.40 (dt, J=3.5 and 6.5 Hz, 2 H); 7.30 (t, J=8.0 Hz, 1 H); 7.78 (broad d, J=8.0 Hz, 1 H); 7.89 (broad d, J=8.0 Hz, 1 H); 8.05 (broad s, 1 H)

10.1.4: 5-Bromo-2-[1-(4-fluorophenyl)ethyl]-3,4-dihydroisoquinolin-1(2H)-one A solution of 0.15 g of 5-bromo-3,4-dihydroisoquinolin-1(2H)-one in 5 cm$^3$ of dimethylformamide is poured into a mixture containing 31 mg of sodium hydride (60% in oil) and 10 cm$^3$ of dimethylformamide at a temperature close to 20° C. under an inert atmosphere. Then a solution of 0.2 g of 1-(1-bromoethyl)-4-fluorobenzene in 5 cm$^3$ of dimethylformamide is poured into the reaction mixture. The latter is stirred for 20 h at a temperature close to 20° C. Water and ethyl acetate are added to the reaction mixture. After decanting, the organic phase is washed with a saturated aqueous solution of sodium chloride, dried over magnesium sulfate, filtered then concentrated using a rotary evaporator under reduced pressure (5 kPa). The 325 mg of crude product obtained are purified by filtration through a silica pellet (eluent: 20% ethyl acetate/80% cyclohexane). After concentrating the fractions under reduced pressure, 146 mg of 5-bromo-2-[1-(4-fluorophenyl)ethyl]-3,4-dihydroisoquinolin-1(2H)-one are obtained in the form of a thick pale yellow oil.

NMR: ppm: 1.54 (d, J=7.3 Hz, 3 H) 2.85 (m, 1 H) 2.97 (m, 1 H) 3.10 (m, 1 H) 3.47 (m, 1 H) 5.92 (q, J=7.3 Hz, 1 H) 7.18 (t, J=8.8 Hz, 2 H) 7.33 (t, J=8.1 Hz, 1 H) 7.41 (dd, J=8.8, 5.9 Hz, 2 H) 7.78 (dd, J=8.1, 1.4 Hz, 1 H) 7.98 (dd, J=8.1, 1.4 Hz, 1 H)

LC-MS-DAD-ELSD: [M+H]$^+$ m/z=348

10.1.5: 2-[1-(4-Fluorophenyl)ethyl]-1-oxo-1,2,3,4-tetrahydroisoquinoline-5-carboxylic acid Introduced successively, at a temperature close to 20° C., into a three-necked flask that is stirred and purged using carbon monoxide are 0.53 g of 5-bromo-2-[1-(4-fluorophenyl)ethyl]-3,4-dihydroisoquinolin-1(2H)-one, 12 cm$^3$ of dimethylformamide, 0.7 cm$^3$ of water, 0.570 g of potassium acetate, 253 mg of potassium iodide, 68 mg of palladium acetate and 160 mg of triphenylphosphine. The reaction mixture is subjected to a carbon monoxide bubbling, then is heated at 100° C. for 5 h. The reaction mixture is cooled to 20° C. and stirred for 20 h. The reaction mixture is again subjected to a carbon monoxide bubbling, then is heated at 100° C. for 3 h. It is cooled to 20° C., filtered, rinsed with dimethylformamide and the filtrate is evaporated using a rotary evaporator under reduced pressure (5 kPa). The residue obtained is taken up in 5 cm$^3$ of 5M sodium hydroxide and ethyl acetate. After decantation, the organic phase is extracted with water. The aqueous phases are combined, acidified with 5 cm$^3$ of 5M hydrochloric acid (pH=4-5) then extracted with ethyl acetate. The organic phase is washed with water, with a saturated aqueous solution of sodium chloride, dried over magnesium sulfate, filtered then concentrated using a rotary evaporator under reduced pressure (5 kPa). 0.375 g of 2-[1-(4-fluorophenyl)ethyl]-1-oxo-1,2,3,4-tetrahydroisoquinoline-5-carboxylic acid is obtained in the form of a thick pale yellow oil.

NMR: 1.54 (d, J=7.0 Hz, 3 H) 3.02-3.44 (m, 4 H) 5.94 (q, J=7.0 Hz, 1 H) 7.18 (t, J=8.8 Hz, 2 H) 7.41 (dd, J=8.8, 5.4 Hz, 2 H) 7.46 (t, J=7.8 Hz, 1 H) 7.98 (dd, J=7.8, 1.5 Hz, 1 H) 8.15 (dd, J=7.8, 1.5 Hz, 1 H) 12.85 (broad unresolved m, 1 H)

LC-MS-DAD-ELSD: [M+H]+m/z=314; [M-H]-m/z=312

10.1.6: N-[(1S,2R)-1-(3,5-difluorobenzyl)-2-hydroxy-3-({1-[3-(trifluoromethyl)phenyl]cyclopropyl}amino)propyl]-2-[1-(4-fluorophenyl)ethyl]-1-oxo-1,2,3,4-tetrahydroisoquinoline-5-carboxamide Added to a suspension of 133 mg of 2-[1-(4-fluorophenyl)ethyl]-1-oxo-1,2,3,4-tetrahydroisoquinoline-5-carboxylic acid in 20 cm$^3$ of dichloromethane are 200 mg of (2R,3S)-3-amino-4-(3,5-difluorophenyl)-1-({1-[3-(trifluoromethyl)

phenyl]cyclopropyl}amino)butan-2-ol hydrochloride (2:1) and 0.221 cm³ of N,N-diisopropylethylamine at a temperature close to 20° C. 5.7 mg of hydroxybenzotriazole, 5 mg of dimethylaminopyridine and 97 mg of 1-(3-dimethylaminopropyl)-3-ethylcarbodiimide hydrochloride are successively added. The solution is kept stirring for 6 h at a temperature close to 20° C. The reaction mixture is washed with water then a saturated aqueous solution of sodium chloride. It is dried over a phase separation cartridge and concentrated using a rotary evaporator under reduced pressure (5 kPa). The 290 mg of product obtained are purified by flash chromatography over silica (column: 25 g; particle size: 15-40 µm; eluent: 20% cyclohexane/80% ethyl acetate). After concentrating the fractions under reduced pressure, 0.202 g of N-[(1S,2R)-1-(3,5-difluorobenzyl)-2-hydroxy-3-({1-[3-(trifluoromethyl)phenyl]cyclopropyl}amino)propyl]-2-[1-(4-fluorophenyl)ethyl]-1-oxo-1,2,3,4-tetrahydroisoquinoline-5-carboxamide is obtained in the form of a whitish foam.

NMR: 1.19-1.39 (m, 2 H) 1.49-1.68 (m, 2 H) 1.51 (d, J=7.1 Hz, 1.5 H) 1.53 (d, J=7.1 Hz, 1.5 H) 2.19-3.28 (m, 8 H) 3.82 (m, 1 H) 4.07 (m, 1 H) 5.85 (broad unresolved m, 1 H) 5.93 (q, J=7.1 Hz, 1 H) 6.95-7.10 (m, 4 H) 7.19 (m, 2 H) 7.32-7.42 (m, 3 H) 7.61 (t, J=7.8 Hz, 0.5 H) 7.64 (t, J=7.8 Hz, 0.5 H) 7.72 (d, J=7.8 Hz, 0.5 H) 7.75 (d, J=7.8 Hz, 0.5 H) 7.86 (d, J=7.8 Hz, 0.5 H) 7.90 (d, J=7.8 Hz, 0.5 H) 7.96-8.03 (m, 2 H) 8.27 (d, J=9.0 Hz, 0.5 H) 8.29 (d, J=9.0 Hz, 0.5 H) 9.39 (broad m, 1 H) 9.92 (broad m, 1 H)

LC-MS-DAD-ELSD: [M+H]+m/z=696; [M−H]−m/z=694

10.2: Salt N-[(1S,2R)-1-(3,5-difluorobenzyl)-2-hydroxy-3-({1-[3-(trifluoromethyl)phenyl]cyclopropyl}amino)propyl]-2-[1-(4-fluorophenyl)ethyl]-1-oxo-1,2,3,4-tetrahydroisoquinoline-5-carboxamide hydrochloride (1:1)

202 mg of N-[(1S,2R)-1-(3,5-difluorobenzyl)-2-hydroxy-3-({1-[3-(trifluoromethyl)phenyl]cyclopropyl}amino)propyl]-2-[1-(4-fluorophenyl)ethyl]-1-oxo-1,2,3,4-tetrahydroisoquinoline-5-carboxamide are dissolved in a mixture containing ethyl ether and a few drops of methanol at a temperature close to 20° C. 5 cm³ of a 1M solution of hydrochloric acid in ethyl ether are added. The reaction mixture is concentrated using a rotary evaporator under reduced pressure (5 kPa). The solid obtained is triturated in diisopropyl ether, filtered and dried. 206 mg of N-[(1S,2R)-1-(3,5-difluorobenzyl)-2-hydroxy-3-({1-[3-(trifluoromethyl)phenyl]cyclopropyl}amino)propyl]-2-[1-(4-fluorophenyl)ethyl]-1-oxo-1,2,3,4-tetrahydroisoquinoline-5-carboxamide hydrochloride (1:1) are obtained in the form of an amorphous white solid.

NMR: for this batch, a 50%/50% mixture of isomers is obtained insofar as the following are observed: from 1.18 to 1.40 (m, 2 H); from 1.48 to 1.68 (m, 5 H); 2.20 to 3.28 (m, 8 H); 3.81 (m, 1 H); 4.09 (m, 1 H); 5.83 (broad unresolved m, 1 H); 5.93 (q, J=7.5 Hz, 1 H); from 6.95 to 7.10 (m, 4 H); 7.19 (t, J=9.0 Hz, 0.5 H); 7.20 (t, J=9.0 Hz, 0.5 H); from 7.30 to 7.42 (m, 3 H); 7.60 (t, J=7.6 Hz, 0.5 H); 7.65 (t, J=7.5 Hz, 0.5 H); 7.71 (d, J=7.5 Hz, 0.5 H); 7.75 (d, J=7.5 Hz, 0.5 H); 7.88 (d, J=7.5 Hz, 0.5 H); 7.90 (d, J=7.5 Hz, 0.5 H); 8.00 (m, 2 H); 8.27 (d, J=8.5 Hz, 0.5 H); 8.29 (d, J=8.5 Hz, 0.5 H); 9.40 (broad m, 1 H); 9.92 (broad m, 1 H)

MP: 157° C.

EXAMPLE 11

11.1 Base N-[(1S,2R)-1-(3,5-difluorobenzyl)-2-hydroxy-3-({1-[3-(trifluoromethyl)phenyl]cyclopropyl}amino)propyl]-6-[methyl(methylsulfonyl)amino]-1-oxo-2-(1-propylbutyl)isoindoline-3-methyl-4-carboxamide

11.1.1: Methyl 1-oxo-2-(1-propylbutyl)isoindoline-4-carboxylate

In a three-necked flask that is stirred and purged using carbon monoxide, 3.481 g of 4-bromo-2-(1-propylbutyl)isoindolin-1-one (prepared as in Example 1.1.2) are dissolved in a mixture of 40 cm³ of methanol and 80 cm³ of anhydrous dimethylformamide. 3.908 g of N,N-diisopropylethylamine and 493 mg of [1,1'-bis(diphenylphosphino)ferrocene] dichloropalladium are successively added. The reaction mixture is subjected to a carbon monoxide bubbling and it is heated at a temperature in the vicinity of 70° C. for 6 h 30 min. The reaction mixture is cooled to a temperature close to 0° C. and 180 cm³ of a 1M aqueous solution of hydrogen chloride and 1000 cm³ of ethyl acetate are successively added thereto. The mixture is filtered through a celite pellet. The organic phase is separated and is washed successively with 5×100 cm³ of distilled water and 2×100 cm³ of a saturated solution of sodium chloride. The organic phase is dried over magnesium sulfate and concentrated using a rotary evaporator under reduced pressure (5 kPa). The residual red oil is purified by column chromatography (silica 60 column—particle size 15-40 µm—200 g—eluent: 80% cyclohexane/20% ethyl acetate). The fractions are concentrated under reduced pressure (5 kPa). 1.92 g of methyl 1-oxo-2-(1-propylbutyl)isoindoline-4-carboxylate are obtained in the form of a yellow oil.

NMR: 0.86 (t, J=7.3 Hz, 6 H) 1.17 (m, 4 H) 1.49-1.70 (m, 4 H) 3.91 (s, 3 H) 4.27 (m, 1 H) 4.56 (s, 2 H) 7.67 (t, J=7.8 Hz, 1 H) 7.95 (dd, J=7.8, 1.3 Hz, 1 H) 8.15 (dd, J=7.8, 1.3 Hz, 1 H)

LC-MS-DAD-ELSD: [M+H]+m/z=290; [2M+Na]+m/z=601

11.1.2: Methyl 6-nitro-1-oxo-2-(1-propylbutyl)isoindoline-4-carboxylate

In a three-necked flask, 1.92 g of methyl 1-oxo-2-(1-propylbutyl)isoindoline-4-carboxylate are dissolved in 20 cm³ of concentrated sulfuric acid. The reaction mixture is cooled to a temperature in the vicinity of 0° C. Over 30 min, 3 cm³ of concentrated (60%—density 1.38) nitric acid are introduced while keeping the reaction medium at a temperature close to 0° C., then by letting it return to a temperature in the vicinity of 20° C. The mixture is left stirring at this temperature for 12 h, then again 2.60 cm³ of concentrated nitric acid are added, the stirring being continued for 2 h. The reaction medium is poured over a mixture of 30 g of ice and 30 cm³ of distilled water while stirring, then extracted using 200 cm³ of ethyl acetate. The organic phase is washed using 2×150 cm³ of a saturated solution of sodium chloride, dried over magnesium sulfate then concentrated using a rotary evaporator under reduced pressure (5 kPa). The residual yellow oil is purified by column chromatography (silica 60 column—particle size 15-40 µm—200 g—eluent: 80% cyclohexane/20% ethyl acetate). The fractions are concentrated under reduced pressure (5 kPa). 1.57 g of a mixture containing the methyl 6-nitro-1-oxo-2-(1-propylbutyl)isoindoline-4-carboxylate is obtained, which is used without purification in the following step.

NMR: 0.87 (t, J=7.3 Hz, 6 H) 1.18 (m, 4 H) 1.50-1.74 (m, 4 H) 3.97 (s, 3 H) 4.28 (m, 1 H) 4.71 (s, 2 H) 8.54 (d, J=2.4 Hz, 1 H) 8.77 (d, J=2.4 Hz, 1 H)

LC-MS-DAD-ELSD: [M+H]+m/z=335; [M−H]−m/z=333

11.1.3: Methyl 6-amino-1-oxo-2-(1-propylbutyl)isoindoline-4-carboxylate

In an autoclave, 1.52 g of methyl 6-nitro-1-oxo-2-(1-propylbutyl)isoindoline-4-carboxylate are dissolved in 15 cm³ of methanol. 100 mg of 5% palladium-on-carbon in suspension in 1 cm³ of methanol are added. The autoclave is placed under 2 bar of hydrogen pressure and the mixture is stirred for 5 min at a temperature in the vicinity of 25° C. The reaction medium is filtered through a celite pellet. The celite is rinsed using 2×10 cm³ of methanol, then the organic phase is concentrated using a rotary evaporator under reduced pressure (5 kPa). The residual yellow oil is purified by column chromatography (silica 60 column—particle size 15-40 μm—150 g—eluent: 60% cyclohexane/40% ethyl acetate). The fractions are concentrated under reduced pressure (5 kPa). 1.05 g of methyl 6-amino-1-oxo-2-(1-propylbutyl)isoindoline-4-carboxylate are obtained in the form of a pale yellow solid.

NMR: 0.85 (t, J=7.3 Hz, 6 H) 1.15 (m, 4 H) 1.45-1.67 (m, 4 H) 3.85 (s, 3 H) 4.20 (m, 1 H) 4.32 (s, 2 H) 5.63 (s, 2 H) 7.06 (d, J=2.4 Hz, 1 H) 7.38 (d, J=2.4 Hz, 1 H)

LC-MS-DAD-ELSD: [M+H]+m/z=305; [2M+H]+m/z=609

MP=114° C.

11.1.4: Methyl 6-[(methylsulfonyl)amino]-1-oxo-2-(1-propylbutyl)isoindoline-4-carboxylate In a three-necked flask, 500 mg of methyl 6-amino-1-oxo-2-(1-propylbutyl)isoindoline-4-carboxylate are dissolved in 5 cm³ of dichloromethane. 150 μl of pyridine are added and the reaction mixture is cooled to a temperature in the vicinity of 0° C. 188 mg of methanesulfonyl chloride are added over 15 min, then the mixture is left to return to a temperature in the vicinity of 25° C. and stirred for 12 h. 5 cm³ of distilled water and 20 cm³ of a saturated solution of sodium chloride are added successively and left stirring for 1 h at a temperature in the vicinity of 25° C. 10 cm³ of dichloromethane are added. The organic phase is separated, dried then concentrated using a rotary evaporator under reduced pressure (5 kPa). The residual yellow solid is triturated with 15 cm³ of hot diisopropyl ether. The mixture is left to return to a temperature in the vicinity of 25° C. The residual solid is filtered, then rinsed with 2×5 cm³ of diisopropyl ether. 574 mg of methyl 6-[(methylsulfonyl)amino]-1-oxo-2-(1-propylbutyl)isoindoline-4-carboxylate are obtained in the form of a beige solid.

NMR: 0.86 (t, J=7.3 Hz, 6 H) 1.16 (m, 4 H) 1.46-1.70 (m, 4 H) 3.03 (s, 3 H) 3.90 (s, 3 H) 4.24 (m, 1 H) 4.49 (s, 2 H) 7.73 (d, J=2.4 Hz, 1 H) 7.98 (d, J=2.4 Hz, 1 H) 10.19 (broad unresolved m, 1 H)

LC-MS-DAD-ELSD: [M+H]+m/z=383; [2M+H]+m/z=765 (base peak); [M−H]−m/z=381

MP=173° C.

11.1.5: Methyl 6-[methyl(methylsulfonyl)amino]-1-oxo-2-(1-propylbutyl)isoindoline-4-carboxylate and methyl 6-[methyl(methylsulfonyl)amino]-1-oxo-2-(1-propylbutyl)isoindoline-3-methyl-4-carboxylate In a three-necked flask, 500 mg of methyl 6-[(methylsulfonyl)amino]-1-oxo-2-(1-propylbutyl)isoindoline-4-carboxylate are dissolved in 10 cm³ of anhydrous dimethylformamide and the reaction mixture is cooled to a temperature in the vicinity of 0° C. 38 mg of a suspension of sodium hydride in oil are added and the reaction mixture is left stirring for 2 h at a temperature close to 0° C. 100 μl of methyl iodide are added using a syringe. The temperature is left to return to a temperature in the vicinity of 25° C. and the stirring is continued for 12 h. 38 mg of sodium hydride in suspension in oil are again added. After stirring for 30 min, at a temperature in the vicinity of 25° C., 100 μl of methyl iodide are again added. The medium is left stirring for 3 h at a temperature in the vicinity of 25° C. then 20 cm³ of distilled water and 20 cm³ of ethyl acetate are added. The organic phase is separated, washed successively with 20 cm³ of a 2N aqueous solution of hydrogen chloride, 3 lots of 20 cm³ of distilled water and 20 cm³ of a saturated solution of sodium chloride, dried then finally concentrated using a rotary evaporator under reduced pressure (5 kPa). The residual yellow solid is purified by column chromatography (silica 60 column—particle size: 15-40 μm—70 g—eluent: 60% cyclohexane/40% ethyl acetate—45 cm³/min). The fractions 15 to 23 and 27 to 42 are concentrated under reduced pressure (5 kPa) in order to result respectively in 170 mg of methyl 6-[methyl(methylsulfonyl)amino]-1-oxo-2-(1-propylbutyl)isoindoline-3-methyl-4-carboxylate:

NMR: 0.88 (t, J=7.3 Hz, 3 H) 0.89 (t, J=7.3 Hz, 3 H) 1.13-1.41 (m, 4 H) 1.45 (d, J=6.4 Hz, 3 H) 1.52-1.98 (m, 4 H) 3.00 (s, 3 H) 3.33 (s, 3 H) 3.86 (m, 1 H) 3.92 (s, 3 H) 4.92 (q, J=6.4 Hz, 1 H) 7.90 (d, J=2.4 Hz, 1 H) 8.07 (d, J=2.4 Hz, 1 H)

LC-MS-DAD-ELSD: [M+H]+m/z=411 (base peak); [2M+H]+m/z=821

MP=174° C.

and 284 mg of methyl 6-[methyl(methylsulfonyl)amino]-1-oxo-2-(1-propylbutyl)isoindoline-4-carboxylate:

MP=183° C.

11.1.6: 6-[Methyl(methylsulfonyl)amino]-1-oxo-2-(1-propylbutyl)isoindoline-3-methyl-4-carboxylic acid In a single-necked flask, 157 mg of methyl 6-[methyl(methylsulfonyl)amino]-1-oxo-2-(1-propylbutyl)isoindoline-3-methyl-4-carboxylate obtained in Example 11.1.5 after separation by column chromatography are dissolved in 5 cm³ of dioxane and 0.956 cm³ of a 1M sodium hydroxide solution is added. The reaction mixture is heated for 90 min at a temperature in the vicinity of 60° C. The reaction mixture is then concentrated to dryness using a rotary evaporator under reduced pressure (5 kPa). The residual solid is taken up in 20 cm³ of diethyl ether and 10 cm³ of distilled water. The aqueous phase is separated then acidified using 1.2 cm³ of a 1M aqueous solution of hydrogen chloride. A solid appears. It is treated with 2 lots of 20 cm³ of dichloromethane. The organic phase is dried then concentrated using a rotary evaporator under reduced pressure (5 kPa). 130 mg of 6-[methyl(methylsulfonyl)amino]-1-oxo-2-(1-propylbutyl)isoindoline-3-methyl-4-carboxylic acid are obtained in the form of a beige solid.

NMR: 0.88 (t, J=7.2 Hz, 3 H) 0.89 (t, J=7.2 Hz, 3 H) 1.17-1.42 (m, 4 H) 1.49 (d, J=6.4 Hz, 3 H) 1.53-2.00 (m, 4 H) 3.01 (s, 3 H) 3.33 (masked s, 3 H) 3.88 (m, 1 H) 4.93 (q, J=6.4 Hz, 1 H) 7.85 (d, J=2.2 Hz, 1 H) 8.06 (d, J=2.2 Hz, 1 H) 13.7 (very broad unresolved m, 1 H)

LC-MS-DAD-ELSD: [M+H]+m/z=397; [M−H]−m/z=395

MP=200° C.

11.1.7: N-[(1S,2R)-1-(3,5-difluorobenzyl)-2-hydroxy-3-({1-[3-(trifluoromethyl)phenyl]cyclopropyl}amino)propyl]-6-[methyl(methylsulfonyl)amino]-1-oxo-2-(1-propylbutyl)isoindoline-3-methyl-4-carboxamide Added, under an argon atmosphere and at a temperature close to 20° C., to a solution of 122 mg of 6-[methyl(methylsulfonyl)amino]-1-oxo-2-(1-propylbutyl)isoindoline-3-methyl-4-carboxylic acid and 1146 mg of (2R,3S)-3-amino-4-(3,5-difluorophenyl)-1-({1-[3-trifluoromethyl)phenyl]cyclopropyl}amino)butan-2-ol hydrochloride (2:1) in 15 cm$^3$ of dichloromethane are 0.215 cm$^3$ of N,N-diisopropylethylamine, 4 mg of 4-dimethylaminopyridine, then 6 mg of 1-hydroxy-7-azabenzotriazole and 74 mg of 1-(3-dimethylaminopropyl)-3-ethylcarbodiimide hydrochloride. The solution is kept stirring under argon for 15 h at a temperature close to 20° C. The reaction medium is then concentrated under reduced pressure (5 kPa). The residual solid is purified by flash chromatography over silica (column: 70 g; silica of the type SuperVarioPrep D40-Si60 particle size: 15-40 µm; eluent: 30% cyclohexane/70% ethyl acetate). After concentrating the fractions under reduced pressure, N-[(1S,2R)-1-(3,5-difluorobenzyl)-2-hydroxy-3-({1-[3-(trifluoromethyl)phenyl]cyclopropyl}amino)propyl]-6-[methyl(methylsulfonyl)amino]-1-oxo-2-(1-propylbutyl)isoindoline-3-methyl-4-carboxamide is obtained in the form of a beige foam.

11.2 Salt N-[(1S,2R)-1-(3,5-difluorobenzyl)-2-hydroxy-3-({1-[3-(trifluoromethyl)phenyl]cyclopropyl}amino)propyl]-6-[methyl(methylsulfonyl)amino]-1-oxo-2-(1-propylbutyl)isoindoline-3-methyl-4-carboxamide hydrochloride (1:1)

The foam obtained in Example 17.7 is dissolved in 10 cm$^3$ of diethyl ether. 3 cm$^3$ of a 1N solution of hydrochloric acid in ethyl ether, then 2 cm$^3$ of methanol are added, while stirring, at a temperature in the vicinity of 20° C. The reaction mixture is concentrated to dryness under reduced pressure (5 kPa). The residue is triturated with 5 cm$^3$ of diisopropyl ether, the solid formed is filtered, then dried under atmospheric pressure at a temperature close to 20° C. 198 mg of N-[(1S,2R)-1-(3,5-difluorobenzyl)-2-hydroxy-3-({1-[3-(trifluoromethyl)phenyl]cyclopropyl}amino)propyl]-6-[methyl(methylsulfonyl)amino]-1-oxo-2-(1-propylbutyl)isoindoline-3-methyl-4-carboxamide hydrochloride (1:1) hydrochloride are obtained in the form of a white solid.

NMR: 0.82-0.91 (m, 7.5 H) 0.97 (d, J=6.5 Hz, 1.5 H) 1.09-1.91 (m, 12 H) 2.58-2.87 (m, 2 H) 2.98-3.17 (m, 2 H) 3.02 (s, 1.5 H) 3.05 (s, 1.5 H) 3.31 (s, 1.5 H) 3.36 (s, 1.5 H) 3.78 (m, 1 H) 3.94 (m, 1 H) 4.14 (m, 1 H) 4.64 (q, J=6.5 Hz, 0.5 H) 4.70 (q, J=6.5 Hz, 0.5 H) 5.93 (broad m, 1 H) 6.85-7.08 (m, 3 H) 7.54 (d, J=2.4 Hz, 0.5 H) 7.58-8.00 (m, 5.5 H) 8.74 (d, J=9.3 Hz, 0.5 H) 8.81 (d, J=9.3 Hz, 0.5 H) 9.44 (broad m, 1 H) 9.74 (broad m, 0.5 H) 9.88 (broad m, 0.5 H)

LC-MS-DAD-ELSD: [M+H]+m/z=779

MP=193° C.

EXAMPLE 12

12.1 Base N-[(1S,2R)-1-(3,5-difluorobenzyl)-2-hydroxy-3-({1-[3-(trifluoromethyl)phenyl]cyclopropyl}amino)propyl]-6-[methyl(methylsulfonyl)amino]-1-oxo-2-(1-propylbutyl)isoindoline-4-carboxamide

12.1.1: 6-[Methyl(methylsulfonyl)amino]-1-oxo-2-(1-propylbutyl)isoindoline-4-carboxylic acid In a single-necked flask, 267 mg of methyl 6-[methyl(methylsulfonyl)amino]-1-oxo-2-(1-propylbutyl)isoindoline-4-carboxylate, obtained in Example 17.1.5 after separation by column chromatography, are dissolved in 7 cm$^3$ of dioxane and 1.68 cm$^3$ of a 1M solution of sodium hydroxide is added. The reaction mixture is heated for 90 min at a temperature in the vicinity of 60° C. The reaction mixture is then concentrated to dryness using a rotary evaporator under reduced pressure (5 kPa). The residual solid is taken up in 20 cm$^3$ of diethyl ether and 10 cm$^3$ of distilled water. The aqueous phase is separated then acidified using 1.8 cm$^3$ of a 1M aqueous solution of hydrogen chloride. A solid appears. It is treated with 2 lots of 20 cm$^3$ of dichloromethane. The organic phase is dried then concentrated using a rotary evaporator under reduced pressure (5 kPa). 257 mg of 6-[methyl(methylsulfonyl)amino]-1-oxo-2-(1-propylbutyl)isoindoline-4-carboxylic acid are obtained in the form of a beige solid.

NMR: 0.88 (t, J=7.3 Hz, 6 H) 1.19 (m, 4 H) 1.46-1.73 (m, 4 H) 3.01 (s, 3 H) 3.25-3.45 (masked s, 3 H) 4.27 (m, 1 H) 4.55 (s, 2 H) 7.92 (d, J=2.2 Hz, 1 H) 8.09 (d, J=2.2 Hz, 1 H) 12.0-14.0 (very broad unresolved m, 1 H)

LC-MS-DAD-ELSD: [M+H]+m/z=383; [M–H]–m/z=381

MP=206° C.

12.1.2:
Added, under an argon atmosphere and at a temperature close to 20° C., to a solution of 150 mg of 6-[methyl(methylsulfonyl)amino]-1-oxo-2-(1-propylbutyl)isoindoline-4-carboxylic acid and 185 mg of (2R,3S)-3-amino-4-(3,5-difluorophenyl)-1-({1-[3-trifluoromethyl)phenyl]cyclopropyl}amino)butan-2-ol hydrochloride (2:1) in 19 cm$^3$ of dichloromethane are 0.274 cm$^3$ of N,N-diisopropylethylamine, 5 mg of 4-dimethylaminopyridine, then 8 mg of 1-hydroxy-7-azabenzotriazole and 94 mg of 1-(3-dimethylaminopropyl)-3-ethylcarbodiimide hydrochloride. The solution is kept stirring under argon for 15 h at a temperature close to 20° C. The reaction medium is then concentrated under reduced pressure (5 kPa). The residual solid is purified by flash chromatography over silica (column: 70 g; silica of the type SuperVarioPrep D40-Si60 particle size: 15-40 µm; eluent: 30% cyclohexane/70% ethyl acetate). After concentrating the fractions under reduced pressure, N-[(1S,2R)-1-(3,5-difluorobenzyl)-2-hydroxy-3-({1-[3-(trifluoromethyl)phenyl]cyclopropyl}amino)propyl]-6-[methyl(methylsulfonyl)amino]-1-oxo-2-(1-propylbutyl)isoindoline-4-carboxamide is obtained in the form of a beige foam.

12.2: Salt N-[(1S,2R)-1-(3,5-difluorobenzyl)-2-hydroxy-3-({1-[3-(trifluoromethyl)phenyl]cyclopropyl}amino)propyl]-6-[methyl(methylsulfonyl)amino]-1-oxo-2-(1-propylbutyl)isoindoline-4-carboxamide hydrochloride (1:1)

The solid obtained in 17.1 is dissolved in 10 cm$^3$ of diethyl ether. 4 cm$^3$ of a 1N solution of hydrochloric acid in ethyl ether, then 1 cm$^3$ of methanol, are added while stirring at a temperature in the vicinity of 20° C. 2 cm$^3$ of methanol is added then the reaction mixture is concentrated to dryness under reduced pressure (5 kPa). The residue is triturated with 5 cm$^3$ of diisopropyl ether, the solid formed is filtered then dried under atmospheric pressure at a temperature close to 20° C. 203 mg of N-[(1S,2R)-1-(3,5-difluorobenzyl)-2-hydroxy-3-({1-[3-(trifluoromethyl)phenyl]cyclopropyl}amino)propyl]-6-[methyl(methylsulfonyl)amino]-1-oxo-2-(1-propylbutyl)isoindoline-4-carboxamide hydrochloride (1:1) are obtained in the form of a white solid.

NMR: 0.85 (t, J=7.3 Hz, 6 H) 1.06-1.65 (m, 12 H) 2.74 (m, 1 H) 2.87 (dd, J=14.2, 10.8 Hz, 1 H) 3.00-3.15 (m, 2 H) 3.04 (s, 3 H) 3.34 (s, 3 H) 3.96 (m, 1 H) 4.11 (m, 1 H) 4.22 (m, 1 H) 4.24 (s, 2 H) 5.91 (broad unresolved m, 1 H) 6.92-7.01 (m, 3

H) 7.60 (t, J=7.9 Hz, 1 H) 7.73 (d, J=7.9 Hz, 1 H) 7.82 (d, J=2.2 Hz, 1 H) 7.89 (d, J=7.9 Hz, 1 H) 7.91 (d, J=2.2 Hz, 1 H) 7.97 (s, 1 H) 8.70 (d, J=9.3 Hz, 1 H) 9.40 (broad m, 1 H) 9.69 (broad m, 1 H)

LC-MS-DAD-ELSD: [M+H]+m/z=765; [M−H]−m/z=763

MP=194° C.

EXAMPLE 13

13.1: Base N-[(1S,2R)-1-(3,5-difluorobenzyl)-2-hydroxy-3-({1-[3-(trifluoromethyl)phenyl]cyclopropyl}amino)propyl]-7-trifluoromethyl-1-oxo-2-(1-propylbutyl)-1,2,3,4-tetrahydroisoquinoline-5-carboxamide

13.1.1: N-[2-(2-bromo-4-trifluoromethylphenyl)ethyl]heptan-4-amine

Added to a suspension of 1 g of 2-bromo-4-trifluoromethylphenethylamine hydrocloride in 25 cm³ of dichloroethane and under an inert atmosphere is 0.5 cm³ of triethylamine. After stirring for 30 min at a temperature close to 20° C., 5 cm³ of distilled water are added and the stirring is continued for 30 min. The two phases are separated and the organic phase is dried. Added to the solution obtained are successively 375 mg of 4-heptanone and 970 mg of sodium triacetoxyborohydride. The reaction mixture is stirred for 15 h at a temperature close to 20° C. 20 cm³ of a saturated solution of sodium hydrogen carbonate are then added to the reaction medium. The organic phase is decanted and separated from the aqueous phase then washed successively with 15 cm³ of distilled water and 15 cm³ of a saturated solution of sodium chloride. The organic phase is dried then concentrated using a rotary evaporator under reduced pressure (5 kPa). 1.16 g of N-[2-(2-bromo-4-trifluoromethylphenyl)ethyl]heptan-4-amine are obtained in the form of a colorless oil.

NMR: 0.83 (m, 6 H) 1.25 (m, 8 H) 1.35 (broad s, 1 H) 2.44 (m, 1 H) 2.75 (t, J=7.3 Hz, 2 H) 2.88 (t, J=7.3 Hz, 2 H) 7.59 (d, J=8.1 Hz, 1 H) 7.68 (dd, J=8.1, 2.0 Hz, 1 H) 7.92 (d, J=2.0 Hz, 1 H)

LC-MS-DAD-ELSD: [M+H]+m/z=366

13.1.2: Methyl[2-(2-bromo-4-trifluoromethylphenyl)ethyl](1-propylbutyl)-carbamate 770 mg of N-[2-(2-bromo-4-trifluoromethylphenyl)ethyl]heptan-4-amine in solution in 15 cm³ of anhydrous tetrahydrofuran and 500 mg of potassium carbonate are stirred under an inert atmosphere at a temperature in the vicinity of 5° C. 0.19 cm³ of methyl chloroformate is introduced over 5 minutes into the reaction mixture. The reaction mixture is brought to reflux over 15 h, the insoluble material is separated by filtration and the filtrate is concentrated using a rotary evaporator under reduced pressure (5 kPa). The residual oil is purified by filtration through a silica pellet using a mixture of 10% ethyl acetate and 90% cyclohexane as eluent. The organic phase is then concentrated to dryness using a rotary evaporator under reduced pressure (5 kPa) in order to result in 666 mg of methyl[2-(2-bromo-4-trifluoromethylphenyl)ethyl](1-propylbutyl)carbamate in the form of a colorless oil.

NMR: 0.84 (t, J=7.3 Hz, 6 H) 1.17 (m, 4 H) 1.27-1.50 (m, 4 H) 3.02 (m, 2 H) 3.20 (m, 2 H) 3.63 (s, 3 H) 3.86 (m, 0.34 H) 3.96 (m, 0.66 H) 7.57 (m, 1 H) 7.72 (d, J=7.9 Hz, 1 H) 7.96 (s, 1 H)

LC-MS-DAD-ELSD: [M+H]+m/z=424

13.1.3: 5-Bromo-7-trifluoromethyl-2-(1-propylbutyl)-3,4-dihydroisoquinoline-1(2H)-one 660 mg of methyl[2-(2-bromo-4-trifluoromethylphenyl)ethyl](1-propylbutyl)carbamate are dissolved under an inert atmosphere in 15 cm³ of dichloromethane at a temperature close to 10° C. 575 mg of 4-dimethylaminopyridine are added to the reaction mixture. 1.32 cm³ of trifluoromethanesulfonic anhydride in solution in 2 cm³ of anhydrous dichloromethane are poured into the reaction mixture over 5 min. The reaction mixture is kept stirring for 15 h at a temperature close to 20° C. 20 cm³ of a saturated aqueous solution of sodium hydrogen carbonate are added to the reaction medium. This stirring is continued for 30 min, then 20 cm³ of dichloromethane are added to the mixture. The organic phase is decanted then washed successively with 100 cm³ of a 0.1M aqueous solution of hydrochloric acid and 20 cm³ of a saturated aqueous solution of sodium hydrogen carbonate. Next, the organic phase is dried then concentrated using a rotary evaporator under reduced pressure (5 kPa). The residual solid is then purified by filtration through silica (silica 60—particle size 15-40 μm—eluent: 50% ethyl ethyl acetate/50% cyclohexane). The organic phase is concentrated under reduced pressure (5 kPa). 519 mg of 5-bromo-7-trifluoromethyl-2-(1-propylbutyl)-3,4-dihydroisoquinoline-1(2H)-one are obtained in the form of a yellow oil.

NMR: 0.87 (t, J=7.1 Hz, 6 H) 1.15-1.34 (m, 4 H) 1.42 (m, 2 H) 1.53 (m, 2 H) 3.05 (t, J=6.6 Hz, 2 H) 3.42 (t, J=6.6 Hz, 2 H) 4.64 (m, 1 H) 8.15 (broad s, 1 H) 8.17 (broad s, 1 H)

LC-MS-DAD-ELSD: [M+H]+m/z=392

13.1.4: 7-Trifluoromethyl-1-oxo-2-(1-propylbutyl)-1,2,3,4-tetrahydroisoquinoline-5-carboxylic acid Introduced successively, at a temperature close to 20° C., into a three-necked flask that is stirred and purged using carbon monoxide are 500 mg of 5-bromo-7-trifluoromethyl-2-(1-propylbutyl)-3,4-dihydroisoquinoline-1(2H)-one, 16 cm³ of dimethylformamide, 0.8 cm³ of water, 482 mg of potassium acetate, 222 mg of potassium iodide, 28 mg of palladium acetate and 68 mg of triphenylphosphine. The reaction mixture is subjected to a carbon monoxide bubbling, then it is heated at a temperature close to 100° C. for 6 h. The reaction mixture is cooled to 25° C., then concentrated using a rotary evaporator under reduced pressure (5 kPa). The residue is taken up in 50 cm³ of ethyl acetate. The pH is alcalinized with 1M sodium hydroxide (pH>10). The two phases are decanted and separated. The aqueous phase is acidified, while stirring, with a 5M solution of hydrochloric acid (pH=2), then extracted with 30 cm³ of ethyl acetate. The organic phase is dried over magnesium sulfate and concentrated using a rotary evaporator under reduced pressure (5 kPa). 336 mg of 7-trifluoromethyl-1-oxo-2-(1-propylbutyl)-1,2,3,4-tetrahydroisoquinoline-5-carboxylic acid are obtained in the form of an amorphous whitish solid.

NMR: 0.87 (t, J=7.3 Hz, 6 H) 1.15-1.31 (m, 4 H) 1.41 (m, 2 H) 1.53 (m, 2 H) 3.36 (broad s, 4 H) 4.66 (m, 1 H) 8.23 (d, J=2.2 Hz, 1 H) 8.32 (d, J=2.2 Hz, 1 H) 13.60 (broad unresolved m, 1 H)

LC-MS-DAD-ELSD: [M+H]+m/z=358; [M−H]−m/z=356

13.1.5: N-[(1S,2R)-1-(3,5-difluorobenzyl)-2-hydroxy-3-({1-[3-(trifluoromethyl)phenyl]cyclopropyl}amino)propyl]-7-trifluoromethyl-1-oxo-2-(1-propylbutyl)-1,2,3,4-tetrahydroisoquinoline-5-carboxamide Added, under an argon atmosphere and at a temperature close to 20° C., to a solution of 150 mg of 7-trifluoromethyl- 1-oxo-2-(1-propylbutyl)-1,2,3,4-tetrahydroisoquinoline-5-carboxylic acid in 20 cm³ of dichloromethane are 0.30 cm³ of N,N-diisopropylethylamine, 5 mg of 4-dimethylaminopyridine and 200 mg of (2R,3S)-3-amino-4-(3,5-difluorophenyl)-1-({1-[3-trifluoromethyl)phenyl]cyclopropyl}amino) butan-2-ol hydrochloride then 8.5 mg of 1-hydroxy-7-azabenzotriazole and 100 mg of 1-(3-dimethylaminopropyl)-3-ethylcarbodiimide hydrochloride. The solution is kept stirring under argon for 3 h at a temperature close to 20° C. The reaction medium is then washed successively with 20 cm³ of distilled water and 20 cm³ of a saturated aqueous solution of sodium chloride. The organic phase is decanted, dried then concentrated under reduced pressure (5 kPa). The residual solid is purified by flash chromatography over silica (column: 30 g; silica of the type: SuperVarioPrep D40-SI60 particle size: 15-40 μm; eluent: 90% cyclohexane/10% ethyl acetate). After concentrating the fractions under reduced pressure, 238 mg of N-[(1S,2R)-1-(3,5-difluorobenzyl)-2-hydroxy-3-({1-[3-(trifluoromethyl)phenyl]cyclopropyl}amino)propyl]-7-trifluoromethyl-1-oxo-2-(1-propylbutyl)-1,2,3,4-tetrahydroisoquinoline-5-carboxamide are obtained in the form of a colorless oil.

13.2: Salt N-[(1S,2R)-1-(3,5-difluorobenzyl)-2-hydroxy-3-({1-[3-(trifluoromethyl)phenyl]cyclopropyl}amino)propyl]-7-trifluoromethyl-1-oxo-2-(1-propylbutyl)-1,2,3,4-tetrahydroisoquinoline-5-carboxamide hydrochloride The oil obtained in step 13.1 is then dissolved in 5 cm³ of ethyl ether. 1 cm³ of a 1N solution of hydrochloric acid in ethyl ether, then 1 cm³ of methanol, are added, while stirring, at a temperature of 20° C. The reaction mixture is concentrated to dryness under reduced pressure (5 kPa). The residue is triturated with 10 cm³ of diisopropyl ether, the solid formed is filtered, then dried under atmospheric pressure at a temperature close to 20° C. 249 mg of N-[(1S,2R)-1-(3,5-difluorobenzyl)-2-hydroxy-3-({1-[3-(trifluoromethyl)phenyl]cyclopropyl}amino)propyl]-7-fluoro-1-oxo-2-(1-propylbutyl)-1,2,3,4-tetrahydroisoquinoline-5-carboxamide hydrochloride are obtained in the form of a white solid.

NMR: 0.86 (t, J=7.3 Hz 3 H) 0.87 (t, J=7.3 Hz, 3 H) 1.11-1.69 (m, 12 H) 2.42-2.71 (partially masked m, 2 H) 2.80 (m, 1 H) 3.03-3.35 (partially masked m, 5 H) 3.84 (m, 1 H) 4.12 (m, 1 H) 4.64 (m, 1 H) 5.89 (broad d, J=6.2 Hz, 1 H) 6.98 (m, 2 H) 7.09 (tt, J=9.5, 2.0 Hz, 1 H) 7.41 (d, J=1.0 Hz, 1 H) 7.66 (broad t, J=7.9 Hz, 1 H) 7.76 (broad d, J=7.9 Hz, 1 H) 7.90 (broad d, J=7.9 Hz, 1 H) 7.99 (broad s, 1 H) 8.17 (d, J=1.0 Hz, 1 H) 8.48 (d, J=8.8 Hz, 1 H) 9.35 (broad m, 1 H) 9.67 (broad m, 1 H)

LC-MS-DAD-ELSD: [M+H]+m/z=740; [M−H]−m/z=738

MP=196° C.

EXAMPLE 14

14.1: Base N-[(1S,2R)-1-(3,5-difluorobenzyl)-2-hydroxy-3-({1-[3-(trifluoromethyl)phenyl]cyclopropyl}amino)propyl]-7-[(methylsulfonyl)amino]-1-oxo-2-(1-propylbutyl)-1,2,3,4-tetrahydroisoquinoline-5-carboxamide 14.1.1: 7-[(Methylsulfonyl)amino]-1-oxo-2-(1-propylbutyl)-1,2,3,4-tetrahydroisoquinoline-5-carboxylic acid 0.51 g of methyl 7-[(methylsulfonyl)amino]-1-oxo-2-(1-propylbutyl)-1,2,3,4-tetrahydroisoquinoline-5-carboxylate is dissolved in 10.5 cm³ of dioxane at a temperature close to 20° C. 3.2 cm³ of a 1N aqueous solution of sodium hydroxide are added, then the reaction mixture is heated at a temperature close to 60° C. for 30 min. The dioxane contained in the reaction mixture is concentrated to dryness under reduced pressure (5 kPa). 20 cm³ of ethyl ether and 20 cm³ of water are added to the residue obtained. After decantation, the aqueous phase is acidified with 2 cm³ of a 2N aqueous solution of hydrochloric acid. 50 cm³ of dichloromethane are added to the mixture, which is stirred for 1 h at a temperature close to 20° C. The precipitate is filtered, washed with two lots of 10 cm³ of water then two lots of 10 cm³ of dichloromethane and dried under vacuum. 0.42 g of 7-[(methylsulfonyl)amino]-1-oxo-2-(1-propylbutyl)-1,2,3,4-tetrahydroisoquinoline-5-carboxylic acid is obtained in the form of a powder.

NMR: 0.87 (t, J=7.5 Hz, 6H); from 1.12 to 1.30 (m, 4H); 1.39 (m, 2H); 1.51 (m, 2H); 3.00 (s, 3H); 3.19 (m, 2H); 3.29 (partially masked m, 2H); 4.63 (m, 1H); 7.87 (d, J=2.0 Hz, 1H); 7.98 (d, J=2.0 Hz, 1H); 9.94 (broad s, 1H); 13.3 (broad unresolved m, 1H)

LC-MS-DAD-ELSD: [M+H]+: m/z 383; [M−H]−: m/z 381; [2M−H]−: m/z 763 (base peak)

14.1.2: N-[(1S,2R)-1-(3,5-difluorobenzyl)-2-hydroxy-3-({1-[3-(trifluoromethyl)phenyl]cyclopropyl}amino)propyl]-7-[(methylsulfonyl)amino]-1-oxo-2-(1-propyl butyl)-1,2,3,4-tetrahydroisoquinoline-5-carboxamide Added to a solution of 185 mg of (2R,3S)-3-amino-4-(3,5-difluorophenyl)-1-({1-[3-(trifluoromethyl)phenyl]cyclopropyl}amino)butan-2-ol hydrochloride (2:1), 150 mg of 7-[(methylsulfonyl)amino]-1-oxo-2-(1-propylbutyl)-1,2,3,4-tetrahydroisoquinoline-5-carboxylic acid and 0.176 cm³ of triethylamine in 1.6 cm³ of anhydrous dimethylformamide are 64 mg of 1-hydroxy-7-azabenzotriazole then 90 mg of 1-(3-dimethylaminopropyl)-3-ethylcarbodiimide hydrochloride. The solution is kept stirring for 24 h at a temperature close to 20° C. 20 cm³ of water and 50 cm³ of ethyl acetate are added to the reaction medium. After decantation, the organic phase is washed with 20 cm³ of a saturated aqueous solution of ammonium chloride, five lots of 20 cm³ of water, 20 cm³ of saturated aqueous solution of sodium chloride, then dried over anhydrous magnesium sulfate, filtered and concentrated to dryness under reduced pressure (5 kPa). The residual solution (around 3 cm³) is filtered through a pellet of 15 g of 40-63 μm silica. The silica pellet is washed with 75 cm³ of ethyl acetate. The filtrate is concentrated to dryness under reduced pressure (5 kPa). 300 mg of N-[(1S,2R)-1-(3,5-difluorobenzyl)-2-hydroxy-3-({1-[3-trifluoromethyl)phenyl]cyclopropyl}amino)propyl]-7-[(methylsulfonyl)amino]-1-oxo-2-(1-propylbutyl)-1,2,3,4-tetrahydroisoquinoline-5-carboxamide are obtained in the form of a directly salified white powder.

14.2: Salt N-[(1S,2R)-1-(3,5-difluorobenzyl)-2-hydroxy-3-({1-[3-(trifluoromethyl)phenyl]cyclopropyl}amino)propyl]-7-[(methylsulfonyl)amino]-1-oxo-2-(1-propylbutyl)-1,2,3,4-tetrahydroisoquinoline-5-carboxamide hydrochloride (1:1)

300 mg of N-[(1S,2R)-1-(3,5-difluorobenzyl)-2-hydroxy-3-({1-[3-(trifluoromethyl)phenyl]cyclopropyl}amino)propyl]-7-[(methylsulfonyl)amino]-1-oxo-2-(1-propylbutyl)-1,2,3,4-tetrahydroisoquinoline-5-carboxamide are dissolved in 10 cm³ of ethyl ether at a temperature close to 20° C. 0.4 cm³ of a 4N solution of hydrochloric acid in dioxane is added while stirring at a temperature of 20° C. The reaction mixture precipitates. The solid is washed with three lots of 5 cm³ of isopropyl ether and dried under vacuum at a temperature of 50° C. 280 mg of N-[(1S,2R)-1-(3,5-difluorobenzyl)-2-hydroxy-3-({1-[3-(trifluoromethyl)phenyl]cyclopropyl}amino)propyl]-7-[(methylsulfonyl)amino]-1-oxo-2-(1-propylbutyl)-1,2,3,4-tetrahydroisoquinoline-5-carboxamide hydrochloride (1:1) are obtained in the form of a white powder.

NMR: 0.88 (m, 6H); from 1.11 to 1.69 (m, 12H); 2.37 (m, 2H); 2.63 (m, 1H); 2.74 (m, 1H); 3.00 (s, 3H); from 3.01 to 3.15 (m, 4H); 3.88 (m, 1H); 4.11 (m, 1H); 4.63 (m, 1H); 5.86 (broad m, 1H); 6.93 (m, 2H); 7.18 (tt, J=2.0 and 9.0 Hz, 1H); 7.20 (d, J=2.5 Hz, 1H); 7.68 (broad t, J=7.5 Hz, 1H); 7.78 (m, 2H); 7.90 (broad d, J=7.5 Hz, 1H); 8.01 (broad s, 1H); 8.39 (broad d, J=8.0 Hz, 1H); 9.47 (broad m, 1H); 9.87 (broad m, 1H); 9.97 (s, 1H)

LC-MS-DAD-ELSD: [M+H]⁺: m/z 765; [M−H]⁻: m/z 763

EXAMPLE 15

N-[(1S,2R)-1-(3,5-difluorobenzyl)-2-hydroxy-3-({1-[3-(trifluoromethyl)phenyl]cyclopropyl}amino)propyl]-7-(2-oxazolyl)-1-oxo-2-(1-propylbutyl)-1,2,3,4-tetrahydroisoquinoline-5-carboxamide hydrochloride (1:1)

15.1: Methyl 7-bromo-1-oxo-2-(1-propyl butyl)-1,2,3,4-tetrahydroisoquinoline-5-carboxylate Added to a solution of 0.87 cm³ of N-butyl nitrite in 65 cm³ of acetonitrile, at a temperature close to 0° C., are 1.26 g of cupric bromide, then, over 25 minutes, a solution of 1.5 g of methyl 7-amino-1-oxo-2-(1-propylbutyl)-1,2,3,4-tetrahydroisoquinoline-5-carboxylate dissolved in 70 cm³ of acetonitrile is introduced. The stirring is continued for 4 h at a temperature close to 20° C. 30 cm³ of water is added to the reaction medium and the precipitate is filtered. It is washed with two lots of 20 cm³ of acetonitrile. The filtrate is concentrated to dryness under reduced pressure (5 kPa) then taken up by 250 cm³ of ethyl acetate and 50 cm³ of water. The organic phase is decanted, washed with two lots of 20 cm³ of a 2N aqueous solution of hydrochloric acid, then 50 cm³ of water and 50 cm³ of a saturated aqueous solution of sodium chloride, dried over magnesium sulfate, filtered and concentrated to dryness under reduced pressure (5 kPa). The residual oil is dissolved in 5 cm³ of dichloromethane, then purified by flash chromatography over silica (column: 200 g; particle size: 15-40 μm; eluent: 60% heptane/40% ethyl acetate). After concentrating the fractions under reduced pressure, 1.2 g of methyl 7-bromo-1-oxo-2-(1-propylbutyl)-1,2,3,4-tetrahydroisoquinoline-5-carboxylate are obtained in the form of a yellow oil.

NMR: 0.89 (m, 6H); from 1.10 to 1.70 (m, 8H); from 2.38 to 2.60 (partially masked m, 2H); 2.65 (m, 1H); 2.81 (m, 1H): from 3.03 to 3.24 (m, 4H); from 3.30 to 3.60 (masked m, 2H); 3.89 (m, 1H); 4.16 (m, 1H); 4.68 (m, 1H); 5.92 (broad unresolved m, 1H); 6.99 (m, 2H); 7.10 (broad t, J=9.0 Hz, 1H); 7.46 (s, 1H); 7.68 (t, J=7.5 Hz, 1H); 7.74 (m, 2H); 7.92 (d, J=7.5 Hz, 1H); 8.01 (broad s, 1H); 8.29 (s, 1H); 8.49 (m, 2H); 9.42 (broad m, 1H); 9.80 (broad m, 1H)

LC-MS-DAD-ELSD: [M+H]⁺: m/z 382 (base peak); [2M+Na]⁺: m/z 785

15.2: Methyl 7-(2-oxazolyl)-1-oxo-2-(1-propyl butyl)-1,2,3,4-tetrahydroisoquinoline-5-carboxylate Added to a solution of 0.8 g of methyl 7-bromo-1-oxo-2-(1-propylbutyl)-1,2,3,4-tetrahydroisoquinoline-5-carboxylate in 8 cm³ of dioxane, under an argon atmosphere at a temperature close to 20° C. are 308 mg of tetrakis(triphenylphosphine)palladium and 3.2 g of 2-(tri-n-butylstannyl)oxazole. The reaction medium is heated at 145° C. in a microwave oven for 15 minutes, then left to return to a temperature close to 20° C. The reaction medium is concentrated to dryness under reduced pressure (5 kPa). The residue is taken up by 5 cm³ of dichloromethane and purified by flash chromatography over silica (column: 110 g; spherical silica of BP-SUP type particle size: 20-40 μm; eluent: 90% heptane/10% ethyl acetate then 100% ethyl acetate). After concentrating the fractions under reduced pressure, 320 mg of methyl 7-(2-oxazolyl)-1-oxo-2-(1-propylbutyl)-1,2,3,4-tetrahydroisoquinoline-5-carboxylate are obtained.

NMR: 0.89 (t, J=7.5 Hz, 6H); from 1.14 to 1.34 (m, 4H); 1.41 (m, 2H); 1.56 (m, 2H); from 3.25 to 3.40 (partially masked m, 4H); 3.91 (s, 3H); 4.68 (m, 1H); 7.43 (s, 1H); 8.29 (s, 1H); 8.53 (d, J=2.0 Hz, 1H); 8.68 (d, J=2.0 Hz, 1H)

LC-MS-DAD-ELSD: [M+H]⁺: m/z 371 (base peak); [2M+H]⁺: m/z 741; [2M+Na]⁺: m/z 763

The preparation of 2-(tri-n-butylstannyl)oxazole is described in international patent application WO 2006/099352.

15.3: 7-(2-Oxazolyl)-1-oxo-2-(1-propylbutyl)-1,2,3,4-tetrahydroisoquinoline-5-carboxylic acid 320 mg of methyl 7-(2-oxazolyl)-1-oxo-2-(1-propylbutyl)-1,2,3,4-tetrahydroisoquinoline-5-carboxylate are dissolved in 7 cm³ of dioxane at a temperature close to 20° C. 2.1 cm³ of a 1N aqueous solution of sodium hydroxide are added, then the reaction mixture is heated at a temperature close to 60° C. for 30 min. The dioxane contained in the reaction mixture is concentrated to dryness under reduced pressure (5 kPa). 2.5 cm³ of a 1N aqueous solution of hydrochloric acid, 20 cm³ of dichloromethane and 20 cm³ of water are added to the residue obtained. After decanting, the organic phase is dried over anhydrous magnesium sulfate, filtered and concentrated to dryness under reduced pressure (5 kPa). 289 mg of 7-(2-oxazolyl)-1-oxo-2-(1-propylbutyl)-1,2,3,4-tetrahydroisoquinoline-5-carboxylic acid are obtained in the form of a beige powder.

NMR: 0.89 (t, J=7.5 Hz, 6H); from 1.11 to 1.32 (m, 4H); 1.41 (m, 2H); 1.54 (m, 2H); from 3.22 to 3.39 (partially masked m, 4H); 4.69 (m, 1H); 7.43 (s, 1H); 8.28 (s, 1H); 8.52 (d, J=2.0 Hz, 1H); 8.62 (d, J=2.0 Hz, 1H); 13.45 (broad unresolved m, 1H)

LC-MS-DAD-ELSD: [M+H]⁺: m/z 357 (base peak); [2M+H]⁺: m/z 713; [M−H]⁻: m/z 355 (base peak); [2M−H]⁻: m/z 711

15.4: N-[(1S,2R)-1-(3,5-difluorobenzyl)-2-hydroxy-3-({1-[3-(trifluoromethyl)phenyl]cyclopropyl}amino)propyl]-7-(2-oxazolyl)-1-oxo-2-(1-propylbutyl)-1,2,3,4-tetrahydroisoquinoline-5-carboxamide hydrochloride (1:1)

Added to a solution of 150 mg of 7-(2-oxazolyl)-1-oxo-2-(1-propylbutyl)-1,2,3,4-tetrahydroisoquinoline-5-carboxylic acid in 4 cm³ of anhydrous dimethylformamide and under an argon atmosphere are 0.19 cm³ of triethylamine and 201 mg of (2R,3S)-3-amino-4-(3,5-difluorophenyl)-1-({1-[3-(trifluoromethyl)phenyl]cyclopropyl}amino)butan-2-ol hydrochloride then 69 mg of 1-hydroxy-7-azabenzotriazole and 97 mg of 1-(3-dimethylaminopropyl)-3-ethylcarbodiimide hydrochloride. The solution is kept stirring for 15 h at a temperature close to 20° C. 50 cm³ of water and 50 cm³ of ethyl acetate are added to the reaction medium. After decanting, the organic phase is washed with 50 cm³ of a saturated aqueous solution of ammonium chloride, two lots of 20 cm³ of water and 20 cm³ of a saturated aqueous solution of sodium chloride, dried over anhydrous magnesium sulfate, filtered and concentrated to dryness under reduced pressure (5 kPa). The residual solution (around 3 cm³) is filtered through a pellet of 15 g of 40-63 μm silica. The silica pellet is washed with 40 cm³ of ethyl acetate. The filtrate is concentrated to dryness under reduced pressure (5 kPa). 255 mg is obtained of a white powder which is dissolved in 10 cm³ of ethyl ether. Added thereto, while stirring, is 0.2 cm³ of a 4N solution of hydrochloric acid in dioxane at a temperature of 20° C. The reaction mixture precipitates. The precipitate is filtered, washed with two lots of 5 cm³ of isopropyl ether and dried under vacuum at a temperature of 35° C. 236 mg of N-[(1S,2R)-1-(3,5-difluorobenzyl)-2-hydroxy-3-({1-[3-(trifluoromethyl)phenyl]cyclopropyl}amino)propyl]-7-(2-oxazolyl)-1-oxo-2-(1-propylbutyl)-1,2,3,4-tetrahydroisoquinoline-5-carboxamide hydrochloride are obtained in the form of white crystals.

NMR: 0.89 (m, 6H); from 1.10 to 1.70 (m, 8H); from 2.38 to 2.60 (partially masked m, 2H); 2.65 (m, 1H); 2.81 (m, 1H); from 3.03 to 3.24 (m, 4H); from 3.30 to 3.60 (masked m, 2H); 3.89 (m, 1H); 4.16 (m, 1H); 4.68 (m, 1H); 5.92 (broad unresolved m, 1H); 6.99 (m, 2H); 7.10 (broad t, J=9.0 Hz, 1H); 7.46 (s, 1H); 7.68 (t, J=7.5 Hz, 1H); 7.74 (m, 2H); 7.92 (d, J=7.5 Hz, 1H); 8.01 (broad s, 1H); 8.29 (s, 1H); 8.49 (m, 2H); 9.42 (broad m, 1H); 9.80 (broad m, 1H)

LC-MS-DAD-ELSD: [M+H]⁺: m/z 739; [M−H]⁻: m/z 737

EXAMPLE 16

16.1: Base N-[(1S,2R)-1-(3,5-difluorobenzyl)-2-hydroxy-3-({1-[3-(trifluoromethyl)phenyl]cyclopropyl}amino)propyl]-7-(3-cyanophenyl)-1-oxo-2-(1-propylbutyl)-1,2,3,4-tetrahydroisoquinoline-5-carboxamide 16.1.1: Methyl 7-(3-cyanophenyl)-1-oxo-2-(1-propyl butyl)-1,2,3,4-tetrahydroisoquinoline-5-carboxylate Added to a solution of 0.3 g of methyl 7-bromo-1-oxo-2-(1-propylbutyl)-1,2,3,4-tetrahydroisoquinoline-5-carboxylate in 9.4 cm³ of dioxane and 1.8 cm³ of water, at a temperature close to 20° C., are 147 mg of sodium bicarbonate. The reaction medium is then degassed under an argon atmosphere, then 111 mg of 3-cyanophenylboronic acid and 72 mg of tetrakis(triphenylphosphine)palladium are added. The mixture is heated at 150° C. in a microwave oven for 4 minutes, cooled to a temperature close to 20° C. and filtered. The filtrate is dried over anhydrous magnesium sulfate then filtered; added to the filtrate is 1 g of silica and the absorbed residue is purified by flash chromatography over silica (column: 15 g; spherical silica of BP-SUP type, particle size: 20-40 μm, eluent: 80% heptane/20% ethyl acetate then 60% heptane/40% ethyl acetate). After concentrating the fractions under reduced pressure, 103 mg of methyl 7-(3-cyanophenyl)-1-oxo-2-(1-propylbutyl)-1,2,3,4-tetrahydroisoquinoline-5-carboxylate are obtained in the form of an orange oil.

NMR: 0.89 (t, J=7.5 Hz, 6H); from 1.12 to 1.32 (m, 4H); 1.41 (m, 2H); 1.54 (m, 2H); 3.27 (t, J=6.0 Hz, 2H); 3.37 (t, J=6.0 Hz, 2H); 3.90 (s, 3H); 4.70 (m, 1H); 7.70 (t, J=7.5 Hz, 1H); 7.89 (broad d, J=7.5 Hz, 1H); 8.09 (broad d, J=7.5 Hz, 1H); 8.24 (broad s, 1H); 8.29 (d, J=2.0 Hz, 1H); 8.41 (d, J=2.0 Hz, 1H)

LC-MS-DAD-ELSD: [M+H]⁺: m/z 405 (base peak); [2M+H]⁺: m/z 809

16.1.2: 7-(3-Cyanophenyl)-1-oxo-2-(1-propylbutyl)-1,2,3,4-tetrahydroisoquinoline-5-carboxylic acid 103 mg of methyl 7-(3-Cyanophenyl)-1-oxo-2-(1-propylbutyl)-1,2,3,4-tetrahydroisoquinoline-5-carboxylate are dissolved in 2 cm³ of dioxane at a temperature close to 20° C. 0.6 cm³ of a 1N aqueous solution of sodium hydroxide are added, then the reaction mixture is heated at a temperature close to 60° C. for 30 min. The mixture is then concentrated to dryness under reduced pressure (5 kPa), taken up by 20 cm³ of water and 20 cm³ of ethyl ether. The aqueous phase is decanted, acidified with 0.4 cm³ of a 2N aqueous solution of hydrochloric acid and taken up with 20 cm³ of dichloromethane. The organic phase is extracted, dried over anhydrous magnesium sulfate, filtered and concentrated to dryness under reduced pressure (5 kPa). 89 mg of 7-(3-Cyanophenyl)-1-oxo-2-(1-propylbutyl)-1,2,3,4-tetrahydroisoquinoline-5-carboxylic acid are obtained in the form of a white powder.

NMR: 0.89 (t, J=7.5 Hz, 6H); from 1.12 to 1.32 (m, 4H); 1.41 (m, 2H); 1.54 (m, 2H); from 3.21 to 3.40 (partially masked m, 4H); 4.70 (m, 1H); 7.70 (t, J=7.5 Hz, 1H); 7.88 (broad d, J=7.5 Hz, 1H); 8.08 (broad d, J=7.5 Hz, 1H); 8.22 (broad s, 1H); 8.27 (d, J=2.0 Hz, 1H); 8.38 (d, J=2.0 Hz, 1H); 13.4 (broad unresolved m, 1H)

LC-MS-DAD-ELSD: [M+H]⁺: m/z 391 (base peak); [2M+H]⁺: m/z 781; [M−H]⁻: m/z 389 (base peak); [2M−H]⁻: m/z 779

16.1.3: N-[(1S,2R)-1-(3,5-difluorobenzyl)-2-hydroxy-3-({1-[3-(trifluoromethyl)phenyl]cyclopropyl}amino)propyl]-7-(3-cyanophenyl)-1-oxo-2-(1-propylbutyl)-1,2,3,4-tetrahydroisoquinoline-5-carboxamide Added to a solution of 89 mg of 7-(3-cyanophenyl)-1-oxo-2-(1-propylbutyl)-1,2,3,4-tetrahydroisoquinoline-5-carboxylic acid in 1 cm³ of anhydrous dimethylformamide and under an argon atmosphere are 0.092 cm³ of triethylamine and 97 mg of (2R,3S)-3-amino-4-(3,5-difluorophenyl)-1-({1-[3-(trifluoromethyl)phenyl]cyclopropylamino)butan-2-ol hydrochloride (2:1), then 33 mg of 1-hydroxy-7-azabenzotriazole and 47 mg of 1-(3-dimethylaminopropyl)-3-ethylcarbodiimide hydrochloride. The solution is kept stirring for 15 h at a temperature close to 20° C. 50 cm³ of water and 50 cm³ of ethyl acetate are added to the reaction medium. After decanting, the organic phase is washed with three lots of 5 cm³ of water then with 5 cm³ of a saturated aqueous solution of ammonium chloride, then 20 cm³ of a saturated aqueous solution of sodium chloride, dried over anhydrous magnesium sulfate, filtered and concentrated to dryness under reduced pressure (5 kPa). The residue is diluted in 2 cm³ of dichloromethane and purified by flash chromatography over silica (column: 15 g; particle size: 15-40 μm; eluent: 20% heptane/80% ethyl acetate). After concentrating the fractions under reduced pressure, 119 mg of N-[(1S,2R)-1-(3,5-difluorobenzyl)-2-hydroxy-3-({1-[3-(trifluoromethyl)phenyl]cyclopropyl}amino)propyl]-7-(3-cyanophenyl)-1-oxo-2-(1-propylbutyl)-1,2,3,4-tetrahydroisoquinoline-5-carboxamide are obtained in the form of a white gum.

LC-MS-DAD-ELSD: [M+H]⁺: m/z 773; [M−H]⁻: m/z 771 (base peak); [M+HCO₂H−H]⁻: m/z 817

16.2: Salt N-[(1S,2R)-1-(3,5-difluorobenzyl)-2-hydroxy-3-({1-[3-(trifluoromethyl)phenyl]cyclopropyl}amino)propyl]-7-(3-cyanophenyl)-1-oxo-2-(1-propylbutyl)-1,2,3,4-tetrahydroisoquinoline-5-carboxamide hydrochloride (1:1)

119 mg of N-[(1S,2R)-1-(3,5-difluorobenzyl)-2-hydroxy-3-({1-[3-(trifluoromethyl)phenyl]cyclopropyl}amino)propyl]-7-(3-cyanophenyl)-1-oxo-2-(1-propylbutyl)-1,2,3,4-tetrahydroisoquinoline-5-carboxamide are dissolved in 5 cm$^3$ of ethyl ether. 0.3 cm$^3$ of a 2N solution of hydrochloric acid in ethyl ether is added while stirring at a temperature of 20° C. The precipitate formed is filtered and dried under vacuum at a temperature of 35° C. 89 mg of N-[(1S,2R)-1-(3,5-difluorobenzyl)-2-hydroxy-3-({1-[3-(trifluoromethyl)phenyl]cyclopropyl}amino)propyl]-7-(3-cyanophenyl)-1-oxo-2-(1-propylbutyl)-1,2,3,4-tetrahydroisoquinoline-5-carboxamide hydrochloride (1:1) are obtained in the form of a white powder.

NMR: 0.89 (m, 6H); from 1.11 to 1.69 (m, 12H); from 2.42 to 2.60 (partially masked m, 2H); 2.69 (m, 1H); 2.80 (m, 1H); from 3.03 to 3.24 (m, 4H); 3.85 (m, 1H); 4.13 (m, 1H); 4.69 (m, 1H); 5.89 (broad m, 1H); from 6.95 to 7.11 (m, 3H); 7.49 (broad s, 1H); from 7.55 to 7.79 (m, 3H); 7.90 (m, 2H); 8.00 (m, 2H); 8.13 (broad s, 1H); 8.22 (broad s, 1H); 8.43 (broad d, J=8.0 Hz, 1H); 9.36 (broad m, 1H); 9.72 (broad m, 1H)

LC-MS-DAD-ELSD: [M+H]$^+$: m/z 773; [M−H]$^-$: m/z 771 (base peak); [M+HCO$_2$H−H]$^-$: m/z 817

EXAMPLE 17

17.1: Base N-[(1S,2R)-1-(3,5-difluorobenzyl)-2-hydroxy-3-({1-[3-(trifluoromethyl)phenyl]cyclopropyl}amino)propyl]-7-(2-cyanophenyl)-1-oxo-2-(1-propylbutyl)-1,2,3,4-tetrahydroisoquinoline-5-carboxamide

17.1.1: Methyl 7-(2-cyanophenyl)-1-oxo-2-(1-propylbutyl)-1,2,3,4-tetrahydroisoquinoline-5-carboxylate Added to a solution of 0.4 g of methyl 7-bromo-1-oxo-2-(1-propylbutyl)-1,2,3,4-tetrahydroisoquinoline-5-carboxylate in 12.5 cm$^3$ of dioxane and 2.5 cm$^3$ of water, at a temperature close to 20° C., are 196 mg of sodium bicarbonate. The reaction medium is then degassed under an argon atmosphere, then 147.5 mg of 2-cyanophenylboronic acid and 96 mg of tetrakis(triphenylphosphine)palladium are added. The mixture is heated at 150° C. in a microwave oven for 4 minutes, cooled to a temperature close to 20° C. and filtered. The filtrate is taken up by 20 cm$^3$ of dichloromethane and 20 cm$^3$ of water. The organic phase is extracted, dried over anhydrous magnesium sulfate, filtered and concentrated under reduced pressure (5 kPa). The residual solution (around 3 cm$^3$) is purified by flash chromatography over silica (column: 50 g; spherical silica of BP-SUP type, partical size: 20-40 μm; eluent: 80% heptane/20% ethyl acetate then 60% heptane/40% ethyl acetate then 50% heptane/50% ethyl acetate). After concentrating the fractions under reduced pressure, 178 mg of methyl 7-(2-cyanophenyl)-1-oxo-2-(1-propylbutyl)-1,2,3,4-tetrahydroisoquinoline-5-carboxylate are obtained in the form of a colorless oil.

NMR: 0.89 (t, J=7.5 Hz, 6H); from 1.16 to 1.32 (m, 4H); 1.42 (m, 2H); 1.53 (m, 2H); from 3.25 to 3.35 (masked m, 2H); 3.39 (m, 2H); 3.89 (s, 3H); 4.68 (m, 1H); 7.63 (dt, J=1.5 and 7.5 Hz, 1H); 7.70 (broad d, J=7.5 Hz, 1H); 7.83 (dt, J=1.5 and 7.5 Hz, 1H); 8.00 (dd, J=1.5 and 7.5 Hz, 1H); 8.27 (d, J=2.0 Hz, 1H); 8.30 (d, J=2.0 Hz, 1H)

LC-MS-DAD-ELSD: [M+H]$^+$: m/z 405 (base peak); [M+Na]$^+$: m/z 427; [M+HCO$_2$H−H]$^-$: m/z 449

17.1.2: 7-(2-Cyanophenyl)-1-oxo-2-(1-propylbutyl)-1,2,3,4-tetrahydroisoquinoline-5-carboxylic acid 178 mg of methyl 7-(2-cyanophenyl)-1-oxo-2-(1-propylbutyl)-1,2,3,4-tetrahydroisoquinoline-5-carboxylate are dissolved in 3.6 cm$^3$ of dioxane at a temperature close to 20° C. 1.1 cm$^3$ of a 1N aqueous solution of sodium hydroxide are added, then the reaction mixture is heated at a temperature close to 60° C. for 30 min. The mixture is then concentrated to dryness under reduced pressure (5 kPa), taken up by 20 cm$^3$ of water and 20 cm$^3$ of ethyl ether. The aqueous phase is washed with 5 cm$^3$ of ethyl ether, acidified with 2 cm$^3$ of a 2N aqueous solution of hydrochloric acid and taken up with 10 cm$^3$ of dichloromethane. The organic phase is extracted, dried over anhydrous magnesium sulfate, filtered and concentrated to dryness under reduced pressure (5 kPa). 171 mg of 7-(2-cyanophenyl)-1-oxo-2-(1-propylbutyl)-1,2,3,4-tetrahydroisoquinoline-5-carboxylic acid are obtained in the form of a white foam.

NMR: 0.89 (t, J=7.5 Hz, 6H); from 1.16 to 1.32 (m, 4H); 1.41 (m, 2H); 1.54 (m, 2H); from 3.25 to 3.41 (partially masked m, 4H); 4.69 (m, 1H); 7.63 (dt, J=1.5 and 7.5 Hz, 1H); 7.70 (broad d, J=7.5 Hz, 1H); 7.82 (dt, J=1.5 and 7.5 Hz, 1H); 7.99 (broad d, J=7.5 Hz, 1H); 8.16 (d, J=2.0 Hz, 1H); 8.25 (d, J=2.0 Hz, 1H); 13.4 (broad unresolved m, 1H)

LC-MS-DAD-ELSD: [M+H]$^+$: m/z 391; [M+Na]$^+$: m/z 413 (base peak)

17.1.3: N-[(1S,2R)-1-(3,5-difluorobenzyl)-2-hydroxy-3-({1-[3-(trifluoromethyl)phenyl]cyclopropyl}amino)propyl]-7-(2-cyanophenyl)-1-oxo-2-(1-propylbutyl)-1,2,3,4-tetrahydroisoquinoline-5-carboxamide Added to a solution of 171 mg of 7-(2-cyanophenyl)-1-oxo-2-(1-propylbutyl)-1,2,3,4-tetrahydroisoquinoline-5-carboxylic acid in 2 cm$^3$ of anhydrous dimethylformamide and under an argon atmosphere are 0.198 cm$^3$ of triethylamine and 207 mg of (2R,3S)-3-amino-4-(3,5-difluorophenyl)-1-({1-[3-(trifluoromethyl)phenyl]cyclopropyl}amino)butan-2-ol hydrochloride, then 71 mg of 1-hydroxy-7-azabenzotriazole and 100.5 mg of 1-(3-dimethylaminopropyl)-3-ethylcarbodiimide hydrochloride. The solution is kept stirring for 15 h at a temperature close to 20° C. 50 cm$^3$ of water and 50 cm$^3$ of ethyl acetate are added to the reaction medium. After decanting, the organic phase is washed with 50 cm$^3$ of a saturated aqueous solution of ammonium chloride, two lots of 20 cm$^3$ of water, then 20 cm$^3$ of a saturated aqueous solution of sodium chloride, dried over anhydrous magnesium sulfate, filtered and concentrated to dryness under reduced pressure (5 kPa). The residual solution (around 3 cm$^3$) is purified by flash chromatography over silica (column: 15 g; spherical silica of BP-SUP type, particle size: 20-40 μm; eluent: 50% heptane/50% ethyl acetate). After concentrating the fractions under reduced pressure, 268 mg of N-[(1S,2R)-1-(3,5-difluorobenzyl)-2-hydroxy-3-({1-[3-(trifluoromethyl)phenyl]cyclopropyl}amino)propyl]-7-(2-cyanophenyl)-1-oxo-2-(1-propylbutyl)-1,2,3,4-tetrahydroisoquinoline-5-carboxamide are obtained in the form of a white powder.

LC-MS-DAD-ELSD: [M+H]⁺: m/z 773; (base peak); [2M+H]⁺: m/z 1545

17.2: Salt N-[(1S,2R)-1-(3,5-difluorobenzyl)-2-hydroxy-3-({1-[3-(trifluoromethyl)phenyl]cyclopropyl}amino)propyl]-7-(2-cyanophenyl)-1-oxo-2-(1-propylbutyl)-1,2,3,4-tetrahydroisoquinoline-5-carboxamide hydrochloride (1:1)

268 mg of N-[(1S,2R)-1-(3,5-difluorobenzyl)-2-hydroxy-3-({1-[3-(trifluoromethyl)phenyl]cyclopropyl}amino)propyl]-7-(2-cyanophenyl)-1-oxo-2-(1-propylbutyl)-1,2,3,4-tetrahydroisoquinoline-5-carboxamide are dissolved, under an argon atmosphere, in 5 cm³ of ethyl ether. 0.3 cm³ of a 4N solution of hydrochloric acid in dioxane is added, while stirring, at a temperature of 20° C. The reaction mixture precipitates. The supernatant is drawn off under vacuum, the residue is washed with 5 cm³ of isopropyl ether; this operation is reproduced three times then the residual medium is dried under vacuum at a temperature of 50° C. 230 mg of N-[(1S,2R)-1-(3,5-difluorobenzyl)-2-hydroxy-3-({1-[3-(trifluoromethyl)phenyl]cyclopropyl}amino)propyl]-7-(2-cyanophenyl)-1-oxo-2-(1-propylbutyl)-1,2,3,4-tetrahydroisoquinoline-5-carboxamide hydrochloride (1:1) are obtained in the form of a white powder.

NMR: 0.89 (m, 6H); from 1.11 to 1.69 (m, 12H); from 2.41 to 2.59 (partially masked m, 2H); 2.65 (m, 1H); 2.79 (m, 1H); from 3.00 to 3.25 (m, 4H); 3.82 (m, 1H); 4.14 (m, 1H); 4.68 (m, 1H); 5.87 (broad m, 1H); 6.97 (m, 2H); 7.08 (broad t, J=9.0 Hz, 1H); 7.30 (broad s, 1H); from 7.51 to 7.71 (m, 4H); 7.84 (m, 2H); 8.00 (m, 2H); 8.12 (broad s, 1H); 8.41 (broad d, J=8.0 Hz, 1H); 9.37 (broad m, 1H); 9.72 (broad m, 1H)

LC-MS-DAD-ELSD: [M+H]⁺: m/z 773; [M−H]⁻: m/z 771 (base peak); [M+HCO₂H—H]⁻: m/z 817

EXAMPLE 18

18.1: Base N-[(1S,2R)-1-(3,5-difluorobenzyl)-2-hydroxy-3-({1-[3-(trifluoromethyl)phenyl]cyclopropyl}amino)propyl]-7-methyl-1-oxo-2-(1-propylbutyl)-1,2,3,4-tetrahydroisoquinoline-5-carboxamide

18.1.1: Methyl 7-methyl-1-oxo-2-(1-propylbutyl)-1,2,3,4-tetrahydroisoquinoline-5-carboxylate Added to a solution of 0.385 g of methyl 7-bromo-1-oxo-2-(1-propylbutyl)-1,2,3,4-tetrahydroisoquinoline-5-carboxylate in 9.6 cm³ of dioxane, 2 cm³ of water and one drop of dimethylformamide, at a temperature close to 20° C., are 190 mg of sodium bicarbonate. The reaction medium is then degassed under an argon atmosphere, then 58 mg of methylboronic acid and 93 mg of tetrakis(triphenylphosphine)palladium are added. The mixture is heated at 150° C. in a microwave oven for 8 minutes, cooled to a temperature close to 20° C., filtered and concentrated to dryness under reduced pressure (5 kPa). The filtrate is taken up by 20 cm³ of dichloromethane and 10 cm³ of water. The organic phase is extracted, washed with a saturated aqueous solution of sodium chloride, dried over anhydrous magnesium sulfate, filtered and concentrated under reduced pressure (5 kPa). The residual solution (around 4 cm³) is purified by flash chromatography over silica (column: 50 g; spherical silica of BP-SUP type, particle size: 20-40 µm; eluent: 80% heptane/20% ethyl acetate then 60% heptane/40% ethyl acetate then 100% ethyl acetate). After concentrating the fractions under reduced pressure, 35 mg of methyl 7-methyl-1-oxo-2-(1-propylbutyl)-1,2,3,4-tetrahydroisoquinoline-5-carboxylate are obtained in the form of a colorless oil.

NMR: 0.86 (t, J=7.5 Hz, 6H); from 1.12 to 1.30 (m, 4H); 1.39 (m, 2H); 1.51 (m, 2H); 2.38 (s, 3H); 3.16 (t, J=6.0 Hz, 2H); from 3.22 to 3.34 (partially masked m, 2H); 3.83 (s, 3H); 4.67 (m, 1H); 7.81 (broad s, 1H); 7.95 (broad s, 1H)

LC-MS-DAD-ELSD: [M+H]⁺: m/z 318 (base peak); [M+Na+CH₃CN]⁺: m/z 381; [2M+Na]⁺: m/z 657

18.1.2: 7-methyl-1-oxo-2-(1-propyl butyl)-1,2,3,4-tetrahydroisoquinoline-5-carboxylic acid 33 mg of methyl 7-methyl-1-oxo-2-(1-propylbutyl)-1,2,3,4-tetrahydroisoquinoline-5-carboxylate are dissolved in 1 cm³ of dioxane at a temperature close to 20° C. 0.3 cm³ of a 1N aqueous solution of sodium hydroxide is added, then the reaction mixture is heated at a temperature close to 60° C. for 1 h. The mixture is then concentrated to dryness under reduced pressure (5 kPa), taken up by 10 cm³ of water and 15 cm³ of ethyl ether. The aqueous phase is decanted, washed with 10 cm³ of ethyl ether, acidified with 0.3 cm³ of a 2N aqueous solution of hydrochloric acid and taken up with 10 cm³ of dichloromethane. The organic phase is extracted, dried over anhydrous magnesium sulfate, filtered and concentrated to dryness under reduced pressure (5 kPa). 33.5 mg of 7-methyl-1-oxo-2-(1-propylbutyl)-1,2,3,4-tetrahydroisoquinoline-5-carboxylic acid are obtained in the form of a colorless lacquer.

NMR: 0.87 (t, J=7.5 Hz, 6H); from 1.12 to 1.30 (m, 4H); 1.39 (m, 2H); 1.50 (m, 2H); 2.37 (s, 3H); 3.19 (m, 2H); 3.27 (partially masked m, 2H); 4.67 (m, 1H); 7.78 (broad s, 1H); 7.89 (broad s, 1H); 13.1 (broad unresolved m, 1H)

LC-MS-DAD-ELSD: [M+H]⁺: m/z 304; [M−H]⁻: m/z 302

18.1.3: N-[(1S,2R)-1-(3,5-difluorobenzyl)-2-hydroxy-3-({1-[3-(trifluoromethyl)phenyl]cyclopropyl}amino)propyl]-7-methyl-1-oxo-2-(1-propylbutyl)-1,2,3,4-tetrahydroisoquinoline-5-carboxamide Added to a solution of 33 mg of 7-methyl-1-oxo-2-(1-propylbutyl)-1,2,3,4-tetrahydroisoquinoline-5-carboxylic acid in 0.5 cm³ of anhydrous dimethylformamide are 0.05 cm³ of triethylamine and 51 mg of (2R,3S)-3-amino-4-(3,5-difluorophenyl)-1-({1-[3-(trifluoromethyl)phenyl]cyclopropyl}amino)butan-2-ol hydrochloride (2:1), then 17 mg of 1-hydroxy-7-azabenzotriazole and 24 mg of 1-(3-dimethylaminopropyl)-3-ethylcarbodiimide hydrochloride. The solution is kept stirring for 15 h at a temperature close to 20° C. 20 cm³ of water and 30 cm³ of ethyl acetate are added to the reaction medium. After decanting, the organic phase is washed with 20 cm³ of a saturated aqueous solution of ammonium chloride, five lots of 20 cm³ of water, then 20 cm³ of a saturated aqueous solution of sodium chloride, dried over anhydrous magnesium sulfate, filtered and concentrated to dryness under reduced pressure (5 kPa). The residue is dissolved in 2 cm³ of dichloromethane then purified by flash chromatography over silica (column: 15 g; spherical silica of BP-SUP type, particle size: 20-40 µm; eluent: 60% heptane/40% ethyl acetate). After concentrating the fractions under reduced pressure, 68 mg of N-[(1S,2R)-1-(3,5-difluorobenzyl)-2-hydroxy-3-({1-[3-(trifluoromethyl)phenyl]cyclopropyl}amino)propyl]-7-methyl-1-oxo-2-(1-propylbutyl)-1,2,3,4-tetrahydroisoquinoline-5-carboxamide are obtained in the form of a colorless oil.

LC-MS-DAD-ELSD: [M+H]$^+$: m/z 686 (base peak); [2M+H]$^+$: m/z 1371

18.2: Salt N-[(1S,2R)-1-(3,5-difluorobenzyl)-2-hydroxy-3-({1-[3-(trifluoromethyl)phenyl]cyclopropyl}amino)propyl]-7-methyl-1-oxo-2-(1-propylbutyl)-1,2,3,4-tetrahydroisoquinoline-5-carboxamide hydrochloride (1:1)

68 mg of N-[(1S,2R)-1-(3,5-difluorobenzyl)-2-hydroxy-3-({1-[3-(trifluoromethyl)phenyl]cyclopropyl}amino)propyl]-7-methyl-1-oxo-2-(1-propylbutyl)-1,2,3,4-tetrahydroisoquinoline-5-carboxamide are dissolved, under an argon atmosphere, in 5 cm$^3$ of ethyl ether. 0.2 cm$^3$ of a 4N solution of hydrochloric acid in dioxane is added, while stirring, at a temperature of 20° C. The reaction mixture is concentrated to dryness under reduced pressure (5 kPa). The residue is taken up with 10 cm$^3$ of ethyl ether, concentrated to dryness under reduced pressure (5 kPa), and dried under vacuum at a temperature of 35° C. 69 mg of N-[(1S,2R)-1-(3,5-difluorobenzyl)-2-hydroxy-3-({1-[3-(trifluoromethyl)phenyl]cyclopropyl}amino)propyl]-7-methyl-1-oxo-2-(1-propyl butyl)-1,2,3,4-tetrahydroisoquinoline-5-carboxamide hydrochloride (1:1) are obtained in the form of a white powder.

NMR: 0.84 (m, 6H); from 1.10 to 1.70 (m, 12H); from 2.24 to 2.45 (partially masked m, 2H); 2.29 (s, 3H); 2.61 (m, 1H); 2.79 (m, 1H); from 2.98 to 3.18 (m, 4H); 3.80 (m, 1H); 4.09 (m, 1H); 4.64 (m, 1H); 5.87 (broad m, 1H); 6.87 (broad s, 1H); 6.96 (m, 2H); 7.09 (broad t, J=9.0 Hz, 1H); 7.68 (broad t, J=7.5 Hz, 1H); 7.75 (broad s, 1H); 7.79 (broad d, J=7.5 Hz, 1H); 7.90 (broad d, J=7.5 Hz, 1H); 8.02 (broad s, 1H); 8.23 (broad d, J=8.0 Hz, 1H); 9.36 (broad m, 1H); 9.77 (broad m, 1H)

LC-MS-DAD-ELSD: [M+H]$^+$: m/z 686

EXAMPLE 19

19.1: Base N-[(1S,2R)-1-(3,5-difluorobenzyl)-2-hydroxy-3-({1-[3-(trifluoromethyl)phenyl]cyclopropyl}amino)propyl]-7-chloro-1-oxo-2-(1-propylbutyl)-1,2,3,4-tetrahydroisoquinoline-5-carboxamide

19.1.1: Methyl 7-chloro-1-oxo-2-(1-propylbutyl)-1,2,3,4-tetrahydroisoquinoline-5-carboxylate Added to a solution of 0.29 cm$^3$ of N-butyl nitrite in 20 cm$^3$ of acetonitrile, at a temperature close to 20° C., are 316 mg of cupric chloride. The temperature of the reaction mixture is lowered to 0° C., then, over 30 minutes, a solution of 0.5 g of methyl 7-amino-1-oxo-2-(1-propylbutyl)-1,2,3,4-tetrahydroisoquinoline-5-carboxylate dissolved in 20 cm$^3$ of acetonitrile is introduced. The stirring is continued for 3 h at a temperature close to 20° C. Added to the reaction medium are 30 cm$^3$ of water, then 50 cm$^3$ of a saturated aqueous solution of sodium bicarbonate and 100 cm$^3$ of ethyl acetate. The mixture is filtered and the organic phase is decanted, washed with 100 cm$^3$ of water, 100 cm$^3$ of a 1N aqueous solution of hydrochloric acid, then 100 cm$^3$ of water, 100 cm$^3$ of a saturated aqueous solution of sodium bicarbonate, 100 cm$^3$ of water and 100 cm$^3$ of a saturated aqueous solution of sodium chloride. The organic phase is dried over anhydrous magnesium sulfate, filtered and concentrated to dryness under reduced pressure (5 kPa). The residual oil is dissolved in 3 cm$^3$ of dichloromethane, then purified by flash chromatography over silica (column: 50 g; spherical silica of BP-SUP type, particle size: 20-40 µm; eluent: 60% heptane/40% ethyl acetate). After concentrating the fractions under reduced pressure, 243 mg of methyl 7-chloro-1-oxo-2-(1-propylbutyl)-1,2,3,4-tetrahydroisoquinoline-5-carboxylate are obtained in the form of a yellow oil.

NMR: 0.88 (t, J=7.5 Hz, 6H); from 1.11 to 1.30 (m, 4H); 1.40 (m, 2H); 1.52 (m, 2H); 3.19 (t, J=6.0 Hz, 2H); 3.32 (t, J=6.0 Hz, 2H); 3.88 (s, 3H); 4.62 (m, 1H); 7.98 (d, J=2.0 Hz, 1H); 8.08 (d, J=2.0 Hz, 1H)

LC-MS-DAD-ELSD: [M+H]$^+$: m/z 338 (base peak); [2M+Na]$^+$: m/z 697

19.1.2: 7-chloro-1-oxo-2-(1-propylbutyl)-1,2,3,4-tetrahydroisoquinoline-5-carboxylic acid 33 mg of methyl 7-chloro-1-oxo-2-(1-propylbutyl)-1,2,3,4-tetrahydroisoquinoline-5-carboxylate are dissolved in 6 cm$^3$ of dioxane at a temperature close to 20° C. 1.8 cm$^3$ of a 1N aqueous solution of sodium hydroxide are added, then the reaction mixture is heated at a temperature close to 60° C. for 1 h. The mixture is then concentrated to dryness under reduced pressure (5 kPa), taken up by 10 cm$^3$ of ethyl ether and 10 cm$^3$ of water. The aqueous phase is decanted, acidified with 1 cm$^3$ of a 2N aqueous solution of hydrochloric acid. The reaction medium is washed two times with 10 cm$^3$ of dichloromethane. The organic liquors are combined, dried over anhydrous magnesium sulfate, filtered and concentrated to dryness under reduced pressure (5 kPa). 215 mg of 7-methyl-1-oxo-2-(1-propylbutyl)-1,2,3,4-tetrahydroisoquinoline-5-carboxylic acid are obtained in the form of yellow crystals that are used directly in the following reaction.

19.1.3: N-[(1S,2R)-1-(3,5-difluorobenzyl)-2-hydroxy-3-({1-[3-(trifluoromethyl)phenyl]cyclopropyl}amino)propyl]-7-chloro-1-oxo-2-(1-propylbutyl)-1,2,3,4-tetrahydroisoquinoline-5-carboxamide Added, under an argon atmosphere and at a temperature close to 20° C., to a solution of 180 mg of 7-chloro-1-oxo-2-(1-propylbutyl)-1,2,3,4-tetrahydroisoquinoline-5-carboxylic acid in 2.2 cm$^3$ of anhydrous dimethylformamide are 0.25 cm$^3$ of triethylamine and 263 mg of (2R,3S)-3-amino-4-(3,5-difluorophenyl)-1-({1-[3-(trifluoromethyl)phenyl]cyclopropyl}amino)butan-2-ol hydrochloride (2:1), then 90 mg of 1-hydroxy-7-azabenzotriazole and 127 mg of 1-(3-dimethylaminopropyl)-3-ethylcarbodiimide hydrochloride. The solution is kept stirring, under argon, for 15 h at a temperature close to 20° C. The reaction medium is then added to 10 cm$^3$ of water and 20 cm$^3$ of ethyl acetate. After decanting, the organic phase is washed with 10 cm$^3$ of a saturated aqueous solution of ammonium chloride, five lots of 10 cm$^3$ of water, then 10 cm$^3$ of a saturated aqueous solution of sodium chloride, dried over anhydrous magnesium sulfate, filtered and concentrated under reduced pressure (5 kPa). The residual solution (around 2 cm$^3$) is purified by flash chromatography over silica (column: 15 g; spherical silica of BP-SUP type, particle size: 20-40 µm; eluent: 50% heptane/50% ethyl acetate). After concentrating the fractions under reduced pressure, 274 mg of N-[(1S,2R)-1-(3,5-difluorobenzyl)-2-hydroxy-3-({1-[3-(trifluoromethyl)phenyl]cyclopropyl}amino)propyl]-7-chloro-1-oxo-2-(1-propylbutyl)-1,2,3,4-tetrahydroisoquinoline-5-carboxamide are obtained in the form of a beige foam.

LC-MS-DAD-ELSD: [M+H]$^+$: m/z 706

19.2: Salt N-[(1S,2R)-1-(3,5-difluorobenzyl)-2-hydroxy-3-({1-[3-(trifluoromethyl)phenyl]cyclopropyl}amino)propyl]-7-chloro-1-oxo-2-(1-propylbutyl)-1,2,3,4-tetrahydroisoquinoline-5-carboxamide hydrochloride (1:1)

272 mg of N-[(1S,2R)-1-(3,5-difluorobenzyl)-2-hydroxy-3-({1-[3-(trifluoromethyl)phenyl]cyclopropyl}amino)propyl]-7-chloro-1-oxo-2-(1-propylbutyl)-1,2,3,4-tetrahydroisoquinoline-5-carboxamide are dissolved, under an argon atmosphere, in 5 cm³ of ethyl ether. 0.35 cm³ of a 4N solution of hydrochloric acid in dioxane is added, while stirring, at a temperature of 20° C. The reaction mixture is concentrated to dryness under reduced pressure (5 kPa). The residue is taken up with two lots of 10 cm³ of diisopropyl ether, concentrated to dryness under reduced pressure (5 kPa), and dried under vacuum at a temperature of 35° C. 277 mg of N-[(1S,2R)-1-(3,5-difluorobenzyl)-2-hydroxy-3-({1-[3-(trifluoromethyl)phenyl]cyclopropyl}amino)propyl]-7-chloro-1-oxo-2-(1-propylbutyl)-1,2,3,4-tetrahydroisoquinoline-5-carboxamide hydrochloride (1:1) are obtained in the form of a beige powder.

NMR: 0.87 (m, 6H); from 1.10 to 1.71 (m, 12H); 2.30 (m, 1H); 2.46 (partially masked m, 1H); 2.61 (m, 1H); 2.79 (m, 1H); from 3.00 to 3.20 (m, 4H); 3.84 (m, 1H); 4.10 (m, 1H); 4.61 (m, 1H); 5.88 (broad m, 1H); 6.97 (m, 2H); 7.08 (tt, J=2.0 and 9.0 Hz, 1H); 7.15 (d, J=2.5 Hz, 1H); 7.68 (t, J=7.5 Hz, 1H); 7.78 (broad d, J=7.5 Hz, 1H); 7.88 (d, J=2.5 Hz, 1H); 7.91 (broad d, J=7.5 Hz, 1H); 8.01 (broad s, 1H); 8.42 (broad d, J=8.0 Hz, 1H); 9.41 (broad unresolved m, 1H); 9.92 (broad unresolved m, 1H)

LC-MS-DAD-ELSD: [M+H]⁺: m/z 706; [M+H]⁻: m/z 704

EXAMPLE 20

20.1: Base N-[(1S,2R)-1-(3,5-difluorobenzyl)-2-hydroxy-3-({1-[3-(trifluoromethyl)phenyl]cyclopropyl}amino)propyl]-7-fluoro-1-oxo-2-(1-propylbutyl)-1,2,3,4-tetrahydroisoquinoline-5-carboxamide 20.1.1: N-[2-(2-bromo-4-fluorophenyl)ethyl]heptan-4-amine Added to a suspension of 1 g of 2-bromo-4-fluorophenethylamine hydrocloride in 25 cm³ of dichloromethane and under an inert atmosphere is 663 μL of triethylamine. After stirring for 30 min at a temperature close to 20° C., 5 cm³ of distilled water are added and the stirring is continued for 30 min. 15 cm³ of distilled water are added and the two phases are separated. The organic phase is washed with three lots of 10 cm³ of distilled water, then dried. Added to the solution obtained are successively 449 mg of 4-heptanone and 1.166 g of sodium triacetoxyborohydride. The reaction mixture is stirred for 15 h at a temperature close to 20° C. 20 cm³ of a saturated solution of sodium hydrogen carbonate are then added to the reaction medium. The organic phase is decanted and separated from the aqueous phase then washed successively with 15 cm³ of distilled water and 15 cm³ of a saturated solution of sodium chloride. The organic phase is dried then concentrated using a rotary evaporator under reduced pressure (5 kPa). 1.069 g of N-[2-(2-bromo-4-fluorophenyl)ethyl]heptan-4-amine are obtained in the form of a colorless oil.

NMR: ppm 0.84 (m, 6 H) 1.21-1.30 (m, 8 H) 1.38 (broad m, 1 H) 2.43 (m, 1 H) 2.69 (m, 2 H) 2.77 (m, 2 H) 7.18 (td, J=8.5, 2.5 Hz, 1 H) 7.40 (dd, J=8.5, 6.5 Hz, 1 H) 7.51 (dd, J=8.5, 2.5 Hz, 1 H)

LC-MS-DAD-ELSD: [M+H]⁺: m/z=316

20.1.2: Methyl[2-(2-bromo-4-fluorophenyl)ethyl](1-propylbutyl)carbamate 1.045 g of N-[2-(2-bromo-4-fluorophenyl)ethyl]heptan-4-amine in solution in 15 cm³ of anhydrous tetrahydrofuran and 502 mg of potassium carbonate are stirred under an inert atmosphere at a temperature in the vicinity of 20° C. 0.28 cm³ of methyl chloroformate is introduced over 10 min using a syringe. The reaction mixture is brought to reflux over 30 h, then filtered through celite and then concentrated using a rotary evaporator under reduced pressure (5 kPa). The residual oil is put into solution in 20 cm³ of dichloromethane. The organic phase is washed successively with 10 cm³ of an aqueous solution of hydrochloric acid (pH=2), then 3×20 cm³ of distilled water. The organic phase is then dried, then concentrated to dryness using a rotary evaporator under reduced pressure (5 kPa). The residual oil is taken up with 10 cm³ of diisopropyl ether. The solid which appears is filtered and the filtrate is concentrated to dryness using a rotary evaporator under reduced pressure (5 kPa) in order to result in 778 mg of methyl[2-(2-bromo-4-fluorophenyl)ethyl](1-propylbutyl)carbamate in the form of a beige oil.

NMR: 0.86 (t, J=7.3 Hz, 6 H) 1.13-1.54 (m, 8 H) 2.92 (m, 2 H) 3.16 (m, 2 H) 3.63 (broad s, 1 H) 3.65 (broad s, 2 H) 3.88 (broad m, 0.33 H) 3.99 (broad m, 0.67 H) 7.25 (td, J=8.7, 2.7 Hz, 1 H) 7.39 (broad m, 1 H) 7.57 (dd, J=8.7, 2.7 Hz, 1 H)

LC-MS-DAD-ELSD: [M+H]⁺: m/z=374

20.1.3: 5-Bromo-7-fluoro-2-(1-propylbutyl)-3,4-dihydroisoquinoline-1(2H)-one 540 mg of methyl[2-(2-bromo-4-fluorophenyl)ethyl](1-propylbutyl)carbamate are dissolved under an inert atmosphere in 40 cm³ of dichloromethane at a temperature close to 20° C. 529 mg of 4-dimethylaminopyridine are added to the reaction mixture. The latter is cooled to a temperature in the vicinity of 0° C. 1.91 cm³ of trifluoromethanesulfonic anhydride in solution in 15 cm³ of anhydrous dichloromethane are poured into the reaction mixture over 30 min. The suspension is kept stirring for 15 h at a temperature close to 20° C. 20 cm³ of a saturated aqueous solution of sodium hydrogen carbonate are added to the reaction medium. This stirring is continued for 30 min, then 20 cm³ of dichloromethane are added to the mixture. The organic phase is decanted then washed successively with 100 cm³ of a 0.1M aqueous solution of hydrochloric acid and 20 cm³ of a saturated aqueous solution of sodium hydrogen carbonate. Next, the organic phase is dried then concentrated using a rotary evaporator under reduced pressure (5 kPa). The residual brown oil is then taken up in ethyl acetate and purified by filtration through silica (silica 60—particle size 15-40 μm). The organic phase is concentrated under reduced pressure (5 kPa). 477 mg of 5-bromo-7-fluoro-2-(1-propylbutyl)-3,4-dihydroisoquinoline-1(2H)-one are obtained in the form of a dark orange oil.

NMR: 0.88 (t, J=7.3 Hz, 6 H) 1.13-1.33 (m, 4 H) 1.42 (m, 2 H) 1.53 (m, 2 H) 2.94 (t, J=6.7 Hz, 2 H) 3.38 (t, J=6.7 Hz, 2 H) 4.64 (m, 1 H) 7.67 (dd, J=8.9, 2.7 Hz, 1 H) 7.80 (dd, J=8.9, 2.7 Hz, 1 H)

LC-MS-DAD-ELSD: [M+H]⁺: m/z=342

20.1.4: 7-fluoro-1-oxo-2-(1-propylbutyl)-1,2,3,4-tetrahydroisoquinoline-5-carboxylic acid Introduced successively, at a temperature close to 20° C., into a three-necked flask that is stirred and purged using carbon monoxide are 655 mg of 5-bromo-7-fluoro-2-(1-propylbutyl)-3,4-dihydroisoquinoline-(1(2H)-one, 25 cm³ of dimethylformamide, 2 cm³ of water, 723 mg of potassium acetate, 334 mg of potassium iodide, 43 mg of palladium acetate and 102 mg of triphenylphosphine. The reaction mixture is subjected to a carbon monoxide bubbling, then it is heated at 100° C. for 6 h. The reaction mixture is cooled to 25° C., then concentrated using a rotary evaporator under reduced pressure (5 kPa). The residue is taken up in 50 cm³ of ethyl acetate. The pH is alcalinized with 5M sodium hydroxide (pH>10). The two phases are filtered through celite then decanted and separated. The aqueous phase is acidified, while stirring, with a 5M solution of hydrochloric acid (pH=2), then extracted with 30 cm³ of ethyl acetate. The organic phase is dried over magnesium sulfate and concentrated using a rotary evaporator under reduced pressure (5 kPa). 166 mg of 7-fluoro-1-oxo-2-(1-propylbutyl)-1,2,3,4-tetrahydroisoquinoline-5-carboxylic acid are obtained in the form of a dark orange solid.

NMR: 0.87 (t, J=7.3 Hz, 6 H) 1.12-1.30 (m, 4 H) 1.40 (m, 2 H) 1.52 (m, 2 H) 3.22 (m, 2 H) 3.31 (partially masked m, 2 H) 4.64 (m, 1 H) 7.74 (dd, J=9.0, 2.9 Hz, 1 H) 7.82 (dd, J=9.0, 2.9 Hz, 1 H) 13.47 (broad unresolved M, 1 H)

LC-MS-DAD-ELSD: [M+H]⁺ m/z=308; [M−H]⁻ m/z=306

MP: 142.8° C.

20.1.5: N-[(1S,2R)-1-(3,5-difluorobenzyl)-2-hydroxy-3-({1-[3-(trifluoromethyl)phenyl]cyclopropyl}amino)propyl]-7-fluoro-1-oxo-2-(1-propylbutyl)-1,2,3,4-tetrahydroisoquinoline-5-carboxamide Added, under an argon atmosphere and at a temperature close to 20° C., to a solution of 150 mg of 7-fluoro-1-oxo-2-(1-propylbutyl)-1,2,3,4-tetrahydroisoquinoline-5-carboxylic acid in 20 cm³ of dichloromethane are 0.35 cm³ of N,N-diisopropylethylamine, 6 mg of 4-dimethylaminopyridine and 235 mg of (2R,3S)-3-amino-4-(3,5-difluorophenyl)-1-({1-[3-trifluoromethyl)phenyl]cyclopropyl}amino)butan-2-ol hydrochloride then 10 mg of 1-hydroxy-7-azabenzotriazole and 119 mg of 1-(3-dimethylaminopropyl)-3-ethylcarbodiimide hydrochloride. The solution is kept stirring under argon for 15 h at a temperature close to 20° C. The reaction medium is then concentrated under reduced pressure (5 kPa). The residual solid is purified by flash chromatography over silica (column: 90 g; silica of the type: SuperVarioPrep D40-Si60 particle size: 15-40 µm; eluent: 50% cyclohexane/50% ethyl acetate). After concentrating the fractions under reduced pressure, 1 g of N-[(1S,2R)-1-(3,5-difluorobenzyl)-2-hydroxy-3-({1-[3-(trifluoromethyl)phenyl]cyclopropyl}amino)propyl]-7-fluoro-1-oxo-2-(1-propylbutyl)-1,2,3,4-tetrahydroisoquinoline-5-carboxamide is obtained in the form of a beige foam.

20.2: Salt N-[(1S,2R)-1-(3,5-difluorobenzyl)-2-hydroxy-3-({1-[3-(trifluoromethyl)phenyl]cyclopropyl}amino)propyl]-7-fluoro-1-oxo-2-(1-propyl butyl)-1,2,3,4-tetrahydroisoquinoline-5-carboxamide hydrochloride (1:1)

The foam obtained in step 19.1.5 is dissolved in 10 cm³ of ethyl ether. 4 cm³ of a 1N solution of hydrochloric acid in ethyl ether, then 1 cm³ of ethanol, are added, while stirring, at a temperature of 20° C. The reaction mixture is concentrated to dryness under reduced pressure (5 kPa). The residue is triturated with 10 cm³ of diisopropyl ether, the solid formed is filtered, then dried under atmospheric pressure at a temperature close to 20° C. 249 mg of N-[(1S,2R)-1-(3,5-difluorobenzyl)-2-hydroxy-3-({1-[3-(trifluoromethyl)phenyl]cyclopropyl}amino)propyl]-7-fluoro-1-oxo-2-(1-propylbutyl)-1,2,3,4-tetrahydroisoquinoline-5-carboxamide hydrochloride (1:1) are obtained in the form of a white solid.

NMR: 0.86 (m, 6H); from 0.93 to 1.09 (m, 4H); from 1.11 to 1.28 (m, 4H); from 1.32 to 1.56 (m, 4H); from 2.30 to 2.73 (partially masked m, 5H); from 3.03 to 3.15 (m, 4H); 3.54 (m, 1H); 4.12 (m, 1H); 4.61 (m, 1H); 4.95 (d, J=6.0 Hz, 1H); 6.93 (m, 2H); 7.08 (tt, J=2.0 and 9.0 Hz, 1H); 7.12 (d, J=2.5 Hz, 1H); 7.52 (m, 2H); 7.59 (m, 1H); 7.69 (broad s, 1H); 7.85 (d, J=2.5 Hz, 1H); 8.29 (broad d, J=8.0 Hz, 1H)

LC-MS-DAD-ELSD [M+H]+m/z=690 (base peak); [2M+H]+m/z=1379

Table 1 below illustrates the chemical structures and the physical properties of some examples of compounds according to the invention. In this table:

MP (° C.) represents the melting point of the compound in degrees Celsius;

in the "salt" column, "-" represents a compound in the free base form, whereas "HCl" represents a compound in the hydrochloride form and the ratio between parentheses is the (acid:base) ratio;

"nd" signifies not determined;

Me represents a methyl group; and

R3 represents a trifluoromethyl group.

The compounds described in this table were prepared according to the methods described previously.

TABLE 1

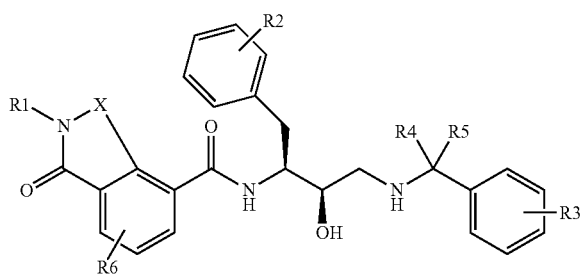

(I)

| Compound | R1 | X | R2 | R4, R5 | R6 | Salt | MP (° C.) |
|---|---|---|---|---|---|---|---|
| 1 | (n-C₃H₇)₂CH— | —CH₂— | H— | H—, H— | H— | HCl (1:1) | nd⁽ᵃ⁾ |

TABLE 1-continued (I)

| Compound | R1 | X | R2 | R4, R5 | R6 | Salt | MP (° C.) |
|---|---|---|---|---|---|---|---|
| 2 | (n-C$_3$H$_7$)$_2$CH— | —CH$_2$CH$_2$— | H— | —CH$_2$CH$_2$— | H— | HCl (1:1) | 174 |
| 3 | (n-C$_3$H$_7$)$_2$CH— | —CH$_2$CH$_2$— | 3,5-diF | —CH$_2$CH$_2$— | H— | HCl (1:1) | 172 |
| 4 | (n-C$_3$H$_7$)$_2$CH— | —CH$_2$CH$_2$— | H— | H—, H— | H— | HCl (1:1) | nd[a] |
| 5 | C$_6$H$_5$CH$_2$— | —CH$_2$CH$_2$— | 3,5-diF | —CH$_2$CH$_2$— | H— | HCl (1:1) | 178 |
| 6 | n-C$_5$H$_{11}$ | —CH$_2$CH$_2$— | 3,5-diF | —CH$_2$CH$_2$— | H— | HCl (1:1) | 165 |
| 7 | CH$_3$OCH$_2$CH$_2$— | —CH$_2$CH$_2$— | 3,5-diF | —CH$_2$CH$_2$— | H— | HCl (1:1) | nd[a] |
| 8 | CH$_3$CH$_2$OCH$_2$CH$_2$— | —CH$_2$CH$_2$— | 3,5-diF | —CH$_2$CH$_2$— | H— | HCl (1:1) | nd[a] |
| 9 | (n-C$_3$H$_7$)$_2$CH— | —CH$_2$CH$_2$— | 3,5-diF | —CH$_2$CH$_2$— | 7-NMeSO$_2$Me | HCl (1:1) | nd[a] |
| 10 | 4-F—C$_6$H$_4$CH(Me)- | —CH$_2$CH$_2$— | 3,5-diF | —CH$_2$CH$_2$— | H— | HCl (1:1) | 157 |
| 11 | (n-C$_3$H$_7$)$_2$CH— | —CH(CH$_3$)— | 3,5-diF | —CH$_2$CH$_2$— | 6-NMeSO$_2$Me | HCl (1:1) | 193 |
| 12 | (n-C$_3$H$_7$)$_2$CH— | —CH$_2$— | 3,5-diF | —CH$_2$CH$_2$— | 6-NMeSO$_2$Me | HCl (1:1) | 194 |
| 13 | (n-C$_3$H$_7$)$_2$CH— | —CH$_2$CH$_2$— | 3,5-diF | —CH$_2$CH$_2$— | 7-CF$_3$ | HCl (1:1) | 196 |
| 14 | (n-C$_3$H$_7$)$_2$CH— | —CH$_2$CH$_2$— | 3,5-diF | —CH$_2$CH$_2$— | 7-NHSO$_2$Me | HCl (1:1) | nd[a] |
| 15 | (n-C$_3$H$_7$)$_2$CH— | —CH$_2$CH$_2$— | 3,5-diF | —CH$_2$CH$_2$— | 7-(oxazol-5-yl) | HCl (1:1) | nd[b] |
| 16 | (n-C$_3$H$_7$)$_2$CH— | —CH$_2$CH$_2$— | 3,5-diF | —CH$_2$CH$_2$— | 7-[(3-CN)C$_6$H$_5$] | HCl (1:1) | nd[b] |
| 17 | (n-C$_3$H$_7$)$_2$CH— | —CH$_2$CH$_2$— | 3,5-diF | —CH$_2$CH$_2$— | 7-[(2-CN)C$_6$H$_5$] | HCl (1:1) | nd[b] |
| 18 | (n-C$_3$H$_7$)$_2$CH— | —CH$_2$CH$_2$— | 3,5-diF | —CH$_2$CH$_2$— | 7-Me | HCl (1:1) | nd[b] |
| 19 | (n-C$_3$H$_7$)$_2$CH— | —CH$_2$CH$_2$— | 3,5-diF | —CH$_2$CH$_2$— | 7-Cl | HCl (1:1) | nd[b] |
| 20 | (n-C$_3$H$_7$)$_2$CH— | —CH$_2$CH$_2$— | 3,5-diF | —CH$_2$CH$_2$— | 7-F | HCl (1:1) | nd[b] |

[a]characterized by a $^1$H NMR spectrum and by liquid chromatography coupled to a mass spectrometer
[b]characterized by a $^1$H NMR spectrum The compounds according to the invention have been the subject of pharmacological tests enabling their inhibitory effect with respect to β-secretase activity to be determined.

The tests consisted in measuring the in vitro inhibition of the β-secretase activity by the compounds of the invention.

The β-secretase activity measured corresponds to that of a purified recombinant form of human BACE1 aspartyl protease (the latter comprising a hexahistidine tag at the C-terminal position) produced by expression in *Drosophila* cells. The purified enzyme is conditioned in TRIS buffer (18 mM) at pH 7.5 containing NaCl (0.45M), MnCl$_2$ (0.9 mM), CaCl$_2$ (0.9 mM), α-D-methylmannoside and 10% glycerol, and stored at −80° C. until use.

The BACE1 activity is measured from the cleavage of a fluorogenic peptide substrate, known as FS1, described originally by Ermolieff et Coll. (2000, Biochemistry, 39, 12450-12456), and based on the principle of fluorescence resonance energy transfer (FRET); the cleavage of the FS1 peptide is measured from the increase of the fluorescent signal emitted by the EDANS (or 5-[(2-aminoethyl)amino]naphthalene-2-sulfonic acid) group. The test is carried out in a 96-well microplate in order to determine the inhibition of the enzyme activity by the products of the invention. The substrate FS1 is solubilized to a concentration of 1 mM in 100% dimethylsulfoxide (DMSO) and stored at −20° C. until use. The dilutions of the products to be tested are prepared in DMSO starting from a 10 mM stock solution. The products of the invention, at final concentrations of 0.003 to 10 μM are incubated at 37° C. with the substrate FS1 (final concentration of 5 μM) and the purified enzyme (final concentration of 10 nM) in the sodium acetate buffer (0.1M), pH 4.5 containing 0.02% of CHAPS detergent and 200 mM NaCl for 45 minutes. The final percentage of DMSO does not exceed 7%. When the incubation is finished, the fluorescence is measured in a spectrofluorimeter, at the excitation wavelength of 355 nm and emission wavelength of 509 nm. For each product concentration tested, the fluorescent signal is compared to the maximum signal obtained when the substrate FS1 is only incubated with the enzyme.

The inhibitory activity of the products of the invention is then evaluated by the measurement of the $IC_{50}$ (concentration of product giving 50% inhibition of the enzyme activity) using a non-linear regression analysis (computer application software XLfit, IDBS™).

The $IC_{50}$ values are between 0.01 µM and 5 µM.

The better compounds according to the invention have $IC_{50}$ values of between 10 nM and 500 nM.

For example, compounds No. 1, 9, 16 and 17 showed an $IC_{50}$ of 0.77 µM; 0.048 µM; 0.39 µM and 0.63 µM respectively.

It therefore appears that the compounds according to the invention have an inhibitory activity with respect to the activity of β-secretase.

The compounds according to the invention may therefore be used for the preparation of medicaments, in particular medicaments that inhibit the production of Aβ.

Thus, another subject of the invention is, according to another of its aspects, medicaments which comprise a compound of formula (I) or an addition salt of the latter with a pharmaceutically acceptable acid, or else a hydrate or a solvate of the compound of formula (I).

These medicaments find their use in therapeutics, especially in the treatment and prevention of diseases associated with the production of the Aβ peptide, among which mention may be made of neurodegenerative diseases such as Alzheimer's disease, Parkinson's disease, Huntington's disease, Creutzfeldt-Jakob disease, Down's syndrome, dementia with Lewy bodies, senile dementia, frontotemporal dementia, cerebral and systemic amyloidosis, mild cognitive impairments, cerebral amyloid angiopathy, primary and secondary memory disorders, amyotrophic lateral sclerosis, multiple sclerosis, peripheral neuropathies, diabetic neuropathies, migraine, mood disorders, depression, anxiety, vascular disorders such as atherosclerosis, cerebrovascular ischemia, tumors and cell proliferation disorders.

These medicaments find, in particular, their use in the treatment and the prevention of neurodegenerative diseases such as Alzheimer's disease, Parkinson's disease, Down's syndrome, dementia with Lewy bodies, senile dementia, frontotemporal dementia, cerebral and systemic amyloidosis, mild cognitive impairments, cerebral amyloid angiopathy, primary and secondary memory disorders and cerebrovascular ischemia.

According to another of its aspects, the present invention relates to pharmaceutical compositions comprising, as the active principle, a compound according to the invention. These pharmaceutical compositions contain an effective dose of at least one compound according to the invention, or a pharmaceutically acceptable salt, a hydrate or solvate of said compound, and also at least one pharmaceutically acceptable excipient. Said excipients are chosen, depending on the pharmaceutical form and the desired method of administration, from the customary excipients which are known to a person skilled in the art.

In the pharmaceutical compositions of the present invention for oral, sublingual, subcutaneous, intramuscular, intravenous, topical, local, intra-tracheal, intranasal, transdermal or rectal administration, the active principle of formula (I) above, or its optional salt, solvate or hydrate, may be administered in unit administration form, as a mixture with conventional pharmaceutical excipients, to animals and human beings for the prophylaxis or the treatment of the above disorders or diseases.

The suitable unit administration forms comprise oral forms, such as tablets, soft or hard gelatin capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. For topical application it is possible to use the compounds according to the invention in creams, gels, ointments or lotions.

By way of example, a unit administration form of a compound according to the invention in tablet form may comprise the following components:

| Compound according to the invention | 50.0 mg |
| Mannitol | 223.75 mg |
| Croscarmellose sodium | 6.0 mg |
| Maize starch | 15.0 mg |
| Hydroxypropyl methyl cellulose | 2.25 mg |
| Magnesium stearate | 3.0 mg |

The present invention, according to another of its aspects, also relates to a method for treating the pathologies indicated above which comprises the administration, to a patient, of an effective dose of a compound according to the invention, or one of its pharmaceutically acceptable salts or hydrates or solvates.

We claim:

1. A compound of formula (I):

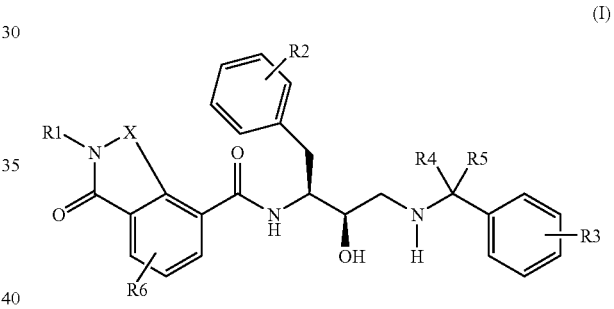

wherein:

R1 is hydrogen, $(C_1-C_{10})$alkyl, $(C_3-C_7)$cycloalkyl, $(CH_2)_n$—$(C_1-C_6)$alkenyl, $(CH_2)_n$—$(C_1-C_6)$alkynyl, $(C_1-C_6)$alkyl-Z—$(C_1-C_6)$alkyl, COOR, $S(O)_m$R, aryl or aralkyl, wherein the $(C_1-C_{10})$alkyl, $(C_3-C_7)$cycloalkyl, $(CH_2)_n$—$(C_1-C_6)$alkenyl, $(CH_2)_n$—$(C_1-C_6)$alkynyl, $(C_1-C_6)$alkyl-Z—$(C_1-C_6)$alkyl, aryl and aralkyl are optionally substituted with one or more groups chosen from halogen, $(C_1-C_6)$alkyl, $(C_3-C_7)$cycloalkyl, halo$(C_1-C_6)$alkyl, $(C_1-C_6)$alkoxy, halo$(C_1-C_6)$alkoxy, NR7R8, nitro, cyano, OR, COOR, CONR7R8, $S(O)_m$NR7R8 and aryl, wherein the aryl is optionally substituted with halogen;

R2 is one or more groups chosen from hydrogen, halogen, $(C_1-C_6)$alkyl, $(C_3-C_7)$cycloalkyl, $(C_1-C_6)$alkenyl, $(C_1-C_6)$alkynyl, $(C_1-C_6)$alkyl-Z—$(C_1-C_6)$alkyl, halo$(C_1-C_6)$alkyl, $(C_1-C_6)$alkoxy, halo$(C_1-C_6)$alkoxy, hydroxy, nitro, cyano, amino, NR7R8, COOR, CONR7R8, OCO$(C_1-C_6)$alkyl, $S(O)_m$—NR7R8 and aryl, wherein the aryl is optionally substituted with one or more groups chosen from halogen, $(C_1-C_6)$alkyl, $(C_3-C_7)$cycloalkyl, halo$(C_1-C_6)$alkyl, $(C_1-C_6)$alkoxy, halo$(C_1-C_6)$alkoxy, NR7R8, OR, nitro, cyano, COOR, CONR7R8 and $S(O)_m$ NR7R8;

R3 is trifluoromethyl;

R4 and R5 are hydrogen, or

R4 and R5 taken together with the carbon atom to which they are attached form a saturated ring containing from 3 to 6 carbon atoms and optionally containing from 0 to 1 heteroatom, chosen from O, N and S;

R6 is hydrogen, halogen, $(C_1-C_6)$alkyl, $(C_3-C_7)$cycloalkyl, $(C_3-C_7)$cycloalkyl$(C_1-C_6)$alkyl, halo$(C_1-C_6)$alkyl, nitro, amino, NR7R8, COOR, NR7(SO$_2$)R8, CONR7R8, aryl, or heterocycle, wherein the aryl and heterocycle are optionally substituted with one or more groups chosen from halogen, $(C_1-C_6)$alkyl, $(C_1-C_6)$alkoxy and cyano;

R, R7 and R8 are, independently of one another, hydrogen, $(C_1-C_6)$alkyl, $(C_3-C_7)$cycloalkyl, $(C_3-C_7)$cycloalkyl $(C_1-C_6)$alkyl group, aryl or aryl$(C_1-C_6)$alkylene, or R7 and R8 taken together with the nitrogen atom to which they are attached form a saturated, partially unsaturated or unsaturated ring containing from 5 to 7 carbon atoms and optionally containing, in addition, a heteroatom chosen from O, N and S(O)$_m$;

X is $(C_1-C_2)$alkylene optionally substituted with one or more $(C_1-C_6)$alkyl;

Z is O, N or S(O)$_m$, m is 0, 1 or 2; and n is 1, 2, 3, 4, 5 or 6;

provided that the carbon bearing the benzyl group substituted by R2 is of S absolute configuration; and the carbon bearing the hydroxyl group is of R absolute configuration;

or an addition salt with an acid thereof.

2. The compound according to claim 1 or an addition salt with an acid of said compound, wherein X is methylene optionally substituted with one or more $(C_1-C_6)$alkyl.

3. The compound according to claim 1 or an addition salt with an acid with said compound, wherein X is ethylene substituted with one or more $(C_1-C_6)$alkyl.

4. The compound according to claim 1 or an addition salt with an acid with said compound, wherein R6 is hydrogen, halogen, $(C_1-C_6)$alkyl, halo$(C_1-C_6)$alkyl, NR7SO$_2$R8, aryl or heterocycle, wherein the aryl is optionally substituted with a cyano group.

5. The compound according to claim 1 or an addition salt with an acid with said compound, wherein R6 is hydrogen, chlorine, fluorine, methyl, trifluoromethyl, NMeSO$_2$Me, phenyl or oxazole, wherein the phenyl is substituted with a cyano group.

6. The compound according to claim 1 or an addition salt with an acid with said compound, wherein:

R1 is $(C_1-C_{10})$alkyl optionally substituted with one or more $(C_1-C_6)$alkyl groups,
aryl optionally substituted with halogen,
$(C_1-C_6)$alkyl-O—$(C_1-C_6)$alkyl, or
aralkyl optionally substituted with halogen;

R2 is one or more groups chosen from hydrogen and halogen;

R4 and R5 are hydrogen atom, or

R4 and R5 taken together with the carbon atom to which they are attached form a cyclopropyl group;

R6 is hydrogen, halogen, $(C_1-C_6)$alkyl, halo$(C_1-C_6)$alkyl, NR7SO$_2$R8, aryl or heterocycle, wherein the aryl is optionally substituted with a cyano group;

R7 is hydrogen or $(C_1-C_6)$alkyl; and

R8 is $(C_1-C_6)$alkyl.

7. The compound according to claim 1 or an addition salt with an acid with said compound, which is selected from:

N-[(1S,2R)-1-benzyl-2-hydroxy-3-{[3-(trifluoromethyl)benzyl]amino}-propyl]-1-oxo-2-(1-propylbutyl)isoindoline-4-carboxamide or the 1:1 hydrochloride salt thereof;

N-[(1S,2R)-1-benzyl-2-hydroxy-3-({1-[3-(trifluoromethyl)phenyl]cyclo-propyl}amino)propyl]-1-oxo-2-(1-propylbutyl)-1,2,3,4-tetrahydroiso-quinoline-5-carboxamide or the 1:1 hydrochloride salt thereof;

N-[(1S,2R)-1-(3,5-difluorobenzyl)-2-hydroxy-3-({1-[3-(trifluoromethyl)-phenyl]cyclopropyl}amino)propyl]-1-oxo-2-(1-propylbutyl)-1,2,3,4-tetra-hydroisoquinoline-5 -carboxamide or the 1:1 hydrochloride salt thereof;

N-[(1S,2R)-1-benzyl-2-hydroxy-3-{[3-(trifluoromethyl)benzyl]amino}-propyl]-1-oxo-2-(1-propylbutyl)-1,2,3,4-tetrahydroisoquinoline-5-carboxamide or the 1:1 hydrochloride salt thereof;

2-benzyl-N-[(1S,2R)-1-(3,5-difluorobenzyl)-2-hydroxy-3-({1-[3-(trifluoromethyl)phenyl]cyclopropyl}amino)propyl]-1-oxo-1,2,3,4-tetrahydroiso-quinoline-5-carboxamide or the 1:1 hydrochloride salt thereof;

N-[(1S,2R)-1-(3,5-difluorobenzyl)-2-hydroxy-3-({1-[3-(trifluoromethyl)phenyl]cyclopropyl}amino)propyl]-1-oxo-2-pentyl-1,2,3,4-tetrahydro-isoquinoline-5-carboxamide or the 1:1 hydrochloride salt thereof;

N-[(1S,2R)-1-(3,5-difluorobenzyl)-2-hydroxy-3-({1-[3-(trifluoromethyl)-phenyl]cyclopropyl}amino)propyl]-2-(2-methoxyethyl)-1-oxo-1,2,3,4-tetrahydroisoquinoline-5-carboxamide or the 1:1 hydrochloride salt thereof;

N-[(1S,2R)-1-(3,5-difluorobenzyl)-2-hydroxy-3-({1-[3-(trifluoromethyl)-phenyl]cyclopropyl}amino)propyl]-2-(2-ethoxyethyl)-1-oxo-1,2,3,4-tetrahydroisoquinoline-5 -carboxamide or the 1:1 hydrochloride salt thereof;

N-[(1S,2R)-1-(3,5-difluorobenzyl)-2-hydroxy-3-({1-[3-(trifluoromethyl)-phenyl]cyclopropyl}amino)propyl]-7-[methyl(methylsulfonyl)amino]-1-oxo-2-(1-propyl-butyl)-1,2,3,4-tetrahydroisoquinoline-5-carboxamide or the 1:1 hydrochloride salt thereof;

N-[(1S,2R)-1-(3,5-difluorobenzyl)-2-hydroxy-3-({1-[3-(trifluoromethyl)-phenyl]cyclopropyl}amino)propyl]-2-[1-(4-fluorophenyl)ethyl]-1-oxo-1,2,3,4-tetrahydroisoquinoline-5-carboxamide or the 1:1 hydrochloride salt thereof;

N-[(1S,2R)-1-(3,5-difluorobenzyl)-2-hydroxy-3-({1-[3-(trifluoromethyl)phenyl]cyclopropyl}amino)propyl]-6-[methyl(methylsulfonyl)amino]-1-oxo-2-(1-propylbutyl)isoindoline-3-methyl-4-carboxamide or the 1:1 hydrochloride salt thereof;

N-[(1S,2R)-1-(3,5-difluorobenzyl)-2-hydroxy-3-({1-[3-(trifluoromethyl)-phenyl]cyclopropyl}amino)propyl]-6-[methyl(methylsulfonyl)amino]-1-oxo-2-(1-propylbutyl)isoindoline-4-carboxamide or the 1:1 hydrochloride salt thereof;

N-[(1S,2R)-1-(3,5-difluorobenzyl)-2-hydroxy-3-({1-[3-(trifluoromethyl)-phenyl]cyclopropyl}amino)propyl]-7-trifluoromethyl-1-oxo-2-(1-propylbutyl)-1,2,3,4-tetrahydroisoquinoline-5-carboxamide or the 1:1 hydrochloride salt thereof;

N-[(1S,2R)-1-(3,5-difluorobenzyl)-2-hydroxy-3-({1-[3-(trifluoromethyl)-phenyl]cyclopropyl}amino)propyl]-7-[(methylsulfonyl)amino]-1-oxo-2-(1-propylbutyl)-1,2,3,4-tetrahydroisoquinoline-5-carboxamide or the 1:1 hydrochloride salt thereof;

N-[(1S,2R)-1-(3,5-difluorobenzyl)-2-hydroxy-3-({1-[3-(trifluoromethyl)-phenyl]cyclopropyl}amino)propyl]-

7-(2-oxazolyl)-1-oxo-2-(1-propylbutyl)-1,2,3,4-tetrahydroisoquinoline-5-carboxamide hydrochloride (1:1);

N-[(1S,2R)-1-(3,5-difluorobenzyl)-2-hydroxy-3-({1-[3-(trifluoromethyl)-phenyl]cyclopropyl}amino)propyl]-7-(3-cyanophenyl)-1-oxo-2-(1-propylbutyl)-1,2,3,4-tetrahydroisoquinoline-5-carboxamide or the 1:1 hydrochloride salt thereof;

N-[(1S,2R)-1-(3,5-difluorobenzyl)-2-hydroxy-3-({1-[3-(trifluoromethyl)-phenyl]cyclopropyl}amino)propyl]-7-(2-cyanophenyl)-1-oxo-2-(1-propylbutyl)-1,2,3,4-tetrahydroisoquinoline-5-carboxamide or the 1:1 hydrochloride salt thereof;

N-[(1S,2R)-1-(3,5-difluorobenzyl)-2-hydroxy-3-({1-[3-(trifluoromethyl)-phenyl]cyclopropyl}amino)propyl]-7-methyl-1-oxo-2-(1-propylbutyl)-1,2,3,4-tetrahydroisoquinoline-5-carboxamide or the 1:1 hydrochloride salt thereof;

N-[(1S,2R)-1-(3,5-difluorobenzyl)-2-hydroxy-3-({1-[3-(trifluoromethyl)-phenyl]cyclopropyl}amino)propyl]-7-chloro-1-oxo-2-(1-propylbutyl)-1,2,3,4-tetrahydroisoquinoline-5-carboxamide or the 1:1 hydrochloride salt thereof;and N-[(1S,2R)-1-(3,5-difluorobenzyl)-2-hydroxy-3-({1-[3-(trifluoromethyl)-phenyl]cyclopropyl}amino)propyl]-7-fluoro-1-oxo-2-(1-propylbutyl)-1,2,3,4-tetrahydroisoquinoline-5-carboxamide or the 1:1 hydrochloride salt thereof.

8. A pharmaceutical composition, comprising the compound according to claim 1 or an addition salt with an acid with said compound, and at least one pharmaceutically acceptable excipient.

9. A pharmaceutical composition, comprising the compound according to claim 2 or an addition salt with an acid of said compound, and at least one pharmaceutically acceptable excipient.

10. A pharmaceutical composition, comprising the compound according to claim 3 or an addition salt with an acid with said compound, and at least one pharmaceutically acceptable excipient.

11. A pharmaceutical composition, comprising the compound according to claim 4 or an addition salt with an acid with said compound, and at least one pharmaceutically acceptable excipient.

12. A pharmaceutical composition, comprising the compound according to claim 5 or an addition salt with an acid with said compound, and at least one pharmaceutically acceptable excipient.

13. A pharmaceutical composition, comprising the compound according to claim 6 or an addition salt with an acid with said compound, and at least one pharmaceutically acceptable excipient.

14. A pharmaceutical composition comprising the compound according to claim 7 or an addition salt with an acid with said compound, and at least one pharmaceutically acceptable excipient.

15. The compound according to claim 7 wherein the compound is N-[(1S,2R)-1-benzyl-2-hydroxy-3-{[3-(trifluoromethyl)benzyl]amino}-propyl]-1-oxo-2-(1-propylbutyl)isoindoline-4-carboxamide or the 1:1 hydrochloride salt thereof.

16. The compound according to claim 7 wherein the compound is N-[(1S,2R)-1-(3,5-difluorobenzyl)-2-hydroxy-3-({1-[3-(trifluoromethyl)-phenyl]cyclopropyl}amino)propyl]-7-[methyl(methylsulfonyl)amino]-1-oxo-2-(1-propylbutyl)-1,2,3,4-tetrahydroisoquinoline-5-carboxamide or the 1:1 hydrochloride salt thereof.

17. The compound according to claim 7 wherein the compound is N-[(1S,2R)-1-(3,5-difluorobenzyl)-2-hydroxy-3-({1-[3-(trifluoromethyl)-phenyl]cyclopropyl}amino)propyl]-7-(3-cyanophenyl)-1-oxo-2-(1-propylbutyl)-1,2,3,4-tetrahydroisoquinoline-5-carboxamide or the 1:1 hydrochloride salt thereof.

18. The compound according to claim 7 wherein the compound is N-[(1S,2R)-1-(3,5-difluorobenzyl)-2-hydroxy-3-({1-[3-(trifluoromethyl)-phenyl]cyclopropyl}amino)propyl]-7-(2-cyanophenyl)-1-oxo-2-(1-propylbutyl)-1,2,3,4-tetrahydroisoquinoline-5-carboxamide or the 1:1 hydrochloride salt thereof.

* * * * *